(12) United States Patent
Maesawa et al.

(10) Patent No.: US 7,374,857 B2
(45) Date of Patent: May 20, 2008

(54) BISMIDE COMPOUND, ACID GENERATOR AND RESIST COMPOSITION EACH CONTAINING THE SAME, AND METHOD OF FORMING PATTERN FROM THE COMPOSITION

(75) Inventors: Tsuneaki Maesawa, Saitama (JP); Fumiyoshi Urano, Saitama (JP); Masayuki Endo, Osaka (JP); Masaru Sasago, Osaka (JP)

(73) Assignees: Wako Pure Chemical Industries Ltd., Osaka (JP); Matsushita Electric Industrial Co., Ltd., Kadoma-Shi (JP)

( * ) Notice: Subject to any disclaimer, the term of this patent is extended or adjusted under 35 U.S.C. 154(b) by 362 days.

(21) Appl. No.: 10/496,014

(22) PCT Filed: Nov. 28, 2002

(86) PCT No.: PCT/JP02/12434

§ 371 (c)(1),
(2), (4) Date: May 28, 2004

(87) PCT Pub. No.: WO03/045915

PCT Pub. Date: Jun. 5, 2003

(65) Prior Publication Data
US 2005/0038261 A1    Feb. 17, 2005

(30) Foreign Application Priority Data

Nov. 30, 2001 (JP) ............... 2001-366005
Apr. 23, 2002 (JP) ............... 2002-120769

(51) Int. Cl.
*G03C 1/00* (2006.01)
*C07D 209/36* (2006.01)

(52) U.S. Cl. .......... 430/270.1; 430/920; 548/484; 548/485; 548/486

(58) Field of Classification Search ............... 548/484, 548/485, 486; 430/270.1, 920
See application file for complete search history.

(56) References Cited

U.S. PATENT DOCUMENTS

| | | | |
|---|---|---|---|
| 5,112,712 A | 5/1992 | Kasai et al. | |
| 5,164,278 A | 11/1992 | Brunsvold et al. | |
| 5,492,793 A | 2/1996 | Breyta et al. | |
| 5,585,218 A | 12/1996 | Nakano et al. | |
| 5,625,050 A | 4/1997 | Beaton et al. | |
| 5,679,495 A | 10/1997 | Yamachika et al. | |
| 5,760,165 A | 6/1998 | Dao et al. | |
| 5,985,511 A | 11/1999 | Yako et al. | |
| 6,150,068 A | 11/2000 | Sato et al. | |
| 6,156,476 A | 12/2000 | Takeyama et al. | |
| 6,171,755 B1 | 1/2001 | Elian et al. | |
| 6,280,911 B1 | 8/2001 | Trefonas, III | |
| 6,517,992 B1 | 2/2003 | Wang et al. | |
| 6,569,596 B1 | 5/2003 | Uetani et al. | |
| 6,582,879 B2 * | 6/2003 | Choi et al. ............... | 430/270.1 |
| 2003/0064315 A1 | 4/2003 | Choi et al. | |

FOREIGN PATENT DOCUMENTS

| | | |
|---|---|---|
| DE | 19540107 | 5/1996 |
| EP | 0388343 * | 2/1990 |
| EP | 388343 B1 | 9/1990 |
| EP | 424115 A2 | 4/1991 |
| EP | 613050 B1 | 8/1994 |
| EP | 827025 A1 | 3/1998 |
| JP | 61-166544 | 7/1986 |
| JP | 3-136061 | 6/1991 |
| JP | 3-206458 | 9/1991 |
| JP | 4-217251 | 8/1992 |
| JP | 5-216235 | 8/1993 |
| JP | 6-214395 | 8/1994 |
| JP | 6-266112 | 9/1994 |

(Continued)

OTHER PUBLICATIONS

Ohara et al., 1989, CAS: 111:40901.*

(Continued)

*Primary Examiner*—Rei-tsang Shiao
(74) *Attorney, Agent, or Firm*—Kratz, Quintos & Hanson, LLP

(57) ABSTRACT

The present invention relates to a novel bisimide compound useful as an acid generator for a chemically amplified resist composition used in manufacturing of semiconductor element and the like or a raw material for synthesizing heat resistant polymers, an acid generator and a resist composition using said compound and a method for pattern formation using said composition, and further relates to a synthetic n intermediate for a bisimide compound and a bis(N-hydroxy)phthalimide compound useful as an intermediate for a functional compound such as a heat resistant polymer or photosensitive material, and provides a bisimide compound shown by the general formula [1]:

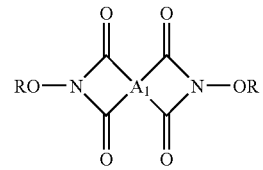

[1]

(wherein R and $A_1$ are as defined in claim 1).

13 Claims, 4 Drawing Sheets

FOREIGN PATENT DOCUMENTS

| | | |
|---|---|---|
| JP | 6-301200 | 10/1994 |
| JP | 7-209868 | 8/1995 |
| JP | 7-295220 | 11/1995 |
| JP | 8-501890 | 2/1996 |
| JP | 8-184965 | 7/1996 |
| JP | 9-166871 | 6/1997 |
| JP | 10-20502 | 1/1998 |
| JP | 10-62995 | 3/1998 |
| JP | 10-69082 | 3/1998 |
| JP | 10-78658 | 3/1998 |
| JP | 10-111570 | 4/1998 |
| JP | 11-2901 | 1/1999 |
| JP | 11-167199 | 6/1999 |
| JP | 11-231542 | 8/1999 |
| JP | 11-258801 | 9/1999 |
| JP | 11-352677 | 12/1999 |
| JP | 2000-89454 | 3/2000 |
| JP | 2000-147753 | 5/2000 |
| JP | 2000-155420 | 6/2000 |
| JP | 2000-267282 | 9/2000 |
| JP | 2000-330284 | 11/2000 |
| JP | 2000-330285 | 11/2000 |
| JP | 2000-347392 | 12/2000 |
| JP | 2001-199955 | 7/2001 |
| WO | WO94/10608 A1 | 5/1994 |

OTHER PUBLICATIONS

Choi et al. CAS: 138:294913.*

H. Ito, et al.; "The Annealing Concept for Environmental Stabilization of Chemical Amplification Resists"; *Microelectronics Technology, ACS Symposium Series 614;* Apr. 2-6, 1995; pp. 20-34.

H. Ito, et al.; "Lithographic Feasibility of ESCAP Beyond Quarter Micron"; *Journal of Photopolymer Science and Technology;* vol. 9; No. 4; 1996; pp. 557-572.

Y. Imai, et al.; "Synthesis of Polypyrimidoquinazolinetetraones from *N,N'*-Bis(mesyloxy)pyromellitimide and Aromatic Diamines"; *Journal of Polymer Science;* vol. 13; 1975; pp. 2391-2396.

The European Patent Office Communication for corresponding European patent application No. 02785967, dated Oct. 19, 2005.

Imai, Yoshio, et al.; "Synthesis of Polypyrimidoquinazolinetetraones from N, N'-Bis (mesyloxy) pyromellitimide and Aromatic Diamines;" *Journal of Polymer Science;* vol. 13, pp. 2391-2396 (1975).

* cited by examiner

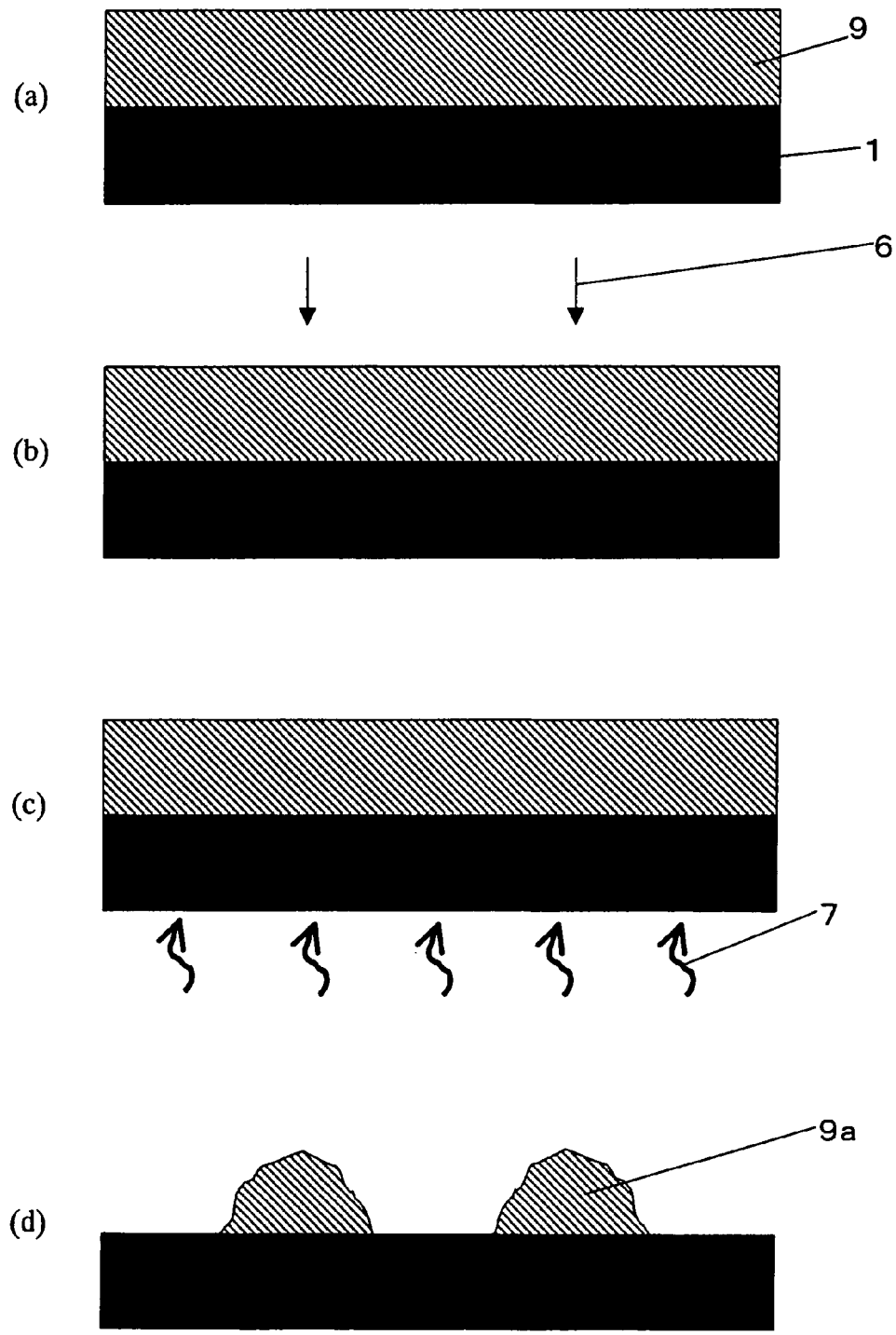

BISMIDE COMPOUND, ACID GENERATOR AND RESIST COMPOSITION EACH CONTAINING THE SAME, AND METHOD OF FORMING PATTERN FROM THE COMPOSITION

This application is a 371 of PCT/JP02/12434 filed on Nov. 28, 2002.

TECHNICAL FIELD

The present invention relates to a novel bisimide compound useful as an acid generator for a chemically amplified resist composition used in manufacturing of semiconductor element and the like or a raw material for synthesizing heat resistant polymers, an acid generator and a resist composition using said compound and a method for pattern formation using said composition, and further relates to a synthetic intermediate for a bisimide compound, and a bis(N-hydroxy)phthalimide compound useful as, for example, an intermediate for a functional compound such as a heat resistant polymer or a photosensitive material.

BACKGROUND OF THE INVENTION

In manufacturing of semiconductor elements as an example, with the recent trend of higher density integration in semiconductor devices, wavelengths of energy sources for irradiation instruments used in fine processing, particularly those used in lithography, have become shorter and shorter, and now deep UV (300 nm or less) and KrF excimer laser (248 nm) have already been made into practical use, and ArF excimer laser (193 nm) is close to practical use. Further studies for exposure technology using $F_2$ laser (157 nm), electron beams, extreme UV (EUV: 1 to 30 nm band) and the like has been promoted for the purpose of ultrafine fabrication of 100 nm or less. In resist compositions under development for these applications, various known acid generators are used, but use of these known acid generators causes various problems.

For example, when a diazodisulfone compound having an aliphatic alkyl group, which is presently used, is used as an acid generator, the compound has such problems that strong acid cannot be generated or acid generation efficiency is poor, whereas, use of a diazodisulfone compound having an aromatic group as an acid generator, also has problems such as poor solution stability. Further, when a sulfonium salt or an iodonium salt is used as an acid generator, there are also such problems that fine particles are easily formed due to poor solubility, storage for several weeks is difficult due to poor solution stability, and when said salt has a counter anion derived from trifluuoromethanesulfonic acid, easy variations in resist performances are caused; (e.g. variations in dimension, sensitivity, shape and the like) and thus a practically suitable acid generator has not been found.

Further, as a resist composition using an imidesulfdnate compound as an acid generator, the following resist compositions have been disclosed: use of a combination of poly(hydroxystyrene/styrene/tert-butyl acrylate) and N-trifluoromethylsulfonyloxy-bicyclo-[2.2.1]-hept-5-ene-2,3-dicarboxyimide (see JP-A-7-209868); use of a combination of poly(p-hydroxystyrene/tert-butyl acrylate) and N-camphorsulfonyloxynaphthalimide or N-trifluoromethylsulfonyloxy-bicyclo-[2.2.1]-hept-5-ene-2,3-dicarboxyimide [see H. Ito et al., ACS. Symp. Ser., 1995, vol.614 (Microelectronics Technology), p 21-34; H. Ito et al., J. Photopolym. Sci. Technol., 1996, vol. 9 (No. 4), p. 557-572; and JP-A-6-266112]; use of N-pentafluorobenzenesulfonyloxy-bicyclo-[2.2.1]-hept-5-ene-2,3-dicarboxyimide (see JP-A-3-206458); use of a combination of poly(styrene/p-hydrbxystyrene/p-tert-butoxycarbonylmethoxystyrene) and N-benzenesulfonyloxysuccinimide (see JP-A 6-214395) and use of N-norbornanesulfonyloxy-bicyclo-[2.2.1]-hept-5-ene-2,3-dicarboxyimide (see JP-A-2001-199955). However, these N-imidesulfonate compounds have such problems that the resist composition using these compounds is, due to asymmetric structure and high reactivity thereof, labile to moisture and the like, and thus gives a solution with poor solution stability, low acid generation efficiency and low sensitivity. In addition, a N-imidesulfonate compound having a counter anion derived from trifluoromethanesulfonic acid also has a problem such as easy variation in resist performances, similar to the above.

As an analogous compound to a bisimide compound of the present invention, for example, 2,6-bis(methanesulfonyloxy)benzo[1,2-c:4,5-c']dipyrrole-1,3,5,7(2H, 6H)-tetrone [see Y. Imai et al., J. Polym. Sci. Polym. Chem. Ed., 1975, vol. 13 (No. 10), p. 2391-2396;-DE-A-19540107 and the like] has been reported. However, these compounds are, used as a raw material for a polyimide compound and not relates to an acid generator, and even if use of said, compouds as an acid generator is intended, they cannot be used due to extremely poor solubility in a resist solvent. Further, 3a,4,4a,7a,8,8a-hexahydro-2,6-bis(butanesulfonyloxy)-4,8-ethenobenzo[1,2-c:4,5-c']dipyrrole-1,3,5,7(2H, 6H)-tetrone (see JP7A-11-258801) has also been reported. However, this compound was used as a cross-linking agent for a chemically amplified negative resist composition and not relates to an acid generator, and even if use of said compound as an acid generator is intended, it cannot be used due to low sensitivity, low resolution and poor profile.

Further, as other analogous compounds to a bisimide compound of the present invention, for example, 5,5'-oxybis[2-trifluoromethanesulfonyloxy-1H-isoindole-1,3(2H)-dione] and 5,5'-[2,2,2-trifluoro-1-(trifluoromethyl)ethylidene]bis[2-trifluoromethanesulfonyloxy-1H-isoindole-1,3(2H)-dione] (see JP-A-3-206458, JP-A-6-301200, JP-A-8-501890 and the like), and 5,5'-oxybis[2-(4-toluenesulfonyl)oxy-1H-isoindole-1,3(2H)-dione] (see JP-A-11-167199) have been reported as an acid generator for chemically amplified resist materials. However, these compounds cannot be practically used as a resist composition due to no solubility in a resist solvent generally used.

As described above, conventional acid generators practically used or studied have the following problems: an acid generated is weak; acid generation efficiency is insufficient; fine particles are easily formed due to poor solubility; use of said acid generator as a resist compositions occurs decomposition during storage due to poor solution stability resulting in variation in sensitivity or poor pattern formation; and a resist composition itself cannot be prepared due to little solubility in a resist solvent. Thus, development of a useful compound which can solve these problems and generates an acid in response to radioactive ray, is now demanded.

SUMMARY OF THE INVENTION

The present invention has been completed under such circumstances as mentioned above, and the theme of the invention is to provide a novel compound efficiently generating an acid in response to radiation, an acid generator and a resist composition using said compound and a method for pattern formation using said composition, along with an intermediate for synthesizing an acid generating compound.

The present invention has an object to solve the above-described problems, and provides the following.

(1) A bisimide compound shown by the general formula [1]:

$$RO-N\overset{\underset{O}{\|}}{\underset{\underset{O}{\|}}{C}}\overset{}{\underset{}{A_1}}\overset{\underset{O}{\|}}{\underset{\underset{O}{\|}}{C}}N-OR \quad [1]$$

[wherein two Rs are each independently a hydrogen atom or a group shown by the general formula [2]:

$$-SO_2R^1 \quad [2]$$

(wherein $R^1$ is an alkyl group having 1 to 12 carbon atoms, a haloalkyl group having 1 to 12 carbon atoms, or an aryl group, an aralkyl group or an aromatic heterocyclic group, which may have a substituent selected from the group consisting of a halogen atom, an alkyl group, a lower haloalkyl group, an alkoxy group, a lower haloalkoxy group, a lower alkenyl group, a nitro group, an N,N-dimethylamino group and an acetamide group, a camphor group or a naphthoquinonediazide group); $A_1$ is a tetra-valent alicyclic hydrocarbon group having 4 to 10 carbon atoms, a tetra-valent bridged alicyclic hydrocarbon group having 7 to 8 carbon atoms, a tetra-valent aromatic hydrocarbon group having 6 to 14 carbon atoms or a group shown by the general formula [3]:

[3]

(wherein $A_2$ is a direct-linkage, an —O— group or a —C(CF$_3$)$_2$— group), and provided that $A_1$ is a group shown by the general formula [3] when R is a hydrogen atom, an alkyl group shown by $R^1$ in the general formula [2] is one having 6 to 12 carbon atoms when $A_1$ is a tetra-valent bridged alicyclic hydrocarbon group having 7 to 8 carbon atoms, and one having 3 to 12 carbon atoms when $A_1$ is a tetra-valent aromatic hydrocarbon group having 6 to 14 carbon atoms; and a haloalkyl group shown by $R^1$ is one having 3 to 12 carbon atoms when $A_1$ is a group shown by the general formula [3]; and further an alkyl group as a substituent of an aryl group which may have a substituent, shown by $R^1$ is one having 2 to 12 carbon atoms when $A_2$ in the general formula [3] is an —O— group].

(2) An acid generator for a chemically amplified resist comprising said bisimide compound, wherein R is one shown by the general formula; [2].

(3). A positive resist composition comprising at least one or more kinds of said bisimide compound, wherein R is one shown by the general formula [2].

(4) A negative resist composition comprising at least one or more kinds of said bisimide compound, wherein R is one shown by the general formula [2].

(5) A method for pattern formation comprising:
a process of forming a positive resist composition in the said (3) on a substrate as a resist film;
a process of exposing an arbitrary pattern on the said resist film; and
a process of forming a positive resist pattern by developing.

(6) A method for pattern formation comprising:
a process of forming a negative resist composition in the said (4) on a substrate as a resist film;
a process of exposing an arbitrary pattern on the said resist film; and
a process of forming a negative resist pattern by developing.

The present inventors have conducted extensive study in order to realize the object mentioned above to arrive at the finding that a bisimide compound, wherein R in the above-described general formula [1] is a group shown by the general formula [2], can be an acid generator having excellent effects of, for example, high acid generation efficiency and high solubility in a resist solvent, and also a raw material and a cross-linking agent for a heat resistant resin such as polyimide, and furthermore, a bis (N-hydroxy)phthalimide compound, wherein R in the above-described general formula [1] is a hydrogen atom, can be a synthetic intermediate for a bisimide compound useful as the said acid generator, a raw material and a cross-linking agent for a heat resistant resin such as polyimide, and an intermediate of a functional compound such as photosensitive material, and finally the present invention has been completed on the basis of these findings.

BRIEF DESCRIPTION OF THE DRAWINGS

FIG. 4 is a cross-sectional view showing each processes of a method of pattern formation using a conventional resist composition (Comparative Example 9).

BEST MODE FOR CARRYING OUT THE INVENTION

Figure 1:
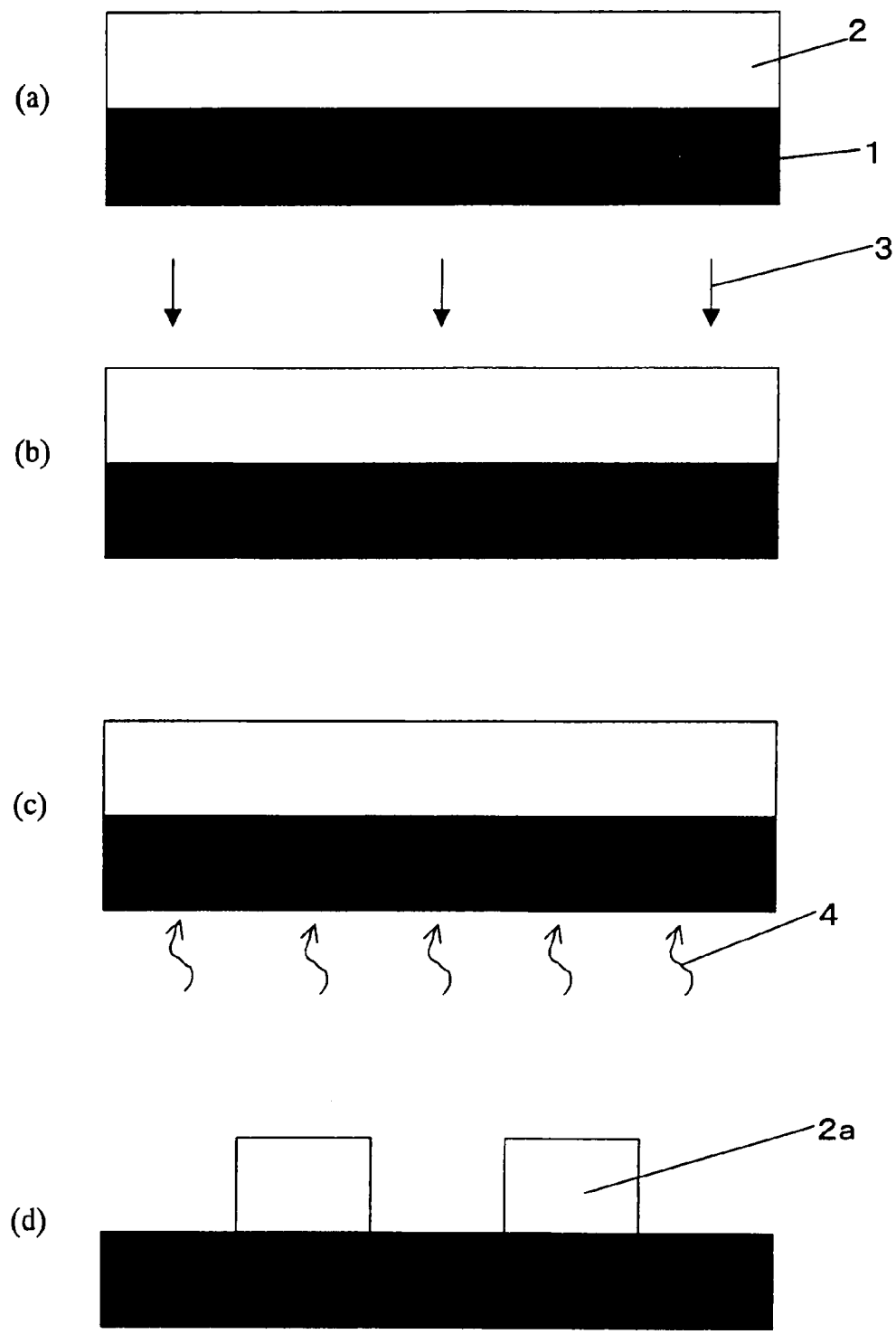
FIG. 1 is a cross-sectional view showing each process of a method of pattern formation using a resist composition of the present invention (Example 67).

In the general formula [2], the alkyl group having 1 to 12 carbon atoms shown by $R^1$ may be straight chained, branched or cyclic, and includes one having preferably 1 to 10 carbon atoms and more preferably 6 to 8carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 1,2-dimethylbutyl group, a 1-ethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl, group, a tert-decyl group, a neodecyl group, an undecyl group, an isoundecyl group, a sec-undecyl group, a tert-undecyl group, a neoundecyl group, a n-dodecyl group, an is ododecyl group, a sec-dodecyl group, a tert-dodecyl group, a neododecyl group, a cyclopropyl group, a cyclobutyl group, a cyclopentyl group, a cyclohexyl group, a cyclohexylmethyl group, a 2-cyclohexylethyl group, a cycloheptyl group, a cyclooctyl group, a cyclononyl group, a cyclodecyl group, a cycloundecyl group and a cyclododecyl group, and among others, a preferable one includes, for example, a methyl group, an ethyl group, a n-propyl group, an isopropyl group, a n-butyl group, a sec-butyl group, a tert-butyl group, a n-pentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group, a n-nonyl group, a sec-nonyl group, a tert-nonyl group, a n-decyl group, a sec-decyl group, a tert-decyl group, a cyclopentyl group and a cyclohexyl group, and a more preferable one includes, for example, a n-hexyl group, n-heptyl group and n-octyl group.

The alkyl group having 6 to 12 carbon atoms shown by $R^1$ in the general formula [2], when $A_1$ in the general formula [1] is a tetra-valent bridged alicyclic hydrocarbon group having 7 to 8 carbon atoms, may be straight chained, branched or cyclic, and includes one having preferably 6 to 8 carbon atoms, which is specifically exemplified by the same as examples of one having 6 to 12 carbon atoms among the alkyl groups having 1 to 12 carbon atoms, shown by $R^1$ in the above-described general formula [2], and among others, a preferable one includes, for example, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-hexyl group, a n-heptyl group and a n-octyl group.

The alkyl group having 3 to 12 carbon atoms shown by $R^1$ in the general formula [2], when $A_1$ in the general formula [1] is a tetra-valent aromatic hydrocarbon group having 6 to 14 carbon atoms, may be straight chained, branched or cyclic, and includes one having preferably 6 to 8 carbon atoms, which is specifically exemplified by the same as examples of one having 3 to 12 carbon atoms among the alkyl groups having 1 to 12 carbon atoms, shown by $R^1$ in the above-described general formula [2], and among others, a preferable one includes, for example, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and amore preferable one includes, for example, a n-hexyl group, a n-heptyl group and a n-octyl group.

The haloalkyl group having 1 to 12 carbon atoms shown by $R^1$ includes one, wherein a part of or all of the hydrogen atoms, preferably 1 to 17 hydrogen atoms and more preferably 7 to 17 hydrogen atoms of the alkyl group having 1 to 12 carbon atoms, shown by $R^1$ in the above-described general formula [2] are substituted by a halogen atom (e.g. a fluorine atom, a chlorine atom, a bromine atom and an iodine atom), and includes one having preferably 1 to 8 carbon atoms, more preferably 3 to 8 carbon atoms, which is specifically exemplified by, for example, a fluoromethyl group, a chloromethyl group, a bromomethyl group, an iodomethyl group, a difluoromethyl group, a trifluoromethyl group, a trichloromethyl group, a tribromomethyl group, a triiodomethyl group, a trifluoroethyl group, a trichloroethyl group, a tribromoethyl group, a triiodoethyl group, a pentafluoroethyl group, a pentachloroethyl group, a pentabromoethyl group, a pentaiodoethyl group, a trifluoropropyl group, a heptafluoropropyl group, a heptachloropropyl group, a heptabromopropyl group, a heptaiodopropyl group, a trifluorobutyl group, a nonafluorobutyl group, a nonachlorobutyl group, a nonabromobutyl group, a nonaiodobutyl group, a trifluoropentyl group, an undecafluoropentyl group, an undecachloropentyl group, an undecabromopentyl group, an undecaiodopentyl group, a trifluorohexyl group, a tridecafluorohexyl group, a tridecachlorohexyl group, a tridecabromohexyl group, a tridecaiodohexyl group, a trifluoroheptyl group, a pentadecafluoroheptyl group, a pentadecachloroheptyl group, a pentadecabromoheptyl group, a pentadecaiodoheptyl group, a trifluorooctyl group, a heptadecafluorooctyl group, a heptadecachlorooctyl group, a heptadecabromooctyl group, a heptadecaiodooctyl group, a trifluorononyl group, a nonadecafluorononyl group, a nonadecachlorononyl group, a nonadecabromononyl group, a nonadecaiodononyl group, a trifluorodecyl group, a perfluorodecyl group, a perchlorodecyl group, a perbromodecyl group, a periododecyl group, a perfluoroundecyl group, a perchloroundecyl group, a perbromoundecyl group, a periodoundecyl group, a perfluorododecyl group, a perchlorododecyl group, a perbromododecyl group and a periodododecyl group, and among others, a preferable one includes, for example, a trifluoromethyl group, a nonafluorobutyl group and a heptadecafluorooctyl group, and a more preferable one is a nonafluorobutyl group.

The haloalkyl group having 3 to 12 carbon atoms shown by $R^1$ in the general formula [2], when $A_1$ in the general formula [1this a group shown bythe general formula [3], includes one, wherein a part of or all of the hydrogen atoms, preferably 1 to 17 hydrogen atoms and more preferably 7 to 17 hydrogen atoms of the alkyl group having 3 to 12 carbon atoms among the alkyl groups having 1 to 12 carbon atoms, shown by $R^1$ in the above-described general formula [2] are substituted by a halogen atom (e.g. a fluorine atom, a chlorine atom, a bromine atom and an iodine atom), and includes one having preferably 3 to 8 carbon atoms, which is specifically exemplified by the same as examples of one having 3 to 12 carbon atoms among the haloalkyl groups having 1 to 12 carbon atoms, shown by $R^1$ in the above-described general formula [2], and among others, a preferable one includes, for example, a nonafluorobutyl group and a heptadecafluorooctyl group, and more preferable one is a nonaflubrobutyl group.

The aryl group of the aryl group which may have a substituent, shown by $R^1$ includes one having generally 6 to 16 carbon atoms, preferably 6 to 10 carbon atoms, which is specifically exemplified by, for example, a phenyl group, a 1-naphthyl group, a 2-naphthyl group, an anthryl group and a pyrenyl group, and among others, a phenyl group and a naphthyl group are preferable, and a phenyl group is more preferable.

The aralkyl group of the aralkyl group which may have a substituent, shown by $R^1$ includes one having generally 7to 10 carbon atoms, preferably 7 to 8 carbon atoms, which is specifically exemplified by, for example, a benzyl group, a phenethyl group, a 1-phenylethyl group, a 2-phenylpropyl group, a 3-phenylpropyl group, a phenylbutyl group and a 1-methyl-3-phenylpropyl group, and among others, a benzyl group is preferable.

The aromatic heterocyclic group of the aromatic heterocyclic group which may have a substituent, shown by $R^1$ includes, for example, one having at least one hetero atom, preferably 1 to 3 hetero atoms, such as a nitrogen atom, a sulfur atom and an oxygen atom, and may be a monocyclic or bicyclic one, which is specifically exemplified by, for example, a 2-thienyl group, a 8-quinolyl group, a 5-isoquinolyl group, a 3-pyridyl group, a 2-thiazolyl group, a 2-furfuryl group and a 2-imidazolyl group, and among others, a 2-thienyl group is preferable.

The substituent of an aryl group, an aralkyl group and an aromatic heterocyclic group, which may have a substituent, shown by $R^1$ includes, for example, a halogen atom, an alkyl group, a lower haloalkyl group, an alkoxy group, a lower haloalkoxy group, a lower alkenyl group, a nitro group, a N,N-dimethylamino group and an acetamide group.

The halogen atom as the substituent includes, for example, a fluorine atom, a chlorine atom, a bromine atom and an iodine atom, and among others, a fluorine atom and a chlorine atom are preferable, and a fluorine atom is more preferable.

The alkyl group as the substituent may be straight chained, branched, or cyclic, and includes one having generally 1 to 12 carbon atoms, preferably 1 to 4 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a 2-methylpentyl group, an 1,2-dimethylbutyl group, an 1-ethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group and a cyclohexyl group, and among others, a preferable one includes, for example, a methyl group, an ethyl group, a n-propyl group, an isopropyl group, a n-butyl group, a sec-butyl group and a tert-butyl group, and a more preferable one includes, for example, a methyl group, an ethyl group, a n-propylgroup, a n-butyl group and a tert-butyl group.

The lower haloalkyl group as the substituent includes one, wherein a part of or all of hydrogen atoms of a lower alkyl group having generally 1 to 4 carbon atoms, preferably 1 to 2 carbon atoms are substituted by a halogen atom (e.g. a fluorine atom, a chlorine atom, a bromine atom and an iodine atom), which is specifically exemplified by, for example, a fluoromethyl group, a chloromethyl group, a trifluoromethyl group, a trichloromethyl group, a tribromomethyl group, a triiodomethyl group, a trifluoroethyl group, a trichloroethyl group, a pentafluoroethyl group, a pentachloroethyl group, a pentabromoethyl group, a pentaiodoethyl group, a trifluoropropyl group, a trichloropropyl group, a heptafluoropropyl group, a heptachloropropyl group, a heptabromopropyl group, a heptaiodopropyl group, a trifluorobutyl group, a trichlorobutyl group, a nonafluorobutyl group, a nonachlorobutyl group, a nonabromobutyl group and a nonaiodobutyl group, and among others, a trifluoromethyl group and a pentafluoroethyl group are preferable and a trifluoromethyl group is more preferable.

The alkoxy group as the substituent may be straight chained, branched or cyclic, and includes one having generally 1 to 12 carbon atoms, preferably 1 to 4 carbon atoms, which is specifically exemplified by, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a cyclohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxygroup, a n-undecyloxygroup, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group and a neododecyloxy group, and among others, a methoxy group, an ethoxy group, a n-propoxy group, an isopropoxy group, a n-butoxy group, a sec-butoxy group and a tert-butoxy group are preferable and a methoxy group is more preferable.

The lower haloalkoxy group as the substituent includes one, wherein a part of or all of the hydrogen atoms of an alkoxy group having generally 1 to 4 carbon atoms, preferably 1 to 2 carbon atoms are substituted by a halogen atom (e.g. a fluorine atom, a chlorine atom, a bromine atom and an iodine atom), which is specifically exemplified by, for example, a fluoromethoxy group, a chloromethoxy group, a trifluoromethoxy group, a trichloromethoxy group, a tribromomethoxy group, a triiodomethoxy group, a trifluoroethoxy group, a pentafluoroethoxy group, a pentachloroethoxy group, a pentabromoethoxy group, a pentaiodoethoxy group, a trifluoropropoxy group, a heptafluoropropoxy, group, a heptachloropropoxy group, a heptabromopropoxy group, a heptaiodopropoxy group, a trifluorobutoxy group, a nonafluorobutoxy group, a nonachlorobutoxy group, a nonabromobutoxy group and a nonaiodobutoxy group, and among others, a trifluoromethoxy group is preferable.

The lower alkenyl group as the substituent may be straight chained, branched or cyclic, and includes one having generally 2 to 4 carbon atoms, preferably 2 to 3 carbon atoms, which is specifically exemplified by, for example, a vinyl group, an allyl group, a 1-propenyl group, an isopropenyl group, a 1-butenyl group, a 2-butenyl group and a 2-methylallyl group, and among others, a vinyl group is preferable.

The alkyl group having 1 to 12 carbon atoms as the substituent of the aryl group which may have the substituent, shown by $R^1$ in the general formula [2], when $A_1$ in the general formula [1] is a group shown by the general formula [3], and $A_2$ in the above-described general formula [3] is a direct-linkage or a —$C(CF_3)_2$— group, may be straight chained, branched or cyclic, and includes one having preferably 3 to 8 carbon atoms, which is specifically exemplified by the same as examples of the alkyl group having 1 to 12 carbon atoms shown by $R^1$ in the above-described general formula [2], and among others, a preferable one includes, for example, a n-propyl group, an isopropyl group, a n-butyl group, a sec-butyl group, a tert-butyl group, a n-pentyl group, an isopentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and more preferable one includes, for example, a n-propyl group, an isopropyl group, a n-butyl group, a sec-butyl group and a tert-butyl group.

The alkyl group having 2 to 12 carbon atoms as the substituent of the aryl group which may have a substituent, shown by $R^1$ in the general formula [2], when $A_1$ in the general formula [1] is a group shown by the general formula

[3], and $A_2$ in the general formula [3] is an —O— group, may be straight chained, branched or cyclic, and includes one having preferably 3 to 12 carbon atoms, more preferably 3 to 8 carbon atoms, which is specifically exemplified by the same as examples of one having 2 to 12 carbon atoms among the alkyl groups having 1 to 12 carbon atoms, shown by $R^1$ in the general formula [2], and among others, a preferable one includes, for example, a n-propyl group, an isopropyl group, a n-butyl group, a sec-butyl group, a tert-butyl group, a n-pentyl group, an isopentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-propyl group, an isopropyl group, a n-butyl group, a sec-butyl group and a tert-butyl group.

The alkoxy group as the substituent of the aryl group which has a substituent, shown by $R^1$ in the general formula [2], when $A_1$ in the general formula [1] is a group shown by the general formula [3], may be straight chained, branched or cyclic, and includes one having generally 1 to 12 carbon atoms, preferably 3 to 6 carbon atoms, which is specifically exemplified by the same as examples one of the alkoxy group having 1 to 12 carbon atoms as the substituent of the aryl group, the aralkyl group or the aromatic heterocyclic group, which may have a substituent, shown by $R^1$ in the above-described general formula [2], and among others, a preferable one includes, for example, a n-propoxy group, an isopropoxy group, a n-butoxy group, an isobutoxy group, a sec-butoxy, group, a n-pentyloxy group, a sec-pentyloxy group, a tert-pentyloxy group, a n-hexyloxy group, a sec-hexyloxy group, a tert-hexyloxy group and a cyclohexyloxy group, and a more preferable one includes, for example, a n-propoxy group, an isopropoxy group, a n-butoxy group, a sec-butoxy group and a tert-butoxy group.

Among these substituents, electron-withdrawing groups such as a halogen atom, a trifluoromethyl group and a nitro group is preferable.

The aryl group which may have a substituent, shown by $R^1$ is preferably one having at least one electron-withdrawing group at m-position, which is specifically exemplified by, for example, a m-trifluoromethylphenyl group, a 3,5-di-trifluoromethylphenyl group and a pentafluorophenyl group.

Among these $R^1$s, a preferable one includes, for example, a haloalkyl group, anaryl group or an aromatic heterocyclic group, which may have a substituent and a camphor group, and a more preferable one includes a haloalkyl group, an aryl group which may have a substituent and a camphor group.

The two $R^1$s in the general formula [1] may be different each other, but preferably the same.

In the general formula [1], the tetra-valent alicyclic hydrocarbon group having 4 to 10 carbon atoms, shown by A, includes, for example, a group shown by the general formula [7]:

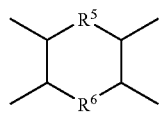

[7]

(wherein $R^5$ and $R^6$ are each independently a direct-linkage or a lower alkylene chain having 1 to 3 carbon-atoms).

The lower alkylene chain having 1 to 3 carbon atoms, shown by $R^5$ and $R^6$ preferably includes a linear alkylene group having 1 to 2 carbon atoms, which is specifically exemplified by, for example, a methylene group, an ethylene group and a trimethylene group, and among others, a methylene group is preferable.

The combination of $R^5$ and $R^6$ includes specifically, for example, one wherein both are direct-linkages (a 4-membered ring); one wherein one is a direct-linkage and the other is a methylene group (a 5-membered ring); and one wherein both are methylene groups (a 6-membered ring).

The bridged alicyclic hydrocarbon group having 7 to 8 carbon atoms, shown by $A^1$ includes, for example, a group shown by the general formula [16]:

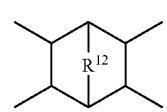

[16]

(wherein $R^{12}$ is a methylene group, an ethylene group or a vinylene group) and among others, a preferable one includes a group shown by the formula [8]:

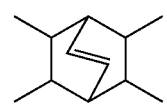

[8]

(corresponding to one wherein $R^{11}$ in the general formula [16] is a vinylene group).

The tetra-valent aromatic hydrocarbon group having 6 to 14 carbon atoms, shown by $A^1$ includes a monocyclic or a polycyclic group obtained by condensation of 2 to 3 rings, which is specifically exemplified by, for example, a group shown by the formula [9],

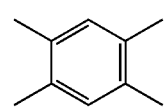

[9]

a group shown by the formula [17],

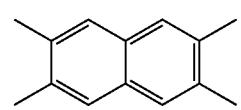

[17]

and a group shown by the formula [18],

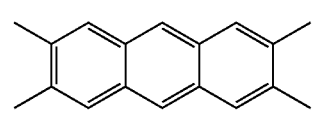

[18]

and among others, a preferable one is a group shown by the above-described general formula [9].

The bisimide compound shown by the above-described general formula [1] includes, for example, a bisimidesulfonate compound shown by the general formula [4]:

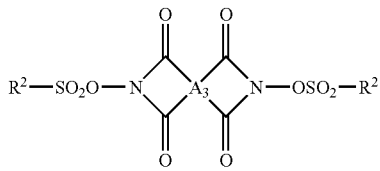

[4]

(wherein $R^2$ is an alkyl group having 1 to 12 carbon atoms, a haloalkyl group having 1 to 12 carbon atoms, or an aryl group, an aralkyl group or an aromatic heterocyclic group, which may have a substituent selected from the group consisting of a halogen atom, an alkyl group, a lower haloalkyl group, an alkoxy group, a lower haloalkoxy group, a lower alkenyl group, a nitro group, an N,N-dimethylamino group and an acetamide group, a camphor group or a naphthoquinonediazide group; $A_3$ is a tetra-valent alicyclic hydrocarbon group having 4 to 10 carbon atoms, a tetra-valent bridged alicyclic hydrocarbon group having 7 to 8 carbon atoms or a tetra-valent aromatic hydrocarbon group having 6 to 14 carbon atoms; and provided that an alkyl group shown by $R^2$ is one having 6 to 12 carbon atoms when $A_3$ is a tetra-valent bridged alicyclic hydrocarbon group having 7 to 8 carbon atoms, and one having 3 to 12 carbon atoms when $A_3$ is a tetra-valent aromatic hydrocarbon group having 6 to 14 carbon atoms); and a bisphthalimide compound shown by the general formula [5]:

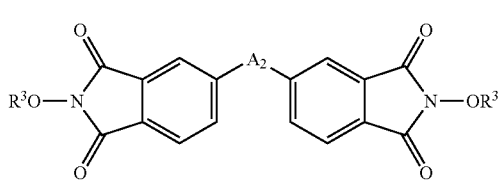

[5]

[wherein two $R^3$s are each independently a hydrogen atom or a group shown by the general formula [6]:

[6]

(wherein $R^4$ is an alkyl group having 1 to 12 carbon atoms, a haloalkyl group having 3 to 12 carbon atoms, or an aryl group, an aralkyl group or an aromatic heterocyclic group, which may have a substituent selected from the group consisting of a halogen atom, an alkyl group, a lower haloalkyl group, an alkoxy group, a lower haloalkoxy group, a lower alkenyl group, a nitro group, an N,N-dimethylamino group and an acetamide group, a camphor group or a naphthoquinonediazide group;); $A_2$ is a direct-linkage, an —O— group or a —$C(CF_3)_2$— group; and provided that an alkyl group as a substituent of an aryl group which may have a substituent, shown by $R^4$ is one having 2 to 12 carbon atoms, when $A_2$ is an —O— group].

The alkyl group having 1 to 12 carbon atoms shown by $R^2$, when $A_3$ in the general formula [4] is a tetra-valent alicyclic hydrocarbon group having 4 to 10 carbon atoms, and an alkyl group having 1 to 12 carbon atoms shown by $R^4$, when $R^3$ in the general formula [5] is a group shown by the general formula [6], may be straight chained, branched or cyclic, and includes one having preferably 1 to 10 carbon atoms, more preferably 6 to 8 carbon atoms, which is specifically exemplified by the same as examples of the alkyl group having 1 to 12 carbon atoms, shown by $R^1$ in the general formula [2], and among others, a preferable one includes, for example, a methyl group, an ethyl group, a n-propyl group, an isopropyl group, a n-butyl group, a sec-butyl group, a tert-butyl group, a n-pentylgroup, a sec-pentyl group, a tert-pentyl group, a n-hexyl group, an isohexyl group, a sec-hexyl group, a tert-hexyl group, a n-heptyl group, a sec-heptyl group, a tert-heptyl group, a n-octyl group, a sec-octyl group, a tert-octyl group, a n-nonyl group, a sec-nonyl group, a tert-nonyl group, a n-decyl group, a sec-decyl group, a tert-decyl group, a cyclopentyl group and a cyclohexyl group, and a more preferable one includes, for example, a n-hexyl group, a n-heptyl group and a n-octyl group.

The alkyl group having 6 to 12 carbon atoms shown by $R^2$, when $A_3$ in thegeneral formula [4] is a tetra-valent bridged alicyclic hydrocarbon group having 7 to 8 carbon atoms, may be straight chained, branched or cyclic, and includes one having preferably 6 to 8 carbon atoms, which is specifically exemplified by the same as examples of one having 6 to 12 carbon atoms among the alkyl groups having 1 to 12 carbon atoms, shown by $R^1$ in the above-described general formula [2], and among others, a preferable one includes, for example, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and among others, a more preferable one is, for example, a n-hexyl group, a n-heptyl group and a n-octyl group.

The alkyl group having 3 to 12 carbon atoms shown by $R^2$, when $A_3$ in the general formula [4] is a tetra-valent aromatic hydrocarbon group having 6 to 14 carbon atoms, may be straight chained, branched or cyclic, and includes one having preferably 6 to 8 carbon atoms, which is specifically exemplified by the same as examples of one having 3 to 12 carbon atoms among the alkyl groups having 1 to 12 carbon atoms, shown by $R^1$ in the general formula [2], and among others, a preferable one includes, for example, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-hexyl group, a n-heptyl group and a n-octyl group.

In the general formula [4], the haloalkyl group having 1 to 12 carbon atoms shown by $R^2$ includes one, wherein a part of or all of the hydrogen atoms, preferably 1 to 17 hydrogen atoms and more preferably 7 to 17 hydrogen atoms of the alkyl group having 1 to 12 carbon atoms shown by $R^1$ in the above-described general formula [2] are substituted by a halogen atom (e.g. a fluorine atom, a chlorine atom, a bromine atom and an iodine atom), includes one having preferably 1 to 8, more preferably 3 to 8 carbon atoms, which is specifically exemplified by the same as examples of the haloalkyl group having 1 to 12 carbon atoms, shown by $R^1$ in the above-described general formula [2], and among others, a preferable one includes, for example, a trifluoromethyl group, a nonafluorobutyl group and a heptadecafluorooctyl group, and a more preferable one is a nonafluorobutyl group.

In the general formula [6], the haloalkyl group having 3 to 12 carbon atoms shown by $R^4$ includes one, wherein a part of or all of the hydrogen atoms, preferably 1 to 17 hydrogen atoms and more preferably 7 to 17 hydrogen atoms of the alkyl group having 3 to 12 carbon atoms, preferably 3 to 8 carbon atoms, among the alkyl groups having 1 to 12 carbon atoms shown by $R^1$ in the above-described general formula [2] are substituted by a halogen atom (e.g. a fluorine atom, a chlorine atom, a bromine atom and an iodine atom) which is specifically exemplified by the same as examples of one having 3 to 12 carbon atoms among the haloalkyl groups having 1 to 12 carbon atoms, shown by $R^1$ in the above-described general formula [2], and among others, a preferable one includes, for example, a nonafluorobutyl group and a heptadecafluorooctyl group, and a more preferable one is a nonafluorobutyl group.

In the general formulae [4] and [6], the aryl group of the aryl group which may have a substituent, shown by $R^2$ and $R^4$ includes one having generally 6 to 16 carbon atoms, preferably 6 to 10 carbon atoms, which is specifically exemplified by the same as examples of the aryl group of the aryl group which may have a substituent, shown by $R^1$ in the general formula [2], and among others, a preferable one includes, for example, a phenyl group and a naphthyl group, and a more preferable one is a phenyl group.

The aralkyl group of the aralkyl group which may have a substituent, shown by $R^2$ and $R^4$, includes one having generally 7 to 10 carbon atoms, preferably 7 to 8 carbon atoms, which is specifically exemplified by the same as examples of the aralkyl group of the aralkyl group which may have a substituent, shown by $R^1$ in the above-described general formula (2), and among others, a benzyl group is preferable.

The aromatic heterocyclic group of the aromatic heterocyclic group which may have a substituent, shown by $R^2$ and $R^4$, includes one having at least 1 hetero atom, preferably 1 to 3 hetero atoms such as a nitrogen atom, a sulfur atom and an oxygen atom, and may be a monocyclic or a bicyclic group, which is specifically exemplified by the same as examples of the aromatic heterocyclic group of the aromatic heterocyclic group which may have a substituent, shown by $R^1$ in the above-described general formula [2], and among others, a preferable one is a 2-thienyl group.

The substituent of the aryl group, the aralkyl group or the aromatic heterocyclic group, which may have a substituent, shown by $R^2$ and $R^4$ includes, for example, a halogen atom, an alkyl group, a lower haloalkyl group, an alkoxy group, a lower haloalkoxy group, a lower alkenyl group, a nitro group, a N,N-dimethylamino group and an acetamide group.

The halogen atom as the substituent includes, for example, a fluorine atom, a chlorine atom, a bromine atom and an iodine atom, and among others, a preferable one includes a fluorine atom and a chlorine atom, and a more preferable one is a fluorine atom.

The alkyl group as the substituent may be straight chained, branched or cyclic, and includes one having generally 1 to 12 carbon atoms, preferably 1 to 4 carbon atoms, which is specifically exemplified by the same as examples of the alkyl group having 1 to 12 carbon atoms, shown by $R^1$ in the above-described general formula [2], and among others, a preferable one includes, for example, a methyl group, an ethyl group, a n-propyl group, an isopropyl group, a n-butyl group, a sec-butyl group and a tert-butyl group, and a more preferable one includes, for example, a methyl group, an ethyl group, a n-propyl group, a n-butyl group and a tert-butyl group.

The lower haloalkyl group as the substituent includes one, wherein a part of or all of hydrogen atoms of the lower alkyl group having generally 1 to 4 carbon atoms, preferably 1 to 2 carbon atoms are substituted by a halogen atom (e.g. a fluorine atom, a chlorine atom, a bromine atom and an iodine atom), which is specifically exemplified by the same as examples of the lower haloalkyl group as the substituent of the aryl group, the aralkyl group or the aromatic heterocyclic group, which may have a substituent, shown by $R^1$ in the above-described general formula [2], and among others, a preferable one includes, for example, a trifluoromethyl group and a pentafluoroethyl group, and a more preferable one is a trifluoromethyl group.

The alkoxy group as the substituent may be straight chained, branched or cyclic, and includes one having generally 1 to 12 carbon atoms, preferably 1 to 4 carbon atoms, which is specifically exemplified by the same as examples of the alkoxy group as the substituent of the aryl group, the aralkyl group or the aromatic heterocyclic group, which may have a substituent, shown by $R^1$ in the above-described general formula [2], and among others, a preferable one includes, for example, a methoxy group, an ethoxy group, a n-propoxy-group, an isopropoxy group, a n-butoxy group, a sec-butoxy group and a tert-butoxy group, and a more preferable one is a methoxy-group.

The lower haloalkoxy group as the substituent includes one, wherein a part of or all of the hydrogen atoms of an alkoxy group having generally 1 to 4 carbon atoms, preferably 1 to 2 carbon atoms are substituted by a halogen atom (e.g. a fluorine atom, a chlorine atom, a bromine atom and an iodine atom), which is specifically exemplified by the same as examples of the lower haloalkoxy group as the substituent of the aryl group, the aralkyl group or the aromatic heterocyclic group, which may have a substituent, shown by $R^1$ in the above-described general formula [2], and among others, a trifluoromethoxy group is preferable.

The lower alkenyl group as the substituent may be straight chained, branched or cyclic, and includes one having generally 2 to 4 carbon atoms, preferably, 2 to 3 carbon atoms, which is specifically exemplified by the same as examples of the lower alkenyl group as the substituent of the aryl group, the aralkyl group or the aromatic heterocyclic group, which may have a substituent, shown by $R^1$ in the above-described general formula [2], and among others, a vinyl group is preferable.

The alkyl group having 1 to 12 carbon atoms, as the substituent of the aryl group which may have a substituent, shown by $R^4$ in the general formula [6], when $R^3$ in the general formula [5] is a group shown by the general formula [6], and $A_2$ is a direct-linkage or a —$C(CF_3)_2$— group, may be straight chained, branched or cyclic, and includes one having preferably 3 to 8 carbon atoms, which is specifically exemplified by the same as examples, of the alkyl group having 1 to 12 carbon atoms, shown by $R^1$ in the above-described general formula [2], and among others, a preferable one includes, for example, a n-propyl group, an iso-propyl group, a n-butyl group, a sec-butyl group, a tert-butyl group, a n-pentyl group, an isopentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-propyl group, an isopropyl group, a n-butyl group, a sec-butyl group and a tert-butyl group.

The alkyl group having 2 to 12 carbon atoms as the substituent of the aryl group which may have a substituent, shown by $R^4$ in the general formula [6], when $R^3$ in the general formula [5] is a group shown by the general formula [6], and $A_2$ is an —O— group, may be straight chained, branched or cyclic, and includes one having preferably 3 to 12 carbon atoms, more preferably 3 to 8 carbon atoms, which is specifically exemplified by the same as examples of the alkyl group having 1 to 12 carbon atoms, shown by $R^1$ in the above-described general formula [2], and among others, a preferable one includes, for example, a n-propyl group, an isopropyl group, a n-butyl group, a sec-butyl group, a tert-butyl group, a n-pentylgroup, an isopentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-propyl group, an isopropyl group, a n-butyl group, a sec-butyl group and a tert-butyl group.

The alkoxy group as the substituent of the aryl group which may have a substituent, shown by $R^4$ in the general formula [6], when $R^3$ in the general formula [5] is a group shown by the general formula [6], may be straight chained, branched or cyclic, includes one having generally 1 to 12 carbon atoms, preferably 3 to 6 carbon atoms, which is specifically exemplified by the same as examples of the alkoxy group having 1 to 12 carbon atoms as the substituent of the aryl group, the aralkyl group or the aromatic heterocyclic group, which may have a substituent, shown by $R^1$ in the above-described general formula [2], and among others, a preferable one includes, for example, a n-propoxy group, an isopropoxy group, a n-butoxy group, an isobutoxy group, a sec-butoxy group, a n-pentyloxy group, a sec-pentyloxy group, a tert-pentyloxygroup, a n-hexyloxy group, a sec-hexyloxy group, a tert-hexyloxy group and a cyclohexyloxy group, and a more preferable one includes, for example, a n-propoxy group, an isopropoxy group, a n-butoxy group, a sec-butoxy group and a tert-butoxy group.

In the general formula [4], the tetra-valent alicyclic hydrocarbon group having 4 to 10 carbon atoms, shown by $A_3$ includes the same as examples of the tetra-valent alicyclic hydrocarbon group having 4 to 10 carbon atoms, shown by $A_1$ in the above-described general formula [1].

The tetra-valent bridged alicyclic hydrocarbon group having 7 to 8 carbon atoms, shown by $A_3$ includes the same as examples of the tetra-valent bridged alicyclic hydrocarbon group having 7 to 8 carbon atoms, shown by $A_1$ in the above-described general formula [1], and among others, the one shown by the above-described formula [8] is preferable.

The tetra-valent aromatic hydrocarbon group having 6 to 14 carbon atoms, shown by $A_3$ includes the same as examples of the tetra-valent aromatic hydrocarbon group having 6 to 14 carbon atoms, shown by $A_1$ in the above-described general formula [1], and among others, the one shown by the above-described general formula [9] is preferable.

The bisimidesulfonate compound, shown by the above-described general formula [4], when $A_1$ is a tetra-valent alicyclic hydrocarbon group having 4 to 10 carbon atom, includes preferably one shown by the general formula [10]:

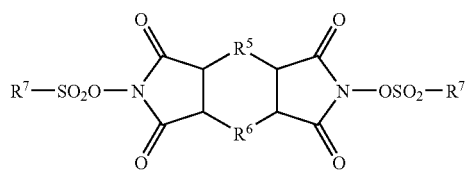

[10]

(wherein $R^7$s are each independently an alkyl group having 1 to 12 carbon atoms, a haloalkyl group having 1 to 12 carbon atoms, or an aryl group, an aralkyl group or an aromatic heterocyclic group, which may have a substituent selected from the group consisting of a halogen atom, an alkyl group, a lower haloalkyl group, an alkoxy group, a lower haloalkoxy group, a lower alkenyl group, a nitro group, an N,N-dimethylamino group and an acetamide group, a camphor group or a naphthoquinonediazide group; $R^5$ and $R^6$ are the same as described above) and the like, and when $A_1$ is a tetra-valent bridged alicyclic hydrocarbon group having 7 to 8 carbon atoms, includes preferably one shown by the general formula [11]:

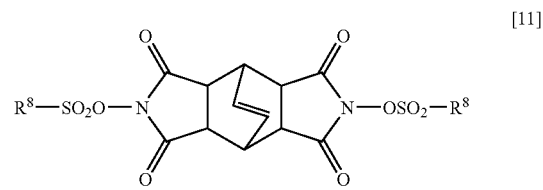

[11]

(wherein $R^8$ is an alkyl group having 6 to 12 carbon atoms, a haloalkyl group having 1 to 12 carbon atoms, or an aryl group, an aralkyl group or an aromatic heterocyclic group, which may have a substituent selected from the group consisting of a halogen atom, an alkyl group, a lower haloalkylgroup, an alkoxy group, a lower haloalkoxy group, a lower alkenyl group a nitro group, an N,N-dimethylamino group and an acetamide group, a camphor group or a naphthoquinonediazide group) and the like, and further when $A_1$ is a tetra-valent aromatic hydrocarbon group, includes preferably one shown by the general formula [12]:

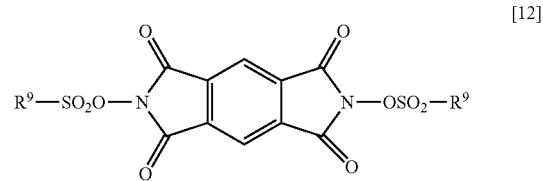

[12]

(wherein $R^9$ is an alkyl group having 3 to 12 carbon atoms, a haloalkyl group having 1 to 12 carbon atoms, or an aryl group, an aralkyl group or an aromatic heterocyclic group, which may have a substituent selected from the group consisting of a halogen atom, an alkyl group, a lower haloalkyl group, an alkoxy group, a lower haloalkoxy group, a lower alkenyl group, a nitro group, an N,N-dimethylamino group and an acetamide group, a camphor group or a naphthoquinonediazide group) and the like.

In the general formula [10], the alkyl group having 1 to 12 carbon atoms, shownby $R^7$ may be straight chained, branched or cyclic, and includes one having generally 1 to 10 carbon atoms, preferably 6 to 8 carbon atoms, which is specifically exemplified by the same as examples of the alkyl group having 1 to 12 carbon atoms, shown by $R^1$ in the above-described general formula [2], and among others, a preferable one includes, for example, a methyl group, an ethyl group, a n-propyl group, an isopropyl group, a n-butyl group, a sec-butyl group, a tert-butyl group, a n-pentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group, a n-nonyl group, a sec-nonyl group, a tert-nonyl group, a n-decyl group, a sec-decyl group, a tert-decyl group, a cyclopentyl group and a cyclohexyl group, and among others, a more preferable one includes, for example, a n-hexyl group, a n-heptyl group and a n-octyl group.

In the general formula [11], the alkyl group having 6 to 12 carbon atoms, shown by $R^8$ may be straight, chained, branched or cyclic, and includes one having preferably 6 to 8 carbon atoms, which is specifically exemplified by the same as examples of one having 6 to 12 carbon atoms among the alkyl groups having 1 to 12 carbon atoms, shown by $R^1$ in the above-described general formula [2], and among others, a preferable one includes, for example, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-hexyl group, a n-heptyl group and a n-octyl group.

In the general formula [12], the alkyl group having 3 to 12 carbon atoms, shown by $R^9$ may be straight chained, branched or cyclic, and includes one having preferably 6to 8 carbon atoms, which is specifically exemplified by the same as examples of one having 3 to 12 carbon atoms among the alkyl groups having 1 to 12 carbon atoms, shown by $R^1$ in the above-described general formula [2], and among others, a preferable one includes, for example, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-hexyl group, a n-heptyl group and a n-octyl group.

In the general formulae (10) to [12], the haloalkyl group having 1 to 12 carbon atoms, shown by $R^7$ to $R^9$ includes one, wherein a part of or all of the hydrogen atoms, preferably 1 to 17 hydrogen atoms and more preferably 7 to 17 hydrogen atoms of the alkyl group having 1 to 12 carbon atom, shown by $R^1$ in the above-described general formula [2] are substituted by a halogen atom (e.g. a fluorine atom, a chlorine atom, a bromine atom and an iodine atom), one having preferably 1 to 8 carbon atoms, more preferably 3 to 8 carbon atoms, which is specifically exemplified by the same as examples of the haloalkyl group having 1 to 12 carbon atoms, shown by $R^1$ in the above-described general formula [2], and among others, a preferable one includes, for example, a trifluoromethyl group, a nonafluorobutyl group and a heptadecafluorooctyl group, and a more preferable one is a nonafluorobutyl group.

The aryl group of the aryl group which may have a substituent, shown by $R^7$ to $R^9$, includes one having generally 6 to 16 carbon atoms, preferably 6 to 10 carbon atoms, which is specifically exemplified by the same as examples of the aryl group of the aryl group which may have a substituent, shown by $R^1$ in the above-described general formula [2], and among others, a preferable one includes, for example, a phenyl group and a naphthyl group, and a phenyl group is more preferable.

The aralkyl group of the aralkyl group which may have a substituent, shown by $R^7$ to $R^9$, includes one having generally 7 to 10 carbon atoms, preferably 7 to 8 carbon atoms, which is specifically exemplified by the same as examples of the aralkyl group of the aralkyl group which may have a substituent, shown by $R^1$ in the above-described general formula [2], and among others, a benzyl group is preferable.

The aromatic heterocyclic group of the aromatic heterocyclic group which may have a substituent, shown by $R^7$ to $R^9$, includes one having at least 1 hetero atom, preferably 1 to 3 hetero atoms such as a nitrogen atom, a sulfur atom and an oxygen atom, and may be a monocyclic or a bicyclic group, which is specifically exemplified by the same as examples of the aromatic heterocyclic group of the aromatic heterocyclic group which may have a substituent, shown by $R^1$ in the above-described general formula [2], and among others, a preferable one is a 2-thienyl group.

The substituent of the aryl group, the aralkyl group or the aromatic heterocyclic group, which may have a substituent, shown by $R^7$ to $R^9$ includes, for example, a halogen atom, an alkyl group, a lower haloalkyl group, an alkoxy group, a lower haloalkoxy group, a lower alkenyl group, a nitro group, a N,N-dimethylamind group and an acetamide group.

The halogen atom as the substituent includes, for example, a fluorine atom, a chlorine atom, a bromine atom and an iodine atom, and among others, a preferable one includes a fluorine atom and a chlorine atom, and a fluorineatom is more preferable.

The alkylgroup as the substituent maybe straight chained, branched or cyclic, and includes one having generally 1 to 12 carbon atoms, preferably 1 to 4 carbon atoms, which is specifically exemplified by the same as examples of the alkyl group as the substituent of the aryl group, the aralkyl group or the aromatic heterocyclic group, which may have a substituent, shown by $R^1$ in the above-described general formula [2], and among others, a preferable one includes, for example, a methyl group, an ethyl group, a n-propyl group, an isopropyl group, a n-butyl group, a sec-butyl group and a tert-butyl group, and a more preferable one includes, for example, a methyl group, an ethyl group, a n-propyl group, a n-butyl group and a tert-butyl group.

The lower haloalkyl group as the substituent includes one, wherein a part of or all of hydrogen atoms of the lower alkyl group having generally 1 to 4 carbon atoms, preferably 1 to 2 carbon atoms are substituted by a halogen atom (e.g. a fluorine atom, a chlorine atom; a bromine atom and an iodine atom), which is specifically exemplified by the same as examples of the lower haloalkyl group as the subst.ituent of the aryl group, the aralkyl group or the aromatic heterocyclic group, which may have a substituent, shown by $R^1$ in the general formula [2], and among others, a preferable one includes, for example, a trifluoromethyl group and a pentafluoroethyl group, and a trifluoromethyl group is more preferable.

The alkoxy group as the substituent may be straight chained, branched or cyclic, and includes one having generally 1 to 12 carbon atoms, preferably 1 to 4 carbon atoms, which is specifically exemplified by the same as examples of the alkoxy group as the substituent of the aryl group, the aralkyl group or the aromatic heterocyclic group, which may have a substituent, shown by $R^1$ in the above-described general formula [2], and among others, a preferable one includes, for example, a methoxy group, an ethoxy group, a n-propoxy group, an isopropoxy group, a n-butoxy group, a sec-butoxy group and a tert-butoxy group, and a methoxy group is more preferable.

The lower haloalkoxy group as the substituent includes one, wherein a part of or all of the hydrogen atoms of an alkoxy group having generally 1 to 4 carbon atoms, preferably 1 to 2 carbon atoms are substituted by a halogen atom (e.g. a fluorine atom, a chlorine atom, a bromine atom and an iodine atom), which is specifically exemplified by the same as examples of the lower haloalkoxy group as the substituent of the aryl group, the aralkyl group or the aromatic heterocyclic group, which may have a substituent, shown by $R^1$ in the above-described general formula [2], and among others, a trifluoromethoxy group is preferable.

The lower alkenyl group as the substituent may be straight chained, branched or cyclic, and includes one having generally 2 to 4 carbon atoms, preferably2 to 3 carbon atoms, which is specifically exemplified by the same as examples of the lower alkenyl group as the substituent of the aryl group, the aralkyl group or the aromatic heterocyclic group, which may have a substituent, shown by $R^1$ in the above-described general formula [2], and among others, a vinyl group is preferable.

The two $R^7$s to $R^9$s in the general formulae [10] to [12] may be different, but are preferably the same.

Among these $R^7$s to $R^9$s, a preferable one includes, for example, a haloalkyl group, an aryl group or an aromatic heterocyclic group which may have a substituent, and a camphor group, and a more preferable one includes a haloalkyl group, an aryl group which may have a substituent and a camphor group.

In the general formula [10], the aliphatic ring comprising $R^5$ and $R^6$ includes, for example, a cyclobutane ring, a cyclopentane ring, a cyclohexane ring, a cycloheptane ring and a cyclooctane ring, and among others, a preferable one includes a cyclobutane ring and a cyclopentane ring.

The bisphthalimide compound shown by the above-described general formula [5] includes, when $R^3$ is a hydrogen atom, preferably a bis(N-hydroxy) phthalimide compound shown by the general formula [25]:

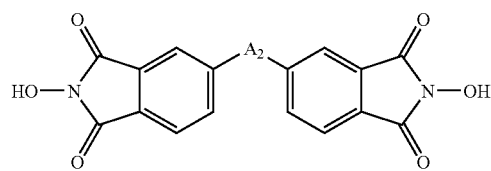

[25]

(wherein $A_2$ is the same as described above) and the like, and when $R^3$ is a group shown by the generalformula [6], preferably a bisphthalimidesulfonate compound, shown by the general formula [26]:

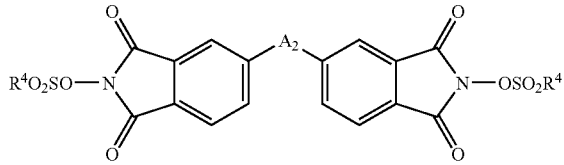

[26]

(wherein definitions of $R^4$, $A_2$ and others are the same as described above) and the like.

The bisphthalimidesulfonate compound shown by the above-described general formula [26] includes, when $A_2$ is an —O— group, one shown by the general formula [13]:

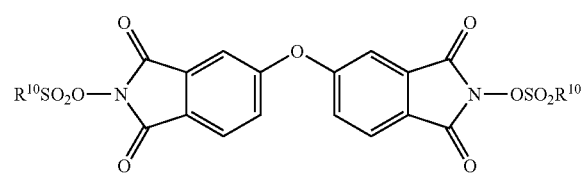

[13]

(wherein $R^{10}$S are each independently an alkyl group having 1 to 12 carbon atoms, a haloalkyl.group having 3 to 12 carbon atoms, an aryl group which may have a substituent selected from the group consisting of a halogen atom, an alkyl group having 2 to 12 carbon atoms, a lower haloalkyl group, an alkoxy group, a lower haloalkoxy group, a lower alkenyl group, a nitro group, an N,N-dimethylamino group and an acetamide group, an aralkyl group or an aromatic heterocyclic group, which may have a substituent selected from the group consisting of a halogen atom, an alkyl group, a lower haloalkyl group, an alkoxy group, a lower haloalkoxy group, a lower alkenyl group, a nitro group, an N,N-dimethylamino group and an acetamide group, a camphor group or a naphthoquinonediazide group), and when $A_2$ is a —C(CF$_3$)$_2$— group, one shown by the general formula [14]:

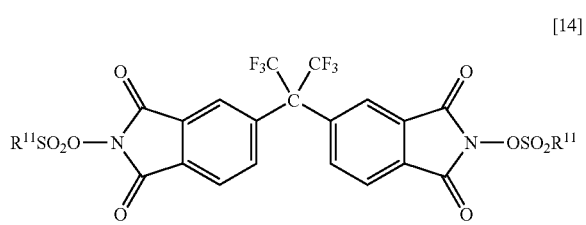

[14]

(wherein $R^{11}$s are each independently an alkyl group having 1 to 12 carbon atoms, a haloalkyl group having 3 to 12 carbon atoms, or an aryl group, an aralkyl group or an aromatic heterocyclic group, which may have a substituent selected from the group consisting of a halogen atom, an alkyl group, a lower haloalkyl group, an alkoxy group, a lower haloalkoxy group, a lower alkenyl group, a nitro group, an N,N-dimethylamirio group and an acetamide group, a camphor group or a naphthoquinonediazide group), and further, when $A_2$ is a direct-linkage, one shown by the general formula [15]:

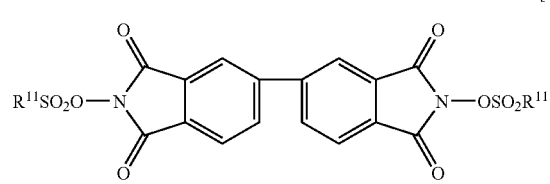

[15]

(wherein $R^{11}$s are the same as described above).

In the general formulae [13] to [15], the alkyl group having 1 to 12 carbon atoms, shown by $R^{10}$ to $R^{11}$ may be straight chained, branched or cyclic, and includes one having preferably 1 to 10 carbon atoms, more preferably 6 to 8 carbon atoms, which is specifically exemplified by the same as examples of the alkyl group having 1 to 12 carbon atoms, shown by $R^1$ in the general formula [2], and among others, apreferable one includes, for example, a methyl group, an ethyl group, a n-propyl group, an isopropyl group, a n-butyl group, a sec-butyl group, a tert-butyl group, a n-pentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group, a n-nonyl group, a sec-nonyl group, a tert-nonyl group, a n-decyl group, a sec-decyl group, a tert-decyl group, a cyclopentyl group and a cyclohexyl group, and a more preferable one includes, for example, a n-hexyl group, a n-heptyl group and a n-octyl group.

In the general formulae [13] to [15], the haloalkyl group having 3 to 12 carbon atoms, shown by $R^{10}$ and $R^{11}$ includes one, wherein a part of or all of the hydrogen-atoms, preferably 1 to 17 hydrogen atoms and more preferably 7 to 17 hydrogen atoms of the alkyl group having 3 to 12 carbon atoms, preferably the one having 3 to 8 carbon atoms, among the alkyl groups having 1 to 12 carbon atoms, shown by $R^1$ in the above-described general formula [2], are substituted by a halogen atom (e.g. a fluorine atom, a chlorine atom, a bromine atom and an iodine atom), which is specifically exemplified by the same as examples of one having 3 to 12 carbon atoms among the haloalkyl groups having 1 to 12 carbon atoms, shown by $R^1$ in the general formula [2], and among others, a preferable one includes, for example, a nonafluorobutyl group and a heptadecafluorooctyl group, and a more preferable one is a nonafluorobutyl group.

The aryl group of the aryl group which may have a substituent, shown by $R^{10}$ and $R^{11}$ includes one having generally 6 to 16 carbon atoms, preferably 6 to 10 carbon atoms, which is specifically exemplified by the same as examples of the aryl group of the aryl group which may have a substituent, shown by $R^1$ in the above-described general formula [2], and among others, a preferable one includes, for example, a phenyl group and a naphthyl group, and a phenyl group is more preferable.

The aralkyl group of the aralkyl group which may have a substituent, shown by $R^{10}$ and $R^{11}$ includes one having generally 7 to 10 carbon atoms, preferably 7 to 8 carbon atoms, which is specifically exemplified by the same as examples of the aralkyl group of the aralkyl group which may have a substituent, shown by $R^1$ in the above-described general formula [2], and among others, a preferable one is a benzyl group.

The aromatic heterocyclic group of the aromatic heterocyclic group which may have a substituent, shown by $R^{10}$ and $R^{11}$ includes one having at least 1 hetero atom, preferably 1 to 3 hetero atoms such as a nitrogen atom, a sulfur atom and an oxygen atom, and may be a monocyclic or a bicyclic group, which is specifically exemplified by the same as examples of the aromatic heterocyclic group of the aromatic heterocyclic group which may have a substituent, shown by $R^1$ in the above-described general formula [2], and among others, a preferable one is a 2-thienyl group.

The substituent of the aryl group, the aralkyl group or the aromatic heterocyclic group, which may have a substituent, shown by $R^{10}$ and $R^{11}$ includes, for example, a halogen atom, an alkyl group, a lower haloalkyl group, an alkoxy group, a lower haloalkoxy group, a lower alkenyl group, a nitro group, a N,N-dimethylamino group and an acetamide group.

The halogen atom as the substituent includes, for example, a fluorine atom, a chlorine atom, a bromine atom and an iodine atom, and among others, a preferable one includes, for example, a fluorine atom and a chlorine atom, and a fluorine atom is more preferable.

The alkyl group having 2 to 12 carbon atoms as the substituent of the aryl group which may have a substituent, shown by $R^{10}$, may be straight chained, branched or cyclic, and is not particularly limited as long as ithas high solubility in a solvent, and includes one having preferably 3 to 12 carbon atoms, more preferably 3 to 8 carbon atoms, which is specifically exemplified by the same as examples of one having 2 to 12 carbon atoms, among the alkyl groups having 1 to 12 carbon atoms, shown by $R^1$ in the above-described general formula [2], and among others, a preferable one includes, for example, a n-propyl group, an isopropyl group, a n-butyl group, a sec-butyl group, a tert-butyl group, a n-pentyl group; an isopentyl group, a sec-pentyl group, a tert-pentyl group, a n-hexyl group, a sec-hexyl group, a tert-hexyl group, a n-heptyl group, a sec-heptyl group, a tert-heptyl group, a n-octyl group, a sec-octyl group, a tert-octyl group and a cyclohexyl group, and a more preferable one includes, for example, a n-propyl group, an isopropyl group, a n-butyl group, a sec-butyl group and a tert-butyl group.

The alkyl group as the substituent of an aryl group which may have a substituent, shown by $R^{11}$, and the aralkyl group or the aromatic heterocyclic group, which may have a substituent, shown by $R^{10}$ and $R^{11}$, may be straight chained, branched or cyclic, and includes one having generally 1 to 12 carbon atoms, preferably 3 to 8 carbon atoms, which is specifically exemplified by the same as examples of the alkyl group having 1 to 12 carbon atoms, shown by $R^1$ in the above-described general formula [2], and among others, a preferable one includes, for example, a n-propyl group, an isopropyl group, a n-butyl group, a sec-butyl group, a tert-butyl group, a n-pentyl group, an isopentyl group, a sec-pentyl group, a tert-pentyl group, a n-hexyl group, a sec-hexyl group, a tert-hexyl group, a cyclohexyl group, a n-heptyl group, a sec-heptyl group, a tert-heptyl group, a n-octyl group, a sec-octyl group and a tert-octyl group, and a more preferable one includes, for example, a n-propyl group, an isopropyl group, a n-butyl group, a sec-butyl group and a tert-butyl group.

The lower haloalkyl group as the substituent of the aryl group, the aralkyl group or the aromatic heterocyclic group, which may have a substituent, shown by $R^{10}$ and $R^{11}$ includes one, wherein a part of or all of the hydrogen atoms of the lower alkyl group having generally 1 to 4 carbon atoms, preferably 1 to 2 carbon atoms are substituted by a halogen atom (e.g. a fluorine atom, a chlorine atom, a bromine atom and an iodine atom), which is specifically exemplified by the same as examples of the lower haloalkyl group as the substituent of the aryl group which may have a substituent, shown by $R^1$ in the above-described general formula [2], and among others, a preferable one is a trifluoromethyl group.

The alkoxy group as the substituent of the aryl group, the aralkyl group or the aromatic heterocyclic group, which may have a substituent, shown by $R^{10}$ and $R^{11}$ may be straight chained, branched or cyclic, and includes one having generally 1 to 12 carbon atoms, preferably 3 to 6 carbon atoms, which is specifically exemplified by the same as examples of the alkoxy group as the substituent of the aryl group which may have a substituent, shown by $R^1$ in the above-described general formula [2], and among others, a preferable one includes, for example, a n-propoxy group, an isopropoxy group, a n-butoxy group, a sec-butoxy group and a tert-butoxy group.

The lower haloalkbxy group as the substituent of the aryl group, the aralkyl group or the aromatic heterocyclic group which may have a substituent, shown by $R^{10}$ and $R^{11}$ includes one, wherein a part of or all of the hydrogen atoms of the alkoxy group having generally 1 to 4 carbon atoms, preferably 1 to 2 carbon atoms are substituted by a halogen atom (e.g. a fluorine atom, a chlorine atom, a bromine atom and an iodine atom), which is specifically exemplified by the same as examples of the lower haloalkoxy group as the substituent of the aryl group which may have a substituent, shown by $R^1$ in the above-described general formula [2], and among others, a trifluoromethoxy group is preferable.

The lower alkenyl group as the substituent of the aryl group, the aralkyl group or the aromatic heterocyclic group, which may have a substituent, shown by $R^{10}$ and $R^{11}$ may be straight chained, branched or cyclic, and includes one having generally 2 to 4 carbon atoms, preferably 2 to 3 carbon atoms, which is specifically exemplified by the same as examples of the lower alkenyl group as the substituent of the aryl group which may have a substituent, shown by $R^1$ in the above-described general formula [2], and among others, a vinyl group is preferable.

Among these substituents, an electron-withdrawing group such as a halogen atom, a trifluoromethyl group and a nitro atom is preferable.

The aryl group which may have a substituent, shown by $R^{10}$ and $R^{11}$ is preferably one having at least one electron-withdrawing group at m-position or p-position, and among others, one having an electron-withdrawing group at m-position is more preferable, which is specifically exemprified by, for example, a m-trifluoromethylphenyl group, a p-trifluoromethylphenyl group, a 3,5-ditrifluoromethylphenyl group and a pentafluorophenyl group.

Among these $R^{10}$ and $R^{11}$, a preferable one includes, for example, a haloalkyl group, an aryl group which may have a substituent, an aromatic heterocyclic group which may have a substituent and a camphor group, and among others, a more preferable one includes, a haloalkyl group, an aryl group which may have a substituent and a camphor group.

The two $R^{10}$ and $R^{11}$ in the general formulae [13] to [15] are may be different, but preferably the same.

The specific examples among the compounds shown by the general formula [10], wherein an aliphatic ring is a cyclobutane ring, include, for example, tetrahydro-2,5-bis(methanesulfonyloxy)cyclobuta[1,2-c:3,4-c']dipyrrole-1,3,4,6(2H,5H)-tetrone, tetrahydro-2,5-bis(ethanesulfonyloxy)cyclobuta[1,2-c:3,4-c']dipyrrole-1,3,4,6(2H,5H)-tetrone, tetrahydro-2,5-bis(n-propanesulfonyloxy)cyclobuta[1,2-c:3,4-c']dipyrrole-1,3,4,6(2H,5H)-tetrone, tetrahydro-2,5-bis(isopropanesulfonyloxy)cyclobuta[1,2-c:3,4-c']dipyrrole-1,3,4,6(2H,5H)-tetrone, tetrahydro-2,5-bis(n-butanesulfonyloxy)cyclobuta[1,2-c:3,4-c']dipyrrole-1,3,4,6(2H,5H)-tetrone, tetrahydro-2,5-bis(n-octanesulfonyloxy)cyclobuta[1,2-c:3,4-c']dipyrrole-1,3,4,6(2H,5H)-tetrone, tetrahydro-2,5-bis(cyclohexylsulfonyloxy)cyclobuta[1,2-c:3,4-c']dipyrrole-1,3,4,6(2H,5H)-tetrone, tetrahydro-2,5-bis(decanesulfonyloxy)cyclobuta[1,2-c:3,4-c']dipyrrole-1,3,4,6(2H,5H)-tetrone, tetrahydro-2,5-bis(trichloromethanesulfonyloxy)cyclobuta[1,2-c:3,4-c']dipyrrole-1,3,4,6(2H,5H)-tetrone, tetrahydro-2,5-bis(trifluoromethanesulfonyloxy)cyclobuta[1,2-c:3,4-c']dipyrrole-1,3,4,6(2H,5H)-tetrone, tetrahydro-2,5-bis(2,2,2-trifluoroethanesulfonyloxy)cyclobuta[1,2-c:3,4-c']dipyrrole-1,3,4,6(2H,5H)-tetrone, tetrahydro-2,5-bis(nonafluorobutanesulfonyloxy)cyclobuta[1,2-c:3,4-c']dipyrrole-1,3,4,6(2H,5H)-tetrone, tetrahydro-2,5-bis(heptadecafluorooctanesulfonyloxy)cyclobuta[1,2-c:3,4-c']dipyrrole-1,3,4,6(2H,5H)-tetrone, tetrahydro-2,5-bis(10-camphorsulfonyloxy)cyclobuta[1,2-c:3,4-c']dipyrrole-1,3,4,6(2H,5H)-tetrone, tetrahydro-2,5-bis(2-thiophenesulfonyloxy)cyclobuta[1,2-c:3,4-c']dipyrrole-1,3,4,6(2H,5H)-tetrone, tetrahydro-2,5-bis(benzylsulfonyloxy)cyclobuta[1,2-c:3,4-c']dipyrrole-1,3,4,6(2H,5H)-tetrone, tetrahydro-2,5-bis(phenylsulfonyloxy)cyclobuta[1,2-c:3,4-c']dipyrrole-1,3,4,6(2H,5H)-tetrone, tetrahydro-2,5-bis(4-methylphenylsulfonyloxy)cyclobuta[1,2-c:3,4-c']dipyrrole-1,3,4,6(2H,5H)-tetrone, tetrahydro-2,5-bis(4-ethylphenylsulfonyloxy)cyclobuta[1,2-c:3,4-c']dipyrrole-1,3,4,6(2H,5H)-tetrone, tetrahydro-2,5-bis(2,5-dimethylphenylsulfonyloxy)cyclobuta[1,2-c:3,4-c']dipyrrole-1,3,4,6(2H,5H)-tetrone, tetrahydro-2,5-bis(2,4,6-trimethylphenylsulfonyloxy)cyclobuta[1,2-c:3,4-c'] dipyrrole-1,3,4,6(2H,5H)-tetrone, tetrahydro-2,5-bis(4-ethenylphenylsulfonyloxy)cyclobuta[1,2-c:3,4-c']dipyrrole-1,3,4,6(2H,5H)-tetrone, tetrahydro-2,5-bis(4-methoxyphenylsulfonyloxy)cyclobuta[1,2-c:3,4-c'] dipyrrole-1,3,4,6(2H,5H)-tetrone, tetrahydro-2,5-bis(4-dodecylbenzenesulfonyloxy)cyclobuta[1,2-c:3,4-c'] dipyrrole-1,3,4,6(2H,5H)-tetrone, tetrahydro-2,5-bis(3,4-dimethoxyphenylsulfonyloxy)cyclobuta[1,2-c:3,4-c'] dipyrrole-1,3,4,6(2H,5H)-tetrone, tetrahydro-2,5-bis(2,4,6-trimethoxyphenylsulfonyloxy)cyclobuta[1,2-c:3,4-c'] dipyrrole-1,3,4,6(2H,5H)-tetrone, tetrahydro-2,5-bis(4-trifluoromethoxyphenylsulfonyloxy)cyclobuta[1,2-c:3,4-c'] dipyrrole-1,3,4,6(2H,5H)-tetrone, tetrahydro-2,5-bis(4-trifluoromethylphenylsulfonyloxy)cyclobuta[1,2-c:3,4-c'] dipyrrole-1,3,4,6(2H,5H)-tetrone, tetrahydro-2,5-bis(3-trifluoromethylphenylsulfonyloxy)cyclobuta[1,2-c:3,4-c'] dipyrrole-1,3,4,6(2H,5H)-tetrone, tetrahydro-2,5-bis(2-trifluoromethylphenylsulfonyloxy)cyclobuta[1,2-c:3,4-c'] dipyrrole-1,3,4,6(2H,5H)-tetrone, tetrahydro-2,5-bis(3,5-di-trifluoromethylphenylsulfonyloxy)cyclobuta[1,2-c:3,4-c'] dipyrrole-1,3,4,6(2H,5H)-tetrone, tetrahydro-2,5-bis(4-chlorophenylsulfonyloxy)cyclobuta[1,2-c:3,4-c']dipyrrole-1,3,4,6(2H,5H)-tetrone, tetrahydro-2,5-bis(4-bromophenylsulfonyloxy)cyclobuta[1,2-c:3,4-c']dipyrrole-1,3,4,6(2H,5H)-tetrone, tetrahydro-2,5-bis(4-iodophenylsulfonyloxy)cyclobuta[1,2-c:3,4-c']dipyrrole-1,3,4,6(2H,5H)-tetrone, tetrahydro-2,5-bis(4-fluorophenylsulfonyloxy)cyclobuta[1,2-c:3,4-c']dipyrrole-1,3,4,6(2H,5H)-tetrone, tetrahydro-2,5-bis(2,5-dichlorophenylsulfonyloxy)cyclobuta[1,2-c:3,4-c'] dipyrrole-1,3,4,6(2H,5H)-tetrone, tetrahydro-2,5-bis(2,4,5-trichlorophenylsulfonyloxy)cyclobuta[1,2-c:3,4-c'] dipyrrole-1,3,4,6(2H,5H)-tetrone, tetrahydro-2,5-bis(pentafluorobenzenesulfonyloxy)cyclobuta[1,2-c:3,4-c'] dipyrrole-1,3,4,6(2H,5H)-tetrone, tetrahydro-2,5-bis(4-nitrophenylsulfonyloxy)cyclobuta[1,2-c:3,4-cl]dipyrrole-1,3,4,6(2H,5H)-tetrone, tetrahydro-2,5-bis(4-acetamidephenylsulfonyloxy)cyclobuta[1,2-c:3,4-c'] dipyrrole-1,3,4,6(2H,5H)-tetrone, tetrahydro-2,5-bis(1-naphthalenesulfonyloxy)cyclobuta[1,2-c:3,4-c']dipyrrole-1,3,4,6(2H,5H)-tetrone, tetrahydro-2,5-bis(2-naphthalenephenylsulfonyloxy)cyclobuta[1,2-c:3,4-c'] dipyrrole-1,3,4,6(2H,5H)-tetrone, tetrahydro-2,5-bis(2,1-naphthoquinonediazide-4-sulfonyloxy)cyclobuta[1,2-c:3,4-c']dipyrrole-1,3,4,6(2H,5H)-tetrone, tetrahydro-2,5-bis(2,1-naphthoquinonediazide-5-sulfonyloxy)cyclobuta[1,2-c:3,4-c']dipyrrole-1,3,4,6(2H,5H)-tetrone, tetrahydro-2,5-bis(4-N,N-dimethylaminonaphthalene-5-sulfonyloxy)cyclobuta-[1,2-c:3,4-c']dipyrrole-1,3,4,6(2H,5H)-tetrone and tetrahydro-2,5-bis(quinoline-8-sulfonyloxy)cyclobuta[1,2-c:3,4-c'] dipyrrole-1,3,4,6(2H,5H)-tetrone, and among others, a preferable one includes, for example, tetrahydro-2,5-bis(nonafluorobutanesulfonyloxy)cyclobuta[1,2-c:3,4-c']dipyrrole-1,3,4,6(2H,5H)-tetrone, tetrahydro-2,5-bis(heptadecafluorooctanesulfonyloxy)cyclobuta[1,2-c:3,4-c']dipyrrole-1,3,4,6(2H,5H)-tetrone, tetrahydro-2,5-bis(10-camphorsulfonyloxy)cyclobuta[1,2-c:3,4-c']dipyrrole-1,3,4,6(2H,5H)-tetrone, tetrahydro-2,5-bis(4-trifluoromethylphenylsulfonyloxy)cyclobuta[1,2-c:3,4-c'] dipyrrole-1,3,4,6(2H,5H)-tetrone, tetrahydro-2,5-bis(3-trifluoromethylphenylsulfonyloxy)cyclobuta[1,2-c:3,4-c'] dipyrrole-1,3,4,6(2H,5H)-tetrone-tetrahydro-2,5-bis(3,5-di-trifluoromethylphenylsulfonyloxy)cyclobuta[1,2-c:3,4-c'] dipyrrole-1,3,4,6(2H,5H)-tetrone and tetrahydro-2,5-bis(pentafluorobenzenesulfonyloxy)cyclobuta[1,2-c:3,4-c'] dipyrrole-1,3,4,6(2H,5H)-tetrone.

The specific examples among the compounds shown by the general formula [10], wherein an aliphatic ring is a cyclopentane ring include, for example, hexahydro-2,6-bis(methanesulfonyloxy)cyclopenta[1,2-c:4,5-c']dipyrrole-1,3,5,7(2H,6H)-tetrone, hexahydro-2,6-bis(ethanesulfonyloxy)cyclopenta[1,2-c:4,5-c']dipyrrole-1,3,5,7(2H,6H)-tetrone, hexahydro-2,6-bis(isopropylsulfonyloxy)cyclopenta[1,2-c:4,5-c']dipyrrole-1,3,5,7(2H,6H)-tetrone, hexahydro-2,6-bis(n-butanesulfonyloxy)cyclopenta[1,2-c:4,5-c']dipyrrole-1,3,5,7(2H,6H)-tetrone, hexahydro-2,6-bis(n-octanesulfonyloxy)cyclopenta[1,2-c:4,5-c']dipyrrole-1,3,5,7(2H,6H)-tetrone, hexahydro-2,6-bis(cyclohexylsulfonyloxy)cyclopenta[1,2-c:4,5-c']dipyrrole-1,3,5,7(2H,6H)-tetrone, hexahydro-2,6-bis(decanesulfonyloxy)cyclopenta[1,2-c:4,5-c']dipyrrole-1,3,5,7(2H,6H)-tetrone, hexahydro-2,6-bis(trichloromethanesulfonyloxy)cyclopenta[1,2-c:4,5-c']dipyrrole-1,3,5,7(2H,6H)-tetrone, hexahydro-2,6-bis(trifluoromethanesulfonyloxy)cyclopenta[1,2-c:4,5-c']dipyrrole-1,3,5,7(2H,6H)-tetrone, hexahydro-2,6-bis(2,2,2-trifluoroethanesulfonyloxy)cyclopenta[1,2-c:4,5-c']dipyrrole-1,3,5,7(2H,6H)-tetrone, hexahydro-2,6-bis(nonafluorobutanesulfonyloxy)cyclopenta[1,2-c:4,5-c']dipyrrole-1,3,5,7(2H,6H)-tetrone, hexahydro-2,6-bis(heptadecafluorooctanesulfonyloxy)cyclopenta[1,2-c:4,5-c']dipyrrole-1,3,5,7(2H,6H)-tetrone, hexahydro-2,6-bis(10-camphorsulfonyloxy)cyclopenta[1,2-c:4,5-c,]dipyrrole-1,3,5,7(2H,6H)-tetrone, hexahydro-2,6-bis(2-thiophenesulfonyloxy)cyclopenta[1,2-c:4,5-c']dipyrrole-1,3,5,7(2H,6H)-tetrone, hexahydro-2,6-bis(benzylsulfonyloxy)cyclopenta[1,2-c:4,5-c']dipyrrole-1,3,5,7(2H,6H)-tetrone, hexahydro-2,6-bis(phenylsulfonyloxy)cyclopenta[1,2-c:4,5-c']dipyrrole-1,3,5,7(2H,6H)-tetrone, hexahydro-2,6-bis(4-methylphenylsulfonyloxy)cyclopenta[1,2-c:4,5-c']dipyrrole-1,3,5,7(2H,6H)-tetrone, hexahydro-2,6-bis(4-ethylphenylsulfonyloxy)cyclopenta[1,2-c:4,5-c']dipyrrole-1,3,5,7(2H,6H)-tetrone, hexahydro-2,6-bis(2,5-dimethylphenylsulfonyloxy)cyclopenta[1,2-c:4,5-c']dipyrrole-1,3,5,7(2H,6H)-tetrone, hexahydro-2,6-bis(2,4,6-trimethylphenylsulfonyloxy)cyclopenta[1,2-c:4,5-c']dipyrrole-1,3,5,7(2H,6H)-tetrone, hexahydro-2,6-bis(4-ethenylphenylsulfonyloxy)cyclopenta[1,2-c:4,5-c']dipyrrole-1,3,5,7(2H,6H)-tetrone, hexahydro-2,6-bis(4-methoxyphenylsulfonyloxy)cyclopenta[1,2-c:4,5-c']dipyrrole-1,3,5,7(2H,6H)-tetrone, hexahydro-2,6-bis(4-dodecylbenzenesulfonyloxy)cyclopenta[1,2-c:4,5-c']dipyrrole-1,3,5,7(2H,6H)-tetrone, hexahydro-2,6-bis(3,4-dimethoxyphenylsulfonyloxy)cyclopenta[1,2-c:4,5-c']dipyrrole-1,3,5,7(2H,6H)-tetrone, hexahydro-2,6-bis(2,4,6-trimethoxyphenylsulfonyloxy)cyclopenta[1,2-c:4,5-c']dipyrrole-1,3,5,7(2H,6H)-tetrone, hexahydro-2,6-bis(4-trifluoromethoxyphenylsulfonyloxy)cyclopenta[1,2-c:4,5-c']dipyrrole-1,3,5,7(2H,6H)-tetrone, hexahydro-2,6-bis(4-trifluoromethylphenylsulfonyloxy)cyclopenta[1,2-c:4,5-c']dipyrrole-1,3,5,7(2H,6H)-tetrone, hexahydro-2,6-bis(3-trifluoromethylphenylsulfonyloxy)cyclopenta[1,2-c:4,5-c']dipyrrole-1,3,5,7(2H,6H)-tetrone, hexahydro-2,6-bis(2-trifluoromethylphenylsulfonyloxy)cyclopenta[1,2-c:4,5-c']dipyrrole-1,3,5,7(2H, 6H)-tetrone, hexahydro-2,6-bis(3,5-di-trifluoromethylphenylsulfonyloxy)cyclopenta[1,2-c:4,5-c']dipyrrole-1,3,5,7(2H,6H)-tetrone, hexahydro-2,6-bis(4-chlorophenylsulfonyloxy)cyclopenta[1,2-c:4,5-c']dipyrrole-1,3,5,7(2H,6H)-tetrone, hexahydro-2,6-bis(4-bromophenylsulfonyloxy)cyclopenta[1,2-c:4,5-c']dipyrrole-1,3,5,7(2H,6H)-tetrone, hexahydro-2,6-bis(4-iodophenylsulfonyloxy)cyclopenta[1,2-c:4,5-c']dipyrrole-1,3,5,7(2H,6H)-tetrone, hexahydro-2,6-bis(4-fluorophenylsulfonyloxy)cyclopenta[1,2-c:4,5-c']dipyrrole-1,3,5,7(2H,6H)-tetrone, hexahydro-2,6-bis(2,5-dichlorophenylsulfonyloxy)cyclopenta[1,2-c:4,5-c']dipyrrole-1,3,5,7(2H,6H)-tetrone, hexahydro-2,6-bis(2,4,5-trichlorophenylsulfonyloxy)cyclopenta[1,2-c:4,5-c']dipyrrole-1,3,5,7(2H,6H)-tetrone, hexahydro-2,6-bis(pentafluorobenzenesulfonyloxy)cyclopenta[1,2-c:4,5-c']dipyrrole-1,3,5,7(2H,6H)-tetrone, hexahydro-2,6-bis(4-nitrophenylsulfonyloxy)cyclopenta[1,2-c:4,5-c']dipyrrole-1,3,5,7(2H,6H)-tetrone, hexahydro-2,6-bis(4-acetamidephenylsulfonyloxy)cyclopenta[1,2-c:4,5-c']dipyrrole-1,3,5,7(2H,6H)-tetrone, hexahydro-2,6-bis(1-naphthalenesulfonyloxy)cyclopenta[1,2-c:4,5-c']dipyrrole-1,3,5,7(2H,6H)-tetrone, hexahydro-2,6-bis(2-naphthalenelsulfonyloxy)cyclopenta[1,2-c:4,5-c']dipyrrole-1,3,5,7(2H,6H)-tetrone, hexahydro-2,6-bis(2,1-naphthoquinonediazide-4-sulfonyloxy)cyclopenta[1,2-c:4,5-c']dipyrrole-1,3,5,7(2H,6H)-tetrone, hexahydro-2,6-bis(2,1-naphthoquinonediazide-5-sulfonyloxy)cyclopenta[1,2-c:4,5-c']dipyrrole-1,3,5,7(2H,6H)-tetrone, hexahydro-2,6-bis(4-N,N-dimethylaminonaphthalene-5-sulfonyloxy)cyclopenta-[1,2-c:4,5-c']dipyrrole-1,3,5,7(2H,6H)-tetrone and hexahydro-2,6-bis(quinoline-8-sulfonyloxy)cyclopenta[1,2-c:4,5-c']dipyrrole-1,3,5,7(2H,6H)-tetrone, and among others, a preferable one includes, for example, hexahydro-2,6-bis(nonafluorobutanesulfonyloxy)cyclopenta[1,2-c:4,5-c']dipyrrole-1,3,5,7(2H,6H)-tetrone, hexahydro-2,6-bis(heptadecafluorooctanesulfonyloxy)cyclopenta[1,2-c:4,5-c']dipyrrole-1,3,5,7(2H,6H)-tetrone, hexahydro-2,6-bis(10-camphorsulfonyloxy)cyclopenta[1,2-c:4,5-c']dipyrrole-1,3,5,7(2H,6H)-tetrone, hexahydro-2,6-bis(4-trifluoromethylphenylsulfonyloxy)cyclopenta[1,2-c:4,5-c']dipyrrole-1,3,5,7(2H,6H)-tetrone, hexahydro-2,6-bis(3-trifluoromethylphenylsulfonyloxy)cyclopenta[1,2-c:4,5-c']dipyrrole-1,3,5,7(2H,6H)-tetrone, hexahydro-2,6-bis(3,5-di-trifluoromethylphenylsulfonyloxy)cyclopenta[1,2-c:4,5-c']dipyrrole-1,3,5,7(2H,6H)-tetrone and hexahydro-2,6-bis(pentafluorobenzenesulfonyloxy)cyclopenta[1,2-c:4,5-c']dipyrrole-1,3,5,7(2H,6H)-tetrone.

The specific examples among the compounds shown by the general formula [10], wherein an aliphatic ring is a cyclohexane ring include, for example, octahydro-2,6-bis(methanesulfonyloxy)cyclohexa[1,2,-c:4,5-c']dipyrrole-1,3,5,7(2H,6H)-tetrone, octahydro-2,6-bis(ethanesulfonyloxy)cyclohexa[1,2-c:4,5-c']dipyrrole-1,3,5,7(2H,6H)-tetrone, octahydro-2,6-bis(isopropylsulfonyloxy)cyclohexa[1,2-c:4,5-c']dipyrrole-1,3,5,7(2H,6H)-tetrone, octahydro-2,6-bis(n-butanesulfonyloxy)cyclohexa[1,2-c:4,5-c']dipyrrole-1,3,5,7(2H,6H)-tetrone, octahydro-2,6-bis(n-octanesulfonyloxy)cyclohexa[1,2-c:4,5-c']dipyrrole-1,3,5,7(2H,6H)-tetrone, octahydro-2,6-bis(cyclohexylsulfonyloxy)cyclohexa[1,2-c:4,5-c']dipyrrole-1,3,5,7(2H,6H)-tetrone, octahydro-2,6-bis(decanesulfonyloxy)cyclohexa[1,2-c:4,5-c']dipyrrole-1,3,5,7(2H,6H)-tetrone, octahydro-2,6-bis(trichloromethanesulfonyloxy)cyclohexa[1,2-c:4,5-c']dipyrrole-1,3,5,7(2H,6H)-tetrone, octahydro-2,6-bis(trifluoromethanesulfonyloxy)cyclohexa[1,2-c:4,5-c']dipyrrole-1,3,5,7(2H,6H)-tetrone, octahydro-2,6-bis(2,2,2-trifluoroethanesulfonyloxy)cyclohexa[1,2-c:4,5-c']dipyrrole-1,3,5,7(2H,6H)-tetrone, octahydro-2,6-bis(nonafluorobutanesulfonyloxy)cyclohexa[1,2-c:4,5-c']dipyrrole-1,3,5,7(2H, 6H)-tetrone octahydro-2,6-bis(heptadecafluorooctanesulfonyloxy)cyclohexa[1,2-c:4,5-c']dipyrrole-1,3,5,7(2H,6H)-tetrone, octahydro-2,6-bis(10-camphorsulfonyloxy)cyclohexa[1,2-c:4,5-c']dipyrrole-1,3,5,7(2H,6H)-tetrone, octahydro-2,6-bis(2-thiophenesulfonyloxy)cyclohexa[1,2-c:4,5-c']dipyrrole-1,3, 5,7(2H,6H)-tetrone, octahydro-2,6-bis(benzylsulfonyloxy) cyclohexa[1,2-c:4,5-c']dipyrrole-1,3,5,7(2H,6H)-tetrone, octahydro-2,6-bis(phenylsulfonyloxy)cyclohexa[1,2-c:4,5-c']dipyrrole-1,3,5,7(2H,6H)-tetrone, octahydro-2,6-bis(4-methylphenylsulfonyloxy)cyclohexa[1,2-c:4,5-c']dipyrrole-1,3,5,7(2H,6H)-tetrone, octahydro-2,6-bis(4-ethylphenylsulfonyloxy)cyclohexa[1,2-c:4,5-c']dipyrrole-1,3,5,7(2H,6H)-tetrone, octahydro-2,6-bis(2,5-dimethylphenylsulfonyloxy)cyclohexa[1,2-c:4,5-c'-]dipyrrole-1,3,5,7(2H,6H)-tetrone, octahydro-2,6-bis(2,4,6-trimethylphenylsulfonyloxy)cyclohexa[1,2-c:4,5-c']dipyrrole-1,3,5,7(2H,6H)-tetrone, octahydro-2,6-bis(4-ethenylphenylsulfonyloxy)cyclohexa[1,2-c:4,5-c']dipyrrole-1,3,5,7(2H,6H)-tetrone, octahydro-2,6-bis(4-methoxyphenylsulfonyloxy)cyclohexa[1,2-c:4,5-c']dipyrrole-1,3,5,7(2H,6H)-tetrone, octahydro-2,6-bis(4-dodecylbenzenesulfonyloxy)cyclohexa[1,2-c:4,5-c']dipyrrole-1,3,5,7(2H,6H)-tetrone, octahydro-2,6-bis(3,4-dimethoxyphenylsulfonyloxy)cyclohexa[1,2-c:4,5-c']dipyrrole-1,3,5,7(2H,6H)-tetrone, octahydro-2,6-bis(2,4,6-trimethoxyphenylsulfonyloxy)cyclohexa[1,2-c:4,5-c']dipyrrole-1,3,5,7(2H,6H)-tetrone, octahydro-2,6-bis(4-trifluoromethoxyphenylsulfonyloxy)cyclohexa[1,2-c:4,5-c']dipyrrole-1,3,5,7(2H,6H)-tetrone, octahydro-2,6-bis(4-trifluoromethylphenylsulfonyloxy)cyclohexa[1,2-c:4,5-c']dipyrrole-1,3,5,7(2H,6H)-tetrone, octahydro-2,6-bis(3-trifluoromethylphenylsulfonyloxy)cyclohexa[1,2-c:4,5-c']dipyrrole-1,3,5,7(2H,6H)-tetrone, octahydro-2,6-bis(2-trifluoromethylphenylsulfonyloxy)cyclohexa[1,2-c:4,5-c']dipyrrole-1,3,5,7(2H,6H)-tetrone, octahydro-2,6-bis(3,5-di-trifluoromethylphenylsulfonyloxy)cyclohexa[1,2-c:4,5-c']dipyrrole-1,3,5,7(2H,6H)-tetrone, octahydro-2,6-bis(4-chlorophenylsulfonyloxy)cyclohexa[1,2-c:4,5-c']dipyrrole-1,3,5,7(2H,6H)-tetrone, octahydro-2,6-bis(4-bromophenylsulfonyloxy)cyclohexa[1,2-c:4,5-c']dipyrrole-1,3,5,7(2H,6H)-tetrone, octahydro-2,6-bis(4-iodophenylsulfonyloxy)cyclohexa[1,2-c:4,5-c']dipyrrole-1,3,5,7(2H,6H)-tetrone, octahydro-2,6-bis(4-fluorophenylsulfonyloxy)cyclohexa[1,2-c:4,5-c']dipyrrole-1,3,5,7(2H,6H)-tetrone, octahydro-2,6-bis(2,5-dichlorophenylsulfonyloxy)cyclohexa[1,2-c:4,5-c']dipyrrole-1,3,5,7(2H,6H)-tetrone, octahydro-2,6-bis(2,4,5-trichlorophenylsulfonyloxy)cyclohexa[1,2-c:4,5-c']dipyrrole-1,3,5,7(2H,6H)-tetrone, octahydro-2,6-bis(pentafluorobenzenesulfonyloxy)cyclohexa[1,2-c:4,5-c']dipyrrole-1,3,5,7(2H,6H)-tetrone, octahydro-2,6-bis(4-nitrophenylsulfonyloxy)cyclohexa[1,2-c:4,5-c']dipyrrole-1,3,5,7(2H,6H)-tetrone, octahydro-2,6-bis(4-acetamidephenylsulfonyloxy)cyclohexa[1,2-c:4,5-c']dipyrrole-1,3,5,7(2H,6H)-tetrone, octahydro-2,6-bis(1-naphthalenesulfonyloxy)cyclohexa[1,2-c:4,5-c']dipyrrole-1,3,5,7(2H,6H)-tetrone, octahydro-2,6-bis(2-naphthalenelsulfonyloxy)cyclohexa[1,2-c:4,5-c']dipyrrole-1,3,5,7(2H,6H)-tetrone, octahydro-2,6-bis(2,1-naphthoquinonediazide-4-sulfonyloxy)cyclohexa[1,2-c:4,5-c']dipyrrole-1,3,5,7(2H,6H)-tetrone, octahydro-2,6-bis(2,1-naphthoquinonediazide-5-sulfonyloxy)cyclohexa[1,2-c:4,5-c']dipyrrole-1,3,5,7(2H,6H)-tetrone, octahydro-2,6-bis(4-N,N-dimethylaminonaphthalene-5-sulfonyloxy)cyclohexa-[1,2-c:4,5-c']dipyrrole-1,3,5,7(2H,6H)-tetrone and octahydro-2,6-bis(quinoline-8-sulfonyloxy)cyclohexa[1,2-c:4,5-c']dipyrrole-1,3,5,7(2H,6H)-tetrone.

The specific examples of the compounds shown by the general formula [11] include, for example, 3a,4,4a,7a,8,8a-hexahydro-2,6-bis(n-hexanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(n-octanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(cyclohexylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(decanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(trichloromethanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(trifluoromethanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(2,2,2-trifluoroethanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(nonafluorobutanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(heptadecafluorooctanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(10-camphorsulfonyloxy)-4,8-ethenobenzo[1,2-c:4,5-c']dipyrrole-1,3,5,7(2H,6H)-tetrone, 3a,4,4a,7a,8,8a-hexahydrd-2,6-bis(2-thiophenesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(benzylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(phenylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(4-methylphenylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(4-ethylphenysulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(2,5-dimethylphenylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis-(2,4,6-trimethylphenylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(4-ethenylphenylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(4-methoxyphenylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(4-dodecylbenzenesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(3,4-dimethoxyphenylsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(2,4,6-trimethoxyphenylsulfonyloxy)-4,8-ethenobenzo[1,2-c:3,4-c']dipyrrole-1,3,5,7(2H,6H)-tetrone, a,4,4a,7a,8,8a-hexahydro-2,6-bis(4-trifluoromethoxyphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(4-trifluoromethylphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(3-trifluoromethylphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(2-trifluoromethylphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(3,5-di-trifluoromethylphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(4-chlorophenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(4-bromophenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(4-iodolphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(4- fluorophenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(2,5-dichlorophenylsulfonyloxy)-4,8-ethenobenzo[1,2-c:3,4-c']dipyrrole-1,3,5,7(2H,6H)-tetrone, 3a,4,4a,7a,8,8a-hexahydro-2;6-bis(2,4,5-trichlorophenylsulfonyloxy)-4,8-ethenobenzo[1,2-c:3,4-c']dipyrrole-1,3,5,7(2H,6H)-tetrone, 3a,4, 4a,7a,8,8a-hexahydro-2,6-bis(pentafluorobenzenesulforiyloxy)-4,8-ethenobenzo[1,2-c:3,4-c']dipyrrole-1,3,5,7(2H,6H)-tetrone, 3a,4,4a,7a,8,8a-hexahydro-2,6-bis(4-nitrolphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(4-acetamidephenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(1-naphthalenesulfonyloxy)-4,8-ethenobenzo[1,2-c:3,4-c']dipyrrole-1,3,5,7(2H,6H)-tetrone, 3a,4, 4a,7a,8,8a-hexahydro-2,6-bis(2-naphthalenesulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(2,1-naphthoquinonediazide-4-sulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(2,1-naphthoquinonediazide-5-sulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(4-N,N-dimethylaminonaphthalenesulfonyloxy)-4,8-ethenobenzo[1,2-c:3,4-c']dipyrrole-1,3,5,7(2H,6H)-tetrone and 3a,4,4a,7a,8,8a-hexahydro-2,6-bis(quinoline-8-sulfonyloxy)-4,8-ethenobenzo[1,2-c:3,4-c']dipyrrole-1,3,5,7(2H,6H)-tetrone, and among others, a preferable one includes, for example, 3a,4,4a,7a,8,8a-hexahydro-2,6-bis(nonafluorobutanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(heptadecafluorooctanesulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(10-camphorsulfonyloxy)-4,8-ethenobenzo[1,2-c:4,5-c']dipyrrole-1,3,5,7(2H,6H)-tetrone, 3a,4,4a,7a,8,8a-hexahydro-2,6-bis(4-trifluoromethylphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(3-trifluoromethylphenylsulfonyloxy)-4,8-ethenobenzo[1,2-c:3,4-c']dipyrrole-1,3,5,7(2H,6H)-tetrone, 3a,4,4a,7a,8,8a-hexahydro-2,6-bis(3,5-di-trifluoromethylphenylsulfonyloxy)-4,8-ethenobenzo[1,2-c:3,4-c']dipyrrole-1,3,5,7(2H,6H)-tetrone and 3a,4,4a,7a,8,8a-hexahydro-2,6-bis(pentafluorobenzenesulfonyloxy)-4,8-ethenobenzo[1,2-c:3,4-c']dipyrrole-1,3,5,7(2H,6H)-tetrone.

The specific examples of the compounds shown by the general formula [12] include, for example, 2,6-bis(isopropylsulfonyloxy)benzo[1,2-c:4,5-c']dipyrrole-1,3,5,7(2H,6H)-tetrone, 2,6-bis(n-butanesulfonyloxy)benzo[1,2-c:4,5-c']dipyrrole-1,3,5,7(2H,6H)-tetrone, 2,6-bis(n-octanesulfonyloxy)benzo[1,2-c:4,5-c']dipyrrole-1,3,5,7(2H,6H)-tetrone, 2,6-bis(cyclohexylsulfonyloxy)benzo[1,2-c:4,5-c']dipyrrole-1,3,5,7(2H,6H)-tetrone, 2,6-bis(decanesulfonyloxy)benzo[1,2-c:4,5-c']dipyrrole-1,3,5,7(2H,6H)-tetrone, 2,6-bis(trichloromethanesulfonyloxy)benzo[1,2-c:4,5-c']dipyrrole-1,3,5,7(2H,6H)-tetrone, 2,6-bis(trifluoromethanesulfonyloxy)benzo[1,2-c:4,5-c']dipyrrole-1,3,5,7(2H,6H)-tetrone, 2,6-bis(2,2,2-trifluoroethanesulfonyloxy)benzo[1,2-c:4,5-c']dipyrrole-1,3,5,7(2H,6H)-tetrone, 2,6-bis(nonafluorobutansulfonyloxy)benzo[1,2-c:4,5-c']dipyrrole-1,3,5,7(2H,6H)-tetrone, 2,6-bis(heptadecafluorooctanesulfonyloxy)benzo[1,2-c:4,5-c']dipyrrole-1,3,5,7(2H,6H)-tetrone, 2,6-bis(10-camphorsulfonyloxy)benzo[1,2-c:4,5-c']dipyrrole-1,3,5,7(2H,6H)-tetrone, 2,6-bis(2-thiophenesulfonyloxy)benzo[1,2-c:4,5-c']dipyrrole-1,3,5,7(2H,6H)-tetrone, 2,6-bis(benzylsulfonyloxy)benzo[1,2-c:4,5-c']dipyrrole-1,3,5,7(2H,6H)-tetrone, 2,6-bis(phenylsulfonyloxy)benzo[1,2-c:4,5-c']dipyrrole-1,3,5,7(2H,6H)-tetrone, 2,6-bis(4-methylphenylsulfonyloxy)benzo[1,2-c:4,5-c']dipyrrole-1,3,5,7(2H,6H)-tetrone, 2,6-bis(4-ethylphenylsulfonyloxy)benzo[1,2-c:4,5-c']dipyrrole-1,3,5,7(2H,6H)-tetrone, 2,6-bis(2,5-dimethylphenylsulfonyloxy)benzo[1,2-c:4,5-c']dipyrrole-1,3,5,7(2H,6H)-tetrone, 2,6-bis(2,4,6-trimethylphenylsulfonyloxy)benzo[1,2-c:4,5-c']dipyrrole-1,3,5,7(2H,6H)-tetrone, 2,6-bis(4-ethenylphenylsulfonyloxy)benzo[1,2-c:4,5-c']dipyrrole-1,3,5,7(2H,6H)-tetrone, 2,6-bis(4-methoxyphenylsulfonyloxy)benzo[1,2-c:4,5-c']dipyrrole-1,3,5,7(2H,6H)-tetrone, 2,6-bis(4-dodecylbenzenesulfonyloxy)benzo[1,2-c:4,5-c']dipyrrole-1,3,5,7(2H,6H)-tetrone, 2,6-bis(3,4-dimethoxyphenylsulfonyloxy)benzo[1,2-c:4,5-c']dipyrrole-1,3,5,7(2H,6H)-tetrone, 2,6-bis(2,4,6-trimethoxyphenylsulfonyloxy)benzo[1,2-c:4,5-c']dipyrrole-1,3,5,7(2H,6H)-tetrone, 2,6-bis(4-trifluoromethoxyphenylsulfonyloxy)benzo[1,2-c:4,5-c']dipyrrole-1,3,5,7(2H,6H)-tetrone, 2,6-bis(4-trifluoromethylphenylsulfonyloxy)benzo[1,2-c:4,5-c']dipyrrole-1,3,5,7(2H,6H)-tetrone, 2,6-bis(3-trifluoromethylphenylsulfonyloxy)benzo[1,2-c:4,5-c']dipyrrole-1,3,5,7(2H,6H)-tetrone, 2,6-bis(2-trifluoromethylphenylsulfonyloxy)benzo[1,2-c:4,5-c']dipyrrole-1,3,5,7(2H,6H)-tetrone, 2,6-bis(3,5-di-trifluoromethylphenylsulfonyloxy)benzo[1,2-c:4,5-c']dipyrrole-1,3,5,7(2H,6H)-tetrone, 2,6-bis(4-chlorophenylsulfonyloxy)benzo[1,2-c:4,5-c']dipyrrole-1,3,5,7(2H,6H)-tetrone, 2,6-bis(4-bromophenylsulfonyloxy)benzo[1,2-c:4,5-c']dipyrrole-1,3,5,7(2H,6H)-tetrone, 2,6-bis(4-iodophenylsulfonyloxy)benzo[1,2-c:4,5-c']dipyrrole-1,3,5,7(2H,6H)-tetrone, 2,6-bis(4-fluorophenylsulfonyloxy)benzo[1,2-c:4,5-c']dipyrrole-1,3,5,7(2H,6H)-tetrone, 2,6-bis(2,5-dichlorophenylsulfonyloxy)benzo[1,2-c:3,4-c']dipyrrole-1,3,5,7(2H,6H)-tetrone, 2,6-bis(2,4,5-trichlorophenylsulfonyloxy)benzo[1,2-c:3,4-c']dipyrrole-1,3,5,7(2H,6H)-tetrone, 2,6-bis(pentafluorobenzenesulfonyloxy)benzo[1,2-c:3,4-c']dipyrrole-1,3,5,7(2H,6H)-tetrone, 2,6-bis(4-nitrophenylsulfonyloxy)benzo[1,2-c:3,4-c']dipyrrole-1,3,5,7(2H,6H)-tetrone, 2,6-bis(4-acetamidephenylsulfonyloxy)benzo[1,2-c:3,4-c']dipyrrole-1,3,5,7(2H,6H)-tetrone, 2,6-bis(1-naphthalenesulfonyloxy)benzo[1,2-c:3,4-c']dipyrrole-1,3,5,7(2H,6H)-tetrone, 2,6-bis(2-naphthalenesulfonyloxy)benzo[1,2-c:3,4-c']dipyrrole-1,3,5,7(2H,6H)-tetrone, 2,6-bis(2,1-naphthoquinonediazide-4-sulfonyloxy)benzo[1,2-c:3,4-c']dipyrrole-1,3,5,7(2H,6H)-tetrone, 2,6-bis(2,1-naphthoquinonediazide-5-sulfonyloxy)benzo[1,2-c:3,4-c']dipyrrole-1,3,5,7(2H,6H)-tetrone, 2,6-bis(4-N,N-dimethylaminonaphthalene-5-sulfonyloxy)benzo[1,2-c:3,4-c']-dipyrrole-1,3,5,7(2H,6H)-tetrone and 2,6-bis(quinoline-8-sulfonyloxy)benzo[1,2-c:3,4-c']dipyrrole-1,3,5,7(2H,6H)-tetrone, and among others, a preferable one includes, for example, 2,6-bis(nonafluorobutansulfonyloxy)benzo[1,2-c:4,5-c']dipyrrole-1,3,5,7(2H,6H)-tetrone, 2,6-bis(heptadecafluorooctanesulfonyloxy)benzo[1,2-c:4,5-c']dipyrrole-1,3,5,7(2H,6H)-tetrone, 2,6-bis(10-camphorsulfonyloxy)benzo[1,2-c:4,5-c']dipyrrole-1,3,5,7(2H,6H)-tetrone, 2,6-bis(4-trifluoromethylphenylsulfonyloxy)benzo[1,2-c:4,5-c']dipyrrole-1,3,5,7(2H,6H)-tetrone, 2,6-bis(3-trifluoromethylphenylsulfonyloxy)benzo[1,2-c:4,5-c']dipyrrole-1,3,5,7(2H,6H)-tetrone, 2,6-bis(3,5-di-trifluoromethylphenylsulfonyloxy)benzo[1,2-c:4,5-c']dipyrrole-1,3,5,7(2H,6H)-tetrone and 2,6-bis (pentafluorobenzenesulfonyloxy)benzo[1,2-c:4,5-c']dipyrrole-1,3,5,7(2H,6H)-tetrone.

The specific example of the compound shown by the general formula [25] includes, for example, 5,5'-oxybis[2-hydroxy-1H-isoindole-1,3(2H)-dione].

The specific examples of the compounds shown by the general formula [13] includes, for example, 5,5'-oxybis[2-methanesulfonyloxy-1H-isoindole-1,3(2H)-dione], 5,5'-oxybis[2-ethanesulfonyloxy-1H-isoindole-1,3(2H)-dione], 5,5'-oxybis[2-n-propanesulfonyloxy-1H-isoindole-1,3(2H)-dione], 5,5,-oxybis[2-isopropylsulfonyloxy-1H-isoindole-1,3(2H)-dione], 5,5'-oxybis[2-n-butanesulfonyloxy-1H-isoindole-1,3(2H)-dione], 5,5'-oxybis[2-n-hexanesulfonyloxy-1H-isoindole-1,3(2H)-dione], 5,5'-oxybis[2-n-octanesulfonyloxy-1H-isoindole-1,3(2H)-dione], 5,5'-oxybis[2-cyclohexylsulfonyloxy-1H-isoindole-1,3(2H)-dione], 5,5'-oxybis[2-decanesulfonyloxy-1H-isoindole-1,3(2H)-dione], 5,5'-oxybis[2-nonafluorobutanesulfonyloxy-1H-isoindole-1,3(2H)-dione], 5,5'-oxybis[2-heptadecafluorooctanesulfonyloxy-1H-isoindole-1,3(2H)-dione], 5,51-oxybis[2-(10-camphor)sulfonyloxy-1H-isoindole-1,3(2H)-dione], 5,5'-oxybis[2-benzylsulfonyloxy-1H-isoindole-1,3(2H)-dione], 5,5'-oxybis[2-phenylsulfonyloxy-1H-isoindole-1,3(2H)-dione], 5,5'-oxybis[2-(4-ethylphenylsulfonyl)oxy-1H-isoindole-1,3(2H)-dione], 5,5'-oxybis[2-(2,5-dimethylphenylsulfonyl)oxy-1H-isoindole-1,3(2H)-dione], 5,5'-oxybis[2-(2,4,6-trimethylphenylsulfonyl)oxy-1H-isoindole-1,3(2H)-dione], 5,5'-oxybis[2-(4-ethenylphenylsulfony)oxy-1H-isoindole-1,3 (2H)-dione], 5,5'-oxybis[2-(4-methoxyphenylsulfony)oxy-1H-isoindole-1,3(2H)-dione], 5,5'-oxybis[2-(4-dodecylbenzenesulfonyl)oxy-1H-isoindole-1,3(2H)-dione], 5,5'-oxybis[2-(3,4-dimethoxyphenylsulfonyl)oxy-1H-isoindole-1,3(2H)-dione], 5,5'-oxybis[2-(2,4,6-trimethoxyphenylsulfonyl)oxy-1H-isoindole-1,3(2H)-dione], 5,5'-oxybis[2-(4-trifluoromethoxyphenylsulfonyl)oxy-1H-isoindole-1,3(2H)-dione], 5,5'-oxybis[2-(4-trifluoromethylphenylsulfonyl)oxy-1H-isoindole-1,3(2H)-dione], 5,5'-oxybis[2-(3-trifluoromethylphenylsulfonyl)oxy-1H-isoindole-1,3(2H)-dione], 5,5'-oxybis[2-(2-trifluoromethylphenylsulfonyl)oxy-1H-isoindole-1,3(2H)-dione], 5,5'-oxybis[2-(3,5-di-trifluoromethylphenylsulfonyl)oxy-1H-isoindole-1,3(2H)-dione], 5,5'-oxybis[2-(4-chlorophenylsulfonyl)oxy-1H-isoindole-1,3(2H)-dione], 5,5'-oxybis[2-(4-bromophenylsulfonyl)oxy-1H-isoindole-1,3(2H)-dione], 5,5'-oxybis[2-(4-iodophenylsulfonyl)oxy-1H-isoindole-1,3(2H)-dione], 5,5'-oxybis[2-(4-fluorophenylsulfonyl)oxy-1H-isoindole-1,3(2H)-dione], 5,5'-oxybis[2-(2,5-dichlorophenylsulfonyl)oxy-1H-isoindole-1,3(2H)-dione], 5,5'-oxybis[2-(2,4,5-trichlorophenylsulfonyl)oxy-1H-isoindole-1,3(2H)-dione], 5,5'-oxybis[2-(pentafluorobenzenesulfonyl)oxy-1H-isoindole-1,3(2H)-dione], 5,5'-oxybis[2-(4-nitrophenylsulfonyl)oxy-1H-isoindole-1,3(2H)-dione], 5,5'-oxybis[2-(4-acetamidephenylsulfonyl)oxy-1H-isoindole-1,3(2H)-dione], 5,5'-oxybis[2-(1-naphthalenesulfonyl)oxy-1H-isoindole-1,3(2H)-dione], 5,5'-oxybis[2-(2-naphthalenesulfonyl)oxy-1H-isoindole-1,3(2H)-dione], 5,5'-oxybis[2-(2-thienylsulfonyl)oxy-1H-isoindole-1,3(2H)-dione], 5,5'-oxybis[2-(2,1-naphthoquinonediazide-4-sulfonyl)oxy-1H-isoindole-1,3(2H)-dione], 5,5'-oxybis[2-(2,1-naphthoquinonediazide-5-sulfonyl)oxy-1H-isoindole-1,3(2H)-dione], 5,5'-oxybis[2-(4-N,N-dimethylaminonaphthalene-5-sulfonyl)oxy-1H-isoindole-1,3(2H)-dione] and 5,5'-oxybis[2-(quinoline-8-sulfonyl)oxy-1H-isoindole-1,3(2H)-dione], and among others, a preferable one includes, for example, 5,5'-oxybis[2-nonafluorobutanesulfonyloxy-1H-isoindole-1,3(2H)-dione], 5,5'-oxybis[2-heptadecafluorooctanesulfonyloxy-1H-isoindole-1,3(2H)-dione], 5,5'-oxybis[2-(10-camphor)sulfonyloxy-1H-isoindole-1,3(2H)-dione], 5,5'-oxybis[2-(4-trifluoromethylphenylsulfonyl)oxy-1H-isoindole-1,3(2H)-dione], 5,5'-oxybis[2-(3-trifluoromethylphenylsulfonyl)oxy-1H-isoindole-1,3(2H)-dione], 5,5'-oxybis[2-(3,5-di-trifluoromethylphenylsulfonyl)oxy-1H-isoindole-1,3(2H)-dione] and 5,5'-oxybis[2-(pentafluorobenzenesulfonyl)oxy-1H-isoindole-1,3(2H)-dione].

The specific examples of the compounds shown by the general formula [14] include, for example, 5,5'-[2,2,2-trifluoro-1-(trifluoromethyl)ethylidene]bis[2-methanesulfonyloxy-1H-isoindole-1,3(2H)-dione], 5,5'-[2,2,2-trifluoro-1-(trifluoromethyl)ethylidene]bis[2-ethanesulfonyloxy-1H-isoindole-1,3(2H)-dione], 5,5'-[2,2,2-trifluoro-1-(trifluoromethyl)ethylidene]bis[2-n-prpanesulfonyloxy-1H-isoindole-1,3(2H)-dione], 5,5'-[2,2,2-trifluoro-1-(trifluoromethyl)ethylidene]bis[2-isopropylsulfonyloxy-1H-isoindole-1,3(2H)-dione], 5,5'-[2,2,2-trifluoro-1-(trifluoromethyl)ethylidene]bis[2-n-butanesulfonyloxy-1H-isoindole-1,3(2H)-dione], 5,5'-[2,2,2-trifluoro-1-(trifluoromethyl)ethylidene]bis[2-n-hexanesulfonyloxy-1H-isoindole-1,3(2H)-dione], 5,5'-[2,2,2-trifluoro-1-(trifluoromethyl)ethylidene]bis[2-n-octanesulfonyloxy-1H-isoindole-1,3(2H)-dione], 5,5'-[2,2,2-trifluoro-1-(trifluoromethyl)ethylidene]bis[2-cyclohexylsulfonyloxy-1H-isoindole-1,3(2H)-dione], 5,5'-[2,2,2-trifluoro-1-(trifluoromethyl)ethylidene]bis[2-decanesulfonyloxy-1H-isoindole-1,3(2H)-dione], 5,5'-[2,2,2-trifluoro-1-(trifluoromethyl)ethylidene]bis[2-nonafluorobutanesulfonyloxy-1H-isoindole-1,3(2H)-dione], 5,5'-[2,2,2-trifluoro-1-(trifluoromethyl)ethylidene]bis[2-heptadecafluorooctanesulfonyloxy-1H-isoindole-1,3(2H)-dione], 5,5'-[2,2,2-trifluoro-1-(trifluoromethyl)ethylidene]bis[2-(10-camphorsulfonyl)oxy-1H-isoindole-1,3(2H)-dione], 5,5'-[2,2,2-trifluoro-1-(trifluoromethyl)ethylidene]bis[2-benzylsulfonyloxy-1H-isoindole-1,3(2H)-dione], 5,5'-[2,2,2-trifluoro-1-(trifluoromethyl)ethylidene]bis[2-phenylsulfonyloxy-1H-isoindole-1,3(2H)-dione], 5, 5'-[2,2,2-trifluoro-1-(trifluoromethyl)ethylidene]bis[2-(4-toluenesulfonyl)oxy-1H-isoindole-1,3(2H)-dione], 5,5'-[2,2,2-trifluoro-1-(trifluoromethyl)ethylidene]bis [2-(4-ethylphenylsulfonyl)oxy-1H-isoindole-1,3(2H)-dione], 5,5'-[2,2,2-trifluoro-1-(trifluoromethyl)ethylidene]bis[2-(2,5-dimethylphenylsulfonyl)oxy-1H-isoindole-1,3(2H)-dione], 5,5,-[2,2,2-trifluoro-1-(trifluoromethyl)ethylidene]bis[2-(2,4,6-trimethylphenylsulfonyl)oxy-1H-isoindole-1,3(2H)-dione], 5,5'-[2,2,2-trifluoro-1-(trifluoromethyl)ethylidene]bis [2-(2,4,6-tremethylphenylsulfonyl)oxy-1H-isoindole-1,3(2H)-dione], 5,5'-[2,2,2-trifluoro-1-(trifluoromethyl)ethylidene]bis[2-(4-dodecylbenzenelsulfonyl)oxy-1H-isoindole-1,3(2H)-dione], 5,5'-[2,2,2-trifluoro-1-(trifluoromethyl)ethylidene]bis[2-(4-methoxyphenylsulfonyl)oxy-1H-isoindole-1,3(2H)-dione], 5,5'-[2,2,2-trifluoro-1-(trifluoromethyl)ethylidene]bis[2-(4-dimethoxyphenylsulfonyl)oxy-1H-isoindole-1,3(2H)-dione], 5,5'-[2,2,2-trifluoro-1-(trifluoromethyl)ethylidene][2(3,4-dimethyloxyphenylsulfonyl)oxy-1-isoindole-1,3(2H)-dione], 5,5'-[2,2,2-trifluoro-1-(trifluoromethyl)ethylidene]bis[2-(2,4,6-trifluoromethoxyphenylsulfonyl)oxy-1H-isoindole-1,3(2H)-dione], 5,5'-[2,2,2-trifluoro-1-(trifluoromethyl)ethylidene]bis[2-(4-trifluoromethylphenylsulfonyl)oxy-1H-isoindole-1,3(2H)-dione], 5,5'-[2,2,2-trifluoro-1-(trifluoromethyl)ethylidene]bis[2-(3-trifluoromethylphenylsulfonyl)oxy-1H-isoindole-1,3(2H)-dione], 5,5'-[2,2,2-trifluoro-1-(trifluoromethyl)

ethylidene]bis[2-(2-trifluoromethylphenylsulfonyl)oxy-1H-isoindole-1,3(2H)-dione], 5,5'-[2,2,2-triflubro-1-(trifluoromethyl)ethylidene]bis[2-(3,5-di-trifluoromethylphenylsulfonyl)oxy-1H-isoindole-1,3(2H)-dione], 5,5'-[2,2,2-trifluoro-1-(trifluoromethyl)ethylidene]bis[2-4(4-chlorophenylsulfonyl)oxy-1H-isoindole-1,3(2H)-dione], 5,5'-[2,2,2-trifluoro-1-(trifluoromethyl)ethylidene]bis[2-(4-bromophenylsulfonyl)oxy-1H-isoindole-1,3(2H)-dione], 5,5'-[2,2,2-trifluoro-1-(trifluoromethyl)ethylidene]bis[2-(4-iodophenylsulfonyl)oxy-1H-isoindole-1,3(2H)-dione], 5,5'-[2,2,2-trifluoro-1-(trifluoromethyl)ethylidene]bis[2-(4-fluorophenylsulfonyl)oxy-1H-isoindole-1,3(2H)-dione], 5,5'-[2,2,2-trifluoro-1-(trifluoromethyl)ethylidene]bis[2-(2,5-dichlorophenylsulfonyl)oxy-1H-isoindole-1,3(2H)-dione], 5,5'-[2,2,2-trifluoro-1-(trifluoromethyl)ethylidene]bis[2-(2,4,5-trichlorophenylsulfonyl)oxy-1H-isoindole-1,3(2H)-dione], 5,5'-[2,2,2-trifluoro-1-(trifluoromethyl)ethylidene]bis[2-(pentafluorobenzenesulfonyl)oxy-1H-isoindole-1,3(2H)-dione], 5,5'-[2,2,2-trifluoro-1-(trifluoromethyl)ethylidene]bis[2-(4-nitrophenylsulfonyl)oxy-1H-isoindole-1,3(2H)-dione], 5,5'-[2,2,2-trifluoro-1-(trifluoromethyl)ethylidene]bis[2-(4-acetamidephenylsulfonyl)oxy-1H-isoindole-1,3(2H)-dione], 5,5'-[2,2,2-trifluoro-1-(trifluoromethyl)ethylidene]bis[2-(1-naphthalenesulfonyl)oxy-1H-isoindole-1,3(2H)-dione], 5,5'-[2,2,2-trifluoro-1-(trifluoromethyl)ethylidene]bis[2-naphthalenesulfonyl)oxy-1H-isoindole-1,3(2H)-dione], 5,5'-[2,2,2-trifluoro-1-(trifluoromethyl)ethylidene]bis[2-(2-thienylsulfonyl)oxy-1H-isoindole-1,3(2H)-dione], 5,5'-[2,2,2-trifluoro-1-(trifluoromethyl)ethylidene]bis[2-(2,1-naphthoquinonediazide-4-sulfonyl)oxy-1H-isoindole-1,3(2H)-dione], 5,5'-[2,2,2-trifluoro-1-(trifluoromethyl)ethylidene]bis[2-(2,1-naphthoquinonediazide-5-sulfonyl)oxy-1H-isoindole-1,3(2H)-dione], 5,5'-[2,2,2-trifluoro-1-(trifluoromethyl)ethylidene]bis[2-(4-N,N-dimethylaminonaphthalene-5-sulfonyl)oxy-1H-isoindole-1,3(2H)-7dione] and 5,5'-[2,2,2-trifluoro-1-(trifluoromethyl)ethylidene]bis[2-(quinoline-8-sulfonyl)oxy-1H-isoindole-1,3 (2H)-dione], and among others, a preferable one includes, for example, 5,5'-[2,2,2-trifluoro-1-(trifluoromethyl)ethylidene]bis[2-nonafluorobutanesulfonyloxy-1H-isoindole-1,3(2H)-dione], 5,5'-[2,2,2-trifluoro-1-(trifluoromethyl)ethylidene]biss[2-heptadecafluorooctanesulfonyloxy-1H-isoindole-1,3(2H)-dione], 5,5'-[2,2,2-trifluoro-1-(trifluoromethyl)ethylidene]bis[2-(10-camphorsulfonyl)oxy-1H-isoindole-1,3(2H)-dione], 5,5'-[2,2,2-trifluoro-1-(trifluoromethyl)ethylidene]bis[2-(4-trifluoromethylphenylsulfonyl)oxy-1H-isoindole-1,3(2H)-dione], 5,5'-[2,2,2-trifluoro-1-(trifluoromethyl)ethylidene]bis[2-(3-trifluoromethylphenylsulfonyl)oxy-1H-isoindole-1,3(2H)-dione], 5,5'-[2,2,2-trifluoro-1-(trifluoromethyl)ethylidene]bis[2-(3,5-di-trifluoromethylphenylsulfonyl)oxy-1H-isoindole-1,3(2H)-dione] and 5,5'-[2,2,2-trifluoro-1-(trifluoromethyl)ethylidene]bis[2-(pentafluorobenzenesulfonyl)oxy-1H-isoindole-1,3(2H)-dione].

The specific examples of the compounds shown by the general formula [15] include, for example, 5,5'-bis[2-methanesulfonyloxy-1H-isoindole-1,3(2H),-dione], 5,5'-bis[2-ethanesulfonyloxy-1H-isoindole-1,3(2H)-dione], 5,5'-bis[2-n-propanesulfonyloxy-1H-isoindole-1,3(2H)-dione], 5,5'-bis[2-isopropylsulfonyloxy-1H-isoindole-1,3(2H)-dione], 5,5'-bis[2-n-butanesulfonyloxy-1H-isoindole-1,3(2H)-dione], 5,5'-bis[2-n-hexanesulfonyloxy-1H-isoindole-1,3(2H)-dione], 5,5'-bis[2-n-octanesulfonyloxy-1H-isoindole-1,3(2H)-dione], 5,5'-bis[2-cyclohexylsulfonyloxy-1H-isoindole-1,3(2H)-dione], 5,5'-bis[2-decanesulfonyloxy-1H-isoindole-1,3(2H)-dione], 5,5'-bis[2-nonafluorobutanesulfonyloxy-1H-isoindole-1,3(2H)-dione], 5,5'-bis [2-heptadecafluorooctanesulfonyloxy-1H-isoindole-1,3(2H)-dione], 5,5'-bis[2-(10-camphorsulfonyl)oxy-1H-isoindole-1,3,(2H)-dione], 5,5'-bis[2-benzylsulfonyloxy-1H-isoindole-1,3(2H)-dione], 5,5'-bis[2-phenylsulfonyloxy-1H-isoindole-1,3(2H)-dione], 5,5'-bis[2-(4-toluenesulfonyl)oxy-1H-isoindole-1,3(2H)-dione], 5,5'-bis[2-(4-ethylphenylsulfonyl)oxy-1H-isoindole-1,3(2H)-dione], 5,5'-bis[2-(2,5-dimethylphenylsulfonyl)oxy-1H-isoindole-1,3(2H)-dione]5,5'-bis[2-(2,4,6-trimethylphenylsulfonyl)oxy-1H-isoindole-1,3(2H)-dione], 5,5'-bis[2-(4-ethenylphenylsulfonyl)oxy-1H-isoindole-1,3(2H)-dione], 5,5'-bis[2-(4-methoxyphenylsulfonyl)oxy-1H-isoindole-1,3(2H)-dione], 5,5'-bis[2-(4-dodecylbenzenesulfonyl)oxy-1H-isoindole-1,3(2H)-dione], 5,5'-bis[2-(3,4-dimethoxyphenylsulfonyl)oxy-1H-isoindole-1,3(2H)-dione], 5,5'-bis[2-(2,4,6-trimethoxyphenylsulfonyl)oxy-1H-isoindole-1,3(2H)-dione], 5,5'-bis[2-(4-trifluoromethoxyphenylsulfonyl)oxy-1H-isoindole-1,3(2H)-dione], 5,5'-bis[2-(4-trifluoromethylphenylsulfonyl)oxy-1H-isoindole-1,3(2H)-dione], 5,5'-bis[2-(3-trifluoromethylphenylsulfonyl)oxy-1H-isoindole-1,3(2H)-dione], 5,5'-bis[2-(2-trifluoromethylphenylsulfonyl)oxy-1H-isoindole-1,3(2H)-dione], 5,5'-bis[2-(3,5-di-trifluoromethylphenylsulfonyl)oxy-1H-isoindole-1,3(2H)-dione], 5,5'-bis[2-(4-chlorolphenylsulfonyl)oxy-1H-isoindole-1,3(2H)-dione], 5,5'-bis[2-(4-bromophenylsulfonyl)oxy-1H-isoindole-1,3(2H)-dione], 5,5'-bis[2-(4-iodophenylsulfonyl)oxy-1H-isoindole-1,3(2H)-dione], 5,5'-bis[2-(4-fluorophenylsulfonyl)oxy-1H-isoindole-1,3(2H)-dione], 5,5'-bis[2-(2,5-dichlorophenylsulfonyl)oxy-1H-isoindole-1,3(2H)-dione], 5,5'-bis[2-(2,4,5-trichlorophenylsulfonyl)oxy-1H-isoindole-1,3(2H)-dione], 5,5'-bis[2-(pentafluorobenzenesulfonyl)oxy-1H-isoindole-1,3(2H)-dione], 5,5'-bis[2-(4-nitrophenylsulfonyl)oxy-1H-isoindole-1,3(2H)-dione], 5,5'-bis[2-(4-acetamidephenylsulfonyl)oxy-1H-isoindole-1,3(2H)-dione], 5,5'-bis[2-(1-naphthalenesulfonyl)oxy-1H-isoindole-1,3(2H)-dione], 5,5'-bis[2-(2-naphthalenesulfonyl)oxy-1H-isoindole-1,3(2H)-dione], 5,5'-bis[2-(2-thienylsulfonyl)oxy-1H-isoindole-1,3(2H)-dione], 5,5'-bis[2-(2,1-naphthoquinoediazide-4-sulfonyl)oxy-1H-isoindole-1,3(2H)-dione], 5,5'-bis[2-(2,1-naphthoquinoediazide-5-sulfonyl)oxy-1H-isoindole-1,3(2H)-dione], 5,5'-bis[2-(4-N,N-dimethylaminonaphthalene-5-sulfonyl)oxy-1H-isoindole-1,3(2H)-dione] and 5,5'-bis[2-(quinoline-8-sulfbnyl)oxy-1H-isoindole-1,3(2H)-dione], and among others, a preferable one includes, for example, 5,5'-bis[2-nonafluorobutanesulfonyloxy-1H-isoindole-1,3(2H)-dione], 5,5'-bis[2-heptadecafluorooctanesulfonyloxy-1H-isoindole-1,3(2H)-dione], 5,5'-bis[2-(10-camphorsulfonyl)oxy-1H-isoindole-1,3(2H)-dione], 5,5-bis[2-(4-trifluoromethylphenylsulfonyl)oxy-1H-isoindole-1,3(2H)-dione], 5,5'-bis[2-(3-trifluoromethylphenylsulfonyl)oxy-1H-isoindole-1,3(2H)-dione], 5,5'-bis[2-(3,5-di-trifluoromethylphenylsulfonyl)oxy-1H-isoindole-1,3(2H)-dione] and 5,5'-bis[2-(pentafluorobenzenesulfonyl)oxy-1H-isoindole-1,3(2H)-dione].

The bisimidesulfonate compound of the present invention, shown by the general formula [4] is useful as an acid generator for a resist composition, and in particular, the compounds shown by the general formulae [11] and [12] are preferable, because high sensitivity is expected due to high acid generation efficiency responsive to radiation, when they are used as an acid generator for a resist composition.

The bisphthalimidesulfonate compound of the present invention, shown by the general formula [26] is also useful as an acid generator for a resist composition, and in particular, the compounds shown by the general formulae [13] and [14] are preferable, because high sensitivity is expected due to high acid generation efficiency responsive to radiation as well as high solubility in a solvent, when they are used as an acid generator for a resist composition.

The bisimidesulfonate compound, shown by the general formula [4] can be synthesized, for example, by the following methods [A], [B], [C], [D] and the like.

Namely, in the method [A], 1 mole of an acid anhydride shown by the following general formula [16]:

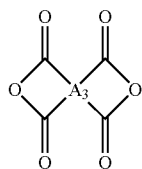

[16]

(wherein $A_3$ is the same as described above) and 1 to 5 mole parts of a hydroxylamine or a salt thereof (e.g. a hydrochloride salt and a sulfate salt) are dissolved in a solvent such as toluene, acetone, N,N-dimethylformamide and N,N-dimethylacetamide, in the presence of a basic compound such as pyridine, triethylamine and tributylamine, followed by reacting at 0 to 100° C. for 0.5 to 10 hours with stirring and post-treatment in accordance with a conventional method to obtain a bis(N-hydroxyimide) compound shown by the following general formula [17]:

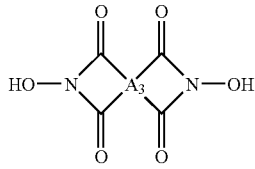

[17]

(wherein $A_3$ is the same as described above). Then, 1 mole of the obtained bis(N-hydroxyimide) compound and 1 to 5 mole parts of a sulfonylhalide compound shown by the following general formula [18]:

[wherein $X_1$ is a halogen atom (e.g. a fluorine atom, a chlorine atom, a bromine atom and an iodine atom); and $R^2$ is the same as described above] are dissolved in a suitable solvent (e.g. hydrocarbons such as cyclohexane; halogenated hydrocarbons such as methylene chloride, chloroform and dichloroethane; aromatic hydrocarbons such as benzene and toluene: ketones such as acetone, methyl ethyl ketone, methyl isobutyl ketone and cyclohexanone; ethers such as ethyl ether, dimethoxy ethane and 1,4-dioxane; and amides such as N,N-dimethylformamide and N,N-dimethylacetamide) in the presence of a basic compound such as pyridine, triethylamine, tripropylamine, tributylamine, trioctylamine, and 4-N,N-dimethylaminopyridine, followed by reacting at −10 to 120° C. for 0.5 to 10 hours with stirring and post-treatment in accordance with a conventional method to obtain the compound shown by the general formula [4].

In the method [B], 1 mole of an acid anhydride shown by the above-described general formula [16] and 2 to 6 mole parts of ammonia (aqueous ammonia) are mixed in a solvent such as water, methanol and ethanol, followed by reacting at 50 to 150° C. for 0.5 to 10 hours with stirring and post-treatment in accordance with a conventional method, to obtain a bisimide compound shown by the following general formula [19]:

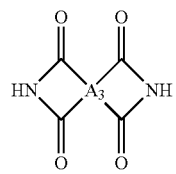

[19]

(wherein $A_3$ is the same as described above). Then, 1 mole part of the obtained bisimide compound and 2 to 5 mole parts of a halogenizing agent (e.g. halogens such as chlorine, bromine and iodine, and imides such as N-chlorosuccinimide, N-bromosuccinimide and N-iodosuccinimide) are mixed in a suitable solvent (e.g. halogenated hydrocarbons such as methylene chloride, chloroform and dichloroethane; ethers such as dimethoxy ethane and ethyl ether; and esters such as ethyl acetate), followed by reacting at −10 to 75° C. for 0.5 to 10 hours with stirring and post-treatment in accordance with a conventional method to obtain a bishaloimide compound shown by the following general formula [20].

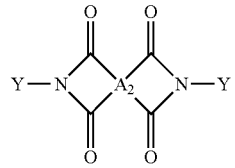

[20]

[wherein Y is a halogen atom (e.g. afluorine atom, a chlorine atom, a bromine atom and an iodine atom); $A_3$ is the same as described above]. Further, 1 mole of the obtained bishaloimide compound and 1 to 5 mole parts of a sulfonate shown by the following general formrmula [21]:

[21]

[wherein M is a metal atom (e.g. a sodium atom, a potassium atom, a lithium atom, a calcium atom, a barium atom, a magnesium atom, a copper atom, a silver atom and a zinc atom); n is an integer of 1 to 2; and $R^2$ is the same as described above] are mixed in a suitable solvent (e.g. alcohols such as methanol and ethanol; halogenated hydrocarbons such as methylene chloride and chloroform; aromatic hydrocarbons such as benzene and toluene; acetone, ethyl acetate, cyclohexane and water), followed by reacting at 0 to 100° C. for 0.5 to 10 hours with stirring and post-treatment in accordance with a conventional method to obtain the compound shown by the general formula [4].

In the method [C], 1 mole of the bis(N-hydroxyimide) compound shown by the general formula [17] obtained by the above-described method [A], 1 to 5 mole parts of a sulfonic acid shown by the following general formula [22]:

[22]

(wherein $R^2$ is the same as described above) and 1 to 5 mole parts of dicyclohexylcarbodiimide (DCC) are mixed in a suitable solvent (e.g. halogenated hydrocarbons such as methylene chloride and chloroform; esters such as ethyl acetate, methyl acetate and butyl acetate; ethers such as ethyl ether, isopropyl ether, dimethoxy ethane and propylenglycol dimethyl ether; and ketones such as acetone, methyl isobutyl ketone and cyclohexanone), followed by reacting at 0 to 100° C. for 0.5 to 10 hours with stirring and post-treatment in accordance with a conventional method to obtain the compound shown by the general formula [4].

In the method [D],1 mole of the bis(N-hydroxyimide) compound shown by the general formula [17] obtained by the above-described method [A] and 1 to 5 mole parts of a sulfonyl fluoride compound shown by the following general formula [23]:

[23]

(wherein $R^2$ is the same-as described above) or a sulfonic anhydride shown by the following general formula [24]:

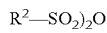
[24]

(wherein $R^2$ is the same as described above) are reacted at −10 to 100° C. for 0.5 to 10 hours with stirring in a suitable solvent (e.g. hydrocarbons such as cyclohexane; aromatic hydrocarbons such as benzene and toluene; and ethers such as ethyl ether and 1,2-dimethoxy ethane) in the presence of 1 to 10 mole parts of a basic compound (e.g. metal alkoxides such as sodium methoxide and potassium tert-butoxide; metal hydrides such as sodium hydride; amines such as triethylamine, tri-n-butylamine and tri-n-octylamine; and pyridine and 2,6-lutidine) followed by post-treatment in accordance with a conventional method to obtain the compound shown by the general formula,[4].

The bisphthalimidesulfonate compound shown by the general formula [26] can be obtained by the following [E], [F], [G], [H] methods and the like.

Namely, in the method [E], 1 mole of acid anhydride shown by the following general formula [27]:

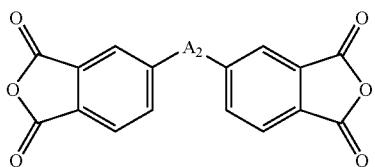
[27]

(wherein $A_2$ is the same as described above) and 1 to 5 mole parts of hydroxylamine or a salt thereof (e.g. a hydrochloride salt and a sulfate salt) are dissolved in a solvent such as toluene, acetone, N,N-dimethylformamide and N,N-dimethylacetamide, in the presence of a basic compound such as pyridine, triethylamine and tributylamine, followed by reacting at 0 to 100° C. for 0.5 to 10 hours with stirring and post-treatment in accordance with a conventional method to obtain a bis(N-hydroxy) phthalimide compound shown by the following general formula [25]:

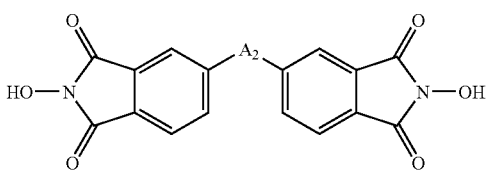
[25]

(wherein $A_2$ is the same as described above). The above-described reaction can also be carried out in a basic compound as a solvent. Then, 1 mole of the obtained bis(N-hydroxy)phthalimide compound and 1 to 5 mole parts of a sulfonylhalide compound shown by the following general formula [28]:

[28]

(wherein $R^4$ and $X_1$ are the same as described above) are dissolved in a suitable solvent (e.g. hydrocarbons such as cyclohexane; halogenated hydrocarbons such as methylene chloride, chloroform and dichloroethane; aromatic hydrocarbons such as benzene and toluene; ketones such as acetone, methyl ethyl ketone, methyl isobutyl ketone and cyclohexanone; ethers such as ethyl ether, dimethoxy ethane and 1,4,-dioxane; and amides such as N,N-dimethylformamide and N,N-dimethylacetamide) in the presence of a basic compound such as pyridine, triethylamine, tripropylamine, tributylamine, trioctylamine and 4-N,N-dimethylaminopyridine, followed by reacting at −10 to 120° C. for 0.5 to 10 hours with stirring and post-treatment in accordance with a conventional method to obtain a compound shown by the general formula [26].

In the method [F], 1 mole of an acid anhydride shown by the above-described general formula [27] or 1 mole part of a tetracarboxylic acid shown by the following general formula [29]

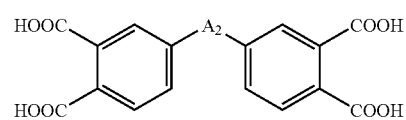
[29]

(wherein $A_2$ is the same as described above), [it can be obtained from o-xylene in accordance with a method disclosed in J. Am. Chem. Soc., 80, 1196 (1958) and the like.] and 2 to 6 mole parts of ammonia (aqueous ammonia) are mixed in a solvent such as water, methanol and ethanol, and reacted at, 50 to 300° C. for 0.5 to 10 hours with stirring, or 1 mole part of an acid anhydride shown by the above-described general formula [27] and 2 to 20 mole parts of a formamide are reacted at 50 to 150° C. for 0.5 to 10 hours with stirring without solvent or in a hydrocarbon solvent such as toluene and xylene, followed by post-treatment in accordance with a conventional method to obtain a bisphthalimide compound shown by the general formula [30]:

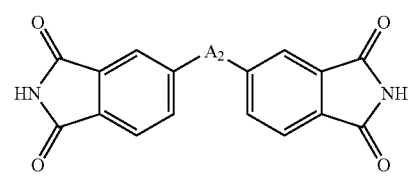
[30]

(wherein $A_2$ is the same as described above). Then, 1 mole of the obtained bisphthalimide compound and 2 to 5 mole parts of a halogenizing agent (e.g. halogens such as chlorine, bromine and iodine; and imides such as N-chloroscuccinimide, N-bromoscuccinimide and N-iodoscuccinimide) are mixed in a suitable solvent (e.g. halogenated hydrocarbons such as methylene chloride, dichloroethane, chloroform and carbon tetrachloride; ethers such as dimethoxyethane and ethyl, ether; esters such as ethyl acetate; and water) and in a basic compound (e.g. sodium hydroxide, potassium hydroxide, triethylamine, diethylamine, 2,6-lutidine and p-N,N-dimethylaniline), if necessary, followed by reacting at −10 to 75° C. for 0.01 to 10 hours with stirring and post-treatment in accordance with a conventional method to obtain a bishalophthalimide compound shown by the following general formula [31]:

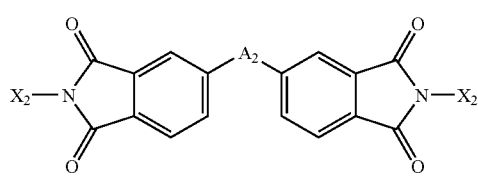

[wherein $X_2$ is a halogen atom (e.g. a fluorine atom, a chlorine atom, a bromine atom and an iodine atom); and $A_2$ is the same as described above]. Furthermore, 1 mole of the bishalophthalimide compound obtained and 1 to 5 mole parts of a sulfonate shown by the following general formula [32].

$$(R^4\text{—}SO_3)nM_1 \qquad [32]$$

(wherein $R^4$, $M_1$ and n are the same as described above) are mixed in a suitable solvent (e.g. alcohols such as methanol and ethanol; halogenated hydrocarbons such as methylene chloride and chloroform; aromratic hydrocarbons such as benzene and toluene; and acetone, ethyl acetate, cyclohexane and water), followed by reacting at 0 to 100° C. for 0.5 to 10 hours with stirring and post-treatment in accordance with a conventional method to obtain the compound shown by the general formula [26].

In the method [G], 1 mole of the bis(N-hydroxy)phthalimide compound shown by the general formula [25] obtained by the above-described method [E] and 1 to 5 mole parts of a sulfonic acid shown by the following general formula [33]:

$$R^4\text{—}SO_3H \qquad [33]$$

(wherein $R^4$ is the same as described above) and 1 to 5 mole parts of dicyclohexylcarbodiimide (DCC) are mixed in a suitable solvent (e.g. halogenated hydrocarbons such as methylene chloride and chloroform; esters such as ethyl acetate, methyl acetate and butyl acetate; ethers such as ethyl ether, isopropyl ether, dimethoxy ethane and propylene glycol dimethyl ether; ketones such as acetone, methyl isobutyl ketone and cyclohexanone), followed by reacting at 0 to 100° C. for 0.5 to 10 hours with stirring and post-treatment in accordance with a conventional method to obtain the compound shown by the general formula [26].

In the method [H], 1 mole of the bis(N-hydroxy)phthalimide compound shown by the general formula [25] obtained by the above-described method [E] and 1 to 5 mole parts of a sulfonylfluororide compound shown by the following general formula [34]:

$$R^4\text{—}SO_2F \qquad [34]$$

(wherein $R^4$ is the same as described above) or a sulfonic anhydride shown by the following general formula [35]:

$$(R^4\text{—}SO_2)_2O \qquad [35]$$

(wherein $R^4$ is the same as described above) are reacted at −10 to 100° C. for 0.5 to 15 hours with stirring in a suitable solvent (e.g. hydrocarbons such as pentane and cyclohexane; aromatic hydrocarbons such as benzene and toluene; ethers such as ethyl ether and 1,2-dimethoxyethane) in the presence of 1 to 10 mole parts of a basic compound (e.g. metal alkoxides such as sodium methoxide, sodium ethoxide and potassium tert-butoxide; metal hydrides such as sodium hydide; alkyl metals such as n-butyllithium and sec-butyllithium; amines such as triethylamine, tri-n-butylamine and tri-n-octylamine; and pyridine and 2,6-lutidine), followed by post-treatment in accordance with a conventional method to obtain the compound shown by the general formula [26].

The bisimide compound of the present invention, shown by the general formula [1], that is, a bisimidesulfonate compound shown by the general formula [4] and a bisphthalimidesulfonate compound shown by the general formula [26] is not only useful as a raw material of a polyimide compound or a cross-linking agent but also provides an excellent effect as an acid generator for a chemically amplified resist composition.

A chemically amplified resist composition using the bisimide compound of the present invention as an acid generator is roughly classified into, for example, (1) a positive resist composition comprising, as main solid components, at least one kind of alkali-soluble resin, at least one kind of dissolution-inhibiting resin or dissolution inhibitor, which turn alkali soluble through a chemical change in the presence of an acid, and an acid generator, (2) a positive resist composition comprising, as main solid components, at least one kind of resin which turns alkali-soluble through a chemical change in the presence of an acid and an acid generator, and (3) a negative resist composition comprising, as main solid components, at least one kind of alkali-soluble resin, at least one kind of cross-linkable compound which makes said resin hardly alkali-soluble through a chemical change by heating in the presence of an acid and an acid generator.

An amount of the bisimide compound shown by the general formula [1] to be used is generally 1 to 20 wt %, preferably 3 to 20 wt %, relative tog a base polymer such as the said alkali-soluble resin and dissolution-inhibiting resin which turns alkali-soluble through chemical change in the presence of an acid.

The alkali-soluble resin includes, for example, one shown by the following general formula [36]:

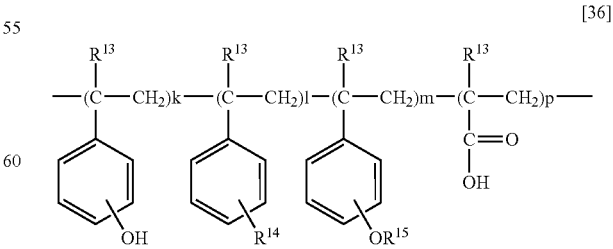

(wherein $R^{13}$s are each independently a hydrogen atom or a methyl group; $R^{14}$ is an alkyl group; $R^{15}$ is an acid labile group; l, m and p are each 0 or a natural number; k is a natural number, and provided that 1≧k≧0.8, 0.2≧l≧0, 0.2≧m≧0, 0.2≧p≧0, and k+l+m+p=1), and one shown by the following general formula [37]:

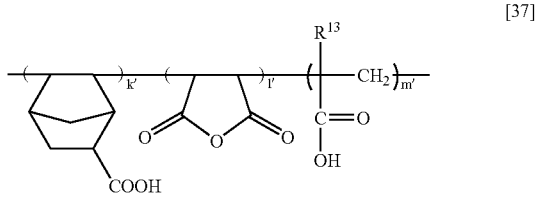

[37]

(wherein m' is 0 or a natural number; k' and l' are each a natural number, and provided that 0.9≧k'≧0.1, 0.9≧l'≧0.1, 0.9≧m'≧0, and k'+l'+m'=1; $R^{13}$ is the same as described above).

In the general formula [36], the alkyl group shown by $R^{14}$ may be straight chained, branched or cyclic, preferably straight chained or branched, and includes one having generally 1 to 6 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclpropyl goup, a cyclobutyl group, a cyclopentyl group and a cyclohexyl group.

The acid labile group shown by $R^{15}$ includes, for example, a tert-butyl group, a 1-methylcyclohexyl group, a 1-ethoxyethyl group, a 1-cyclohexyloxyethyl group, a tert-butoxycarbonyl group, a tetrahydropyranyl group, a trimethylsilyl group and a tert-butoxycarbonylmethy group.

The specific examples of the resin shown by the general formula [36] include, for example, poly(p-hydroxystyrene), poly(p-hydroxystyrene/styrene), poly(p-hydroxystyrene/styrene/acrylic acid), poly(p-hydroxystyrene/styrene/methacrylic acid), poly(p-hydroxystyrene/acrylic acid), poly(p-hydroxystyrene/methacrylic acid), poly(p-tert-butoxystyrene/p-hydroxystyrene) [composition ratio: 20↓/80↑], poly(p-tert-butoxycarbonyloxystyrene/p-hydroxystyrene) [composition ratio: 20↓/80↑], poly(p-tetrahydropyranyloxystyrene/p-hydroxystyrene) [composition ratio: 20↓/80↑], poly(p-trimethylsilyloxystyrene/p-hydroxystyrene) [composition ratio: 20↓/80↑], poly(p-tert-butoxycarbonylmethoxystyrene/p-hydroxystyrene) [composition ratio: 20↓/80↑], poly(p-isopropoxystyrene/p-hydroxystyrene) [composition ratio: 20↓/80↑] and poly(p-1-ethoxyethoxystyrene/p-hydroxystyrene) [composition ratio: 20↓/80↑].

The specific examples of the resin shown by the general formula [37] include, for example, poly(5-norbornene-2-carboxylic acid/maleic anhydride/acrylic acid) and poly(5-norbornene-2-carboxylic acid/maleic anhydride/methacrylic acid).

A weight-average molecular weight (Mw) of the alkali-soluble resin is generally 2,000 to 50,000, preferably 2,000 to 25,000, and molecular weight distribution (Mw/Mn) thereof is generally 1.0 to 3.0, preferably 1.0 to 2.0.

The dissolution-inhibiting resin which turns alkali-soluble through a chemical change in the presence of an acid includes, for example, one shown by the following general formula [38]:

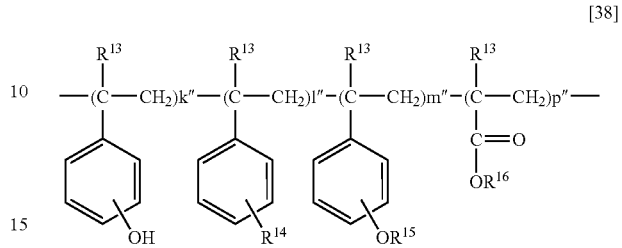

[38]

(wherein $R^{16}$ is an acid labile group; k", l", m" and p" are each 0 or a natural number, and provided that 0.8≧k"≧0, 0.5≧l"≧0, 1≧m"≧0, 1≧p"≧0, and k"+l"+m"+p"=1; and $R^{13}$, $R^{14}$ and $R^{15}$ are the same as described above), one shown by the following general formula [39]:

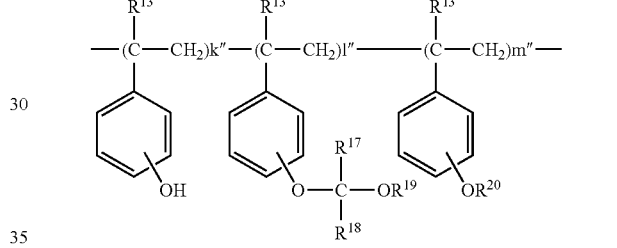

[39]

[wherein $R^{17}$ and $R^{18}$ are each independently a hydrogen atom or an alkyl group (except the case when both $R^{17}$ and $R^{18}$ are hydrogen atoms); $R^{19}$ is an alkyl group, a haloalkyl group, or an aralkyl group; $R^{20}$ is an acid labile group; k'" and m'" are each 0 or a natural number, and l'" is a natural number, and provided that 0.8≧k'"≧0, 1≧l'"≧0.2, 0.5≧m'"≧0.01, and k'"+l'"+m'"=1; and $R^{13}$ is the same as described above], one shown by the general formula [40]:

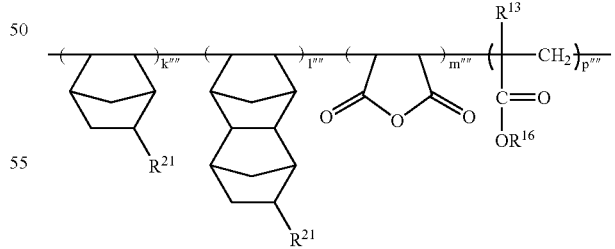

[40]

(wherein $R^{21}$ is a hydrogen atom or an alkoxycarbonyl group; k"", l"" and p"" are each 0 or a natural number and m"" is a natural number, and provided that 0.9≧k""≧0, 0.9≧l""≧0, 0.9≧m""≧0.1, 0.9≧p""≧0, and k""+l""+m""+p""=1; and $R^{13}$ and $R^{16}$ are the same as described above), and poly[p-1-ethoxyethoxystyrene/p-hydroxystyrene/p-1-oxyethoxystyrene (cross-linked with an alkylene chain, a cycloalkane or an aromatic ring)] {specifically including, for example, one shown by the general formula [41]:

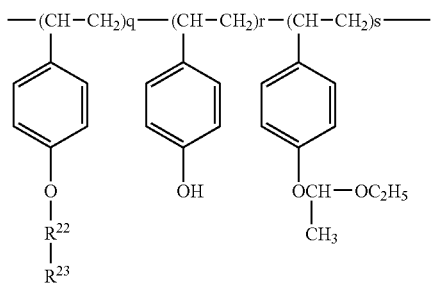

[wherein $R^{22}$ is a group shown by the following formulae;

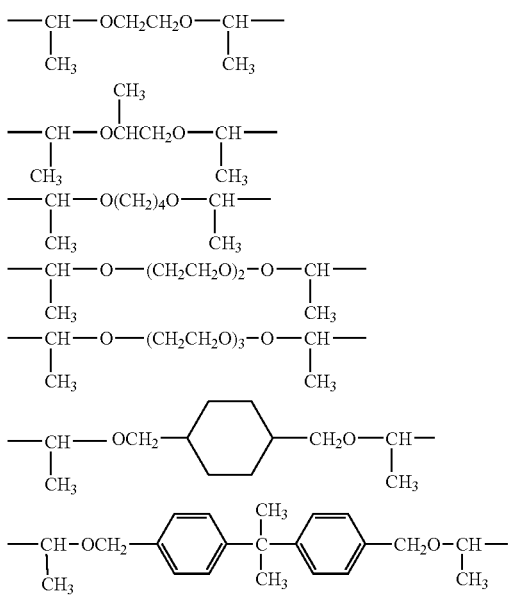

$R^{23}$ is a group derived from a polymer having a group shown by the following formula [42]:

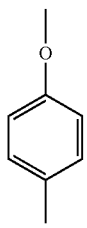

(wherein the oxygen atom is bonded to $R^{22}$); q, r and s are each a natural number, and provided that $0.4 \geq q > 0$, $0.9 \geq r \geq 0.4$ and $0.6 \geq s > 0$]}.

In the general formulae [38] and [40], the acid labile group shown by $R^{16}$ includes, for example, a tert-butyl group, a 1-methylcyclohexyl group, a 2-methyl-2-adamantyl group, a mevalonic lactonyl group and a 1-adamantyl group.

In the general formula [39], the alkyl group shown by $R^{17}$ and $R^{18}$ may be straight chained, branched or cyclic, and includes one having generally 1 to 6 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclopropyl group, a cyclobutyl group, a cyclopentyl group and a cyclohexyl group.

The alkyl group shown by $R^{19}$ may be straight chained, branched or cyclic, and includes one having generally 1 to 10 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 1,2-dimethylbutyl group, a 1-ethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cyclohexylmethyl group, a 2-cyclohexylethyl group, a cycloheptyl group, a cyclooctyl group, a cyclononyl group and a cyclodecyl group.

The haloalkyl group shown by $R^{19}$ may be straight chained, branched or cyclic, and includes one, wherein a part of or all of the hydrogen atoms of the alkyl group having generally 1 to 6 carbon atoms are substituted by a halogen atom (e.g. a fluorine atom, a chlorine atom, a bromine atom and an iodine atom), which is specifically exemplified by, for example, a fluoromethyl group, a chloromethyl group, a bromomethyl group, an iodomethyl group, a difluoromethyl group, a dichloromethyl group, a dibromomethyl group, a trifluoromethyl group, a trichloromethyl group, a triiodomethyl group, a tetrafluoroethyl group, a tetrachloroethyl group, a tetrabromoethyl group, a tetraiodoethyl group, a heptafluoropropyl group, a heptachloropropyl group, a heptabromopropyl group, a heptaiodopropyl group, a nonafluorobutyl group, a nonachlorobutyl group, a nonabromobutyl group, a nonaiodobutyl group, a perfluoropentyl group, a perchloropentyl group, a perbromopentyl group, a periodopentyl group, a perfluorohexyl group, a perchlorohexyl group, a perbromohexyl group, a periodohexyl group, a pentafluorocyclohexyl group, a pentachlorocyclohexyl group, a pentabromocyclohexyl group and a pentaiodocyclohexyl group.

The aralkyl group shown by $R^{19}$ includes one having generally 7 to 12 carbon atoms, which is specifically exemplified by, for example, a benzyl group, a phenethyl group, a phenylpropyl group, a phenylbutyl group, a phenylpentyl group, a phenylhexyl group and a 1-naphthylethyl group.

The acid labile group shown by $R^{20}$ includes, for example, a tert-butyl group, a 1-methylcyclohexyl group, a tert-butoxycarbonyl group, a tetrahydropyranyl group, a trimethylsilyl group and a tert-butoxycarbonylmethyl group.

In the general formula [40], the alkoxycarbonyl group shown by $R^{21}$ may be straight chained, branched or cyclic, and includes one having generally 2 to 7 carbon atoms, which is specifically exemplified by, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentylokycarboryl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a cyclopropyloxycarbonyl group, a cyclobutoxycarbonyl group, a cyclopentyloxycarbonyl group and a cyclohexyloxycarbonyl group.

In the general formula [41], the group derived from a polymer shown by $R^{23}$ includes, for example, one which turns alkali-soluble through a scission of cross-linked part by an action of a co-existing acid, which is specifically exemplified by, for example, one derived from the dissolution-inhibiting resin shown by the general formulae [38] and [39].

The specific examples of the dissolution-inhibiting resin shown by the general formula [38] include, for example, poly(p-hydroxystyrene/styrene/tert-butyl acrylate), poly(p-hydroxystyrene/styrene/1-methylcyclohexyl acrylate), poly (p-hydroxystyrene/styrene/2-methyl-2-adamantyl acrylate), poly(p-hydroxystyrene/styrene/tert-butyl methacrylate), poly(2-methyl-2-adamantyl acrylate/mevalonic lactone acrylate), poly (2-methyl-2-adamantyl methacrylate/mevalonic lactone methacrylate), poly(p-hydroxystyrene/2-methyl-2-adamantyl acrylate), poly(p-tert-butoxystyrene/p-hydroxystyrene) [composition ratio: 20↓/80↑], poly(p-tert-butoxycarbonyloxystyrene/p-hydroxystyrene) [composition ratio: 20↓/80↑], poly(p-tetrahydropyranyloxystyrene/p-hydroxystyrene) [composition ratio: 20↓/80↑], poly(p-tromethylsilyloxystyrene/p-hydroxystyrene) [composition ratio: 20↓/80↑], poly(p-tert-butoxycarbonylmethoxystyrene/p-hydroxystyrene) [composition ratio: 20↓/80↑], poly(p-1-ethoxyethoxystyrene/p-hydroxystyrene) [composition ratio: 20↓/80↑], poly(p-1-cyclohexyloxyethoxystyrene/p-hydroxystyrene) [composition ratio: 20↓/80↑], poly(p-1-(2-cyclohexylethoxy)ethoxystyrene/p-hydroxystyrene) [composition ratio: 20↓/80↑], poly(p-1-methoxy-1-ethoxyethoxystyrene/p-hydroxystyrene) [composition ratio: 20↓/80↑], poly(p-1-elthoxyethoxystyrene/p-hydroxystyrene/tert-butyl methacrylate), poly(p-1-ethoxyethoxystyrene/p-hydroxystyrene/1-methylcyclohexyl acrylate), poly (p-1-ethoxyethoxystyrene/p-hydroxystyrene/2-methyl-2-adamantyl acrylate), poly(p-1-ethoxyethoxystyrene/p-hydroxystyrene/1-adamantyl acrylate), poly(p-1-ethoxyethoxystyrene/p-hydroxystyrene/styrene), poly(p-1-ethoxyethoxystyrene/p-hydroxystyrene/p-methylstyrene), poly(p-1-cyclohexyloxyethoxystyrene/p-hydroxystyrene/tert-butyl acrylate), poly(p-1-cyclohexyloxyethoxystyrene/p-hydroxystyrene/tert-butyl methacrylate), poly(p-1-cyclohexyloxyethoxystyrene/p-hydroxystyrene/1-methylcyclohexyl acrylate), poly (p-1-cyclohexyloxyethoxystyrene/p-hydroxystyrene/2-methyl-2-adamantyl acrylate), poly(p-1-cyclohexyloxyethoxystyrene/p-hydroxystyrene/1-adamantyl acrylate), poly(p-1-cyclohexyloxyethoxystyrene/p-hydroxystyrene/styrene), poly(p-1-cyclohexyloxyethoxystyrene/p-hydroxystyrene/p-methylstyrene), poly(p-1-methoxy-1-ethoxyethoxystyrene/p-hydroxystyrene/tert-butyl acrylate), poly(p-1-methoxy-1-ethoxyethoxystyrene/p-hydroxystyrene/tert-butyl methacrylate), poly(p-1-methoxy-1-ethoxyethoxystyrene/p-hydroxystyrene/1-methylcyclohexyl acrylate), poly(p-1-methoxy-1-ethoxyethoxystyrene/p-hydroxystyrene/2-methyl-2-adamantyl acrylate), poly(p-1-methoxy-1-ethoxyethoxystyrene/p-hydroxystyrene/1-adamantyl acrylate), poly(p-1-methoxy-1-ethoxyethoxystyrene/p-hydroxystyrene/styrene), poly(p-1-methoxy-1-ethoxyethoxystyrene/p-hydroxystyrene/p-methylstyrene), poly(styrene/p-hydroxystyrene/p-trimethylsilyloxystyrene), poly(styrene/p-hydroxystyrene/tert-butyl acrylate), poly(styrene/p-hydroxystyrene/p-tert-butoxycarbonylmethoxystyrene), poly(p-tert-butoxystyrene/p-hydroxystyrene/tert-butyl methacrylate), poly(p-tert-butoxystyrene/p-hydroxystyrene/1-methylcyclohexyl acrylate), poly(p-tert-butoxystyrene/p-hydrokystyrene/2-methyl-2-adamantyl acrylate), poly(p-tert-butoxystyrene/p-hydroxystyrene/1-adamantyl acrylate), poly(p-tert-butoxystyrene/p-hydroxystyrene/styrene), poly (p-tert-butoxystyrene/p-hydroxystyrene/p-methylstyrene), poly(p-tert-butoxycarbonyloxystyrene/p-hydroxystyrene/tert-butyl methacrylate), poly(p-tert-butoxycarbonyloxystyrene/p-hydroxystyrene/1-methylcyclohexyl acrylate), poly (p-tert-butoxycarbonyloxystyrene/p-hydroxystyrene/2-methyl-2-adamantyl acrylate), poly(p-tert-butoxycarbonyloxystyrene/p-hydroxystyrene/1-adamantyl acrylate), poly(p-tert-butoxycarbonyloxystyrene/p-hydroxystyrene/styrene), poly(p-tert-butoxycarbonyloxystyrene/p-hydroxystyrene/p-methylstyrene), poly(p-tetrahydropyranyloxystyrenelp-hydroxystyrene/tert-butyl methacrylate), poly (p-tetrahydropyranyloxystyrene/p-hydroxystyrene/1-methylcyclohexyl acrylate), poly(p-tetrahydropyranyloxystyrene/p-hydroxystyrene/2-methyl-2-adamantyl acrylate), poly(p-tetrahydropyranyloxystyrene/p-hydroxystyrene/1-adamantyl acrylate), poly(p-tetrahydropyranyloxystyrene/p-hydroxystyrene/styrene), poly(p-tetrahydropyranyloxystyrene/p-hydroxystyrene/p-methylstyrene), poly(p-tert-butoxycarbonylmethoxystyrene/p-hydroxystyrene/tert-butyl methacrylate), poly(p-tert-butoxycarbonylmethoxystyrene/p-hydroxystyrene/1-methylcyclohexyl acrylate), poly(p-tert-butoxycarbonylmethoxystyrene/p-hydroxystyrene/2-methyl-2-adamantyl acrylate), poly(p-tert-butoxycarbonylmethoxystyrene/p-hydroxystyrene/1-adamantyl acrylate), poly(p-tert-butoxycarbonylmethoxystyrene/p-hydroxystyrene/styrene) and poly(p-tert-butoxycarbonylmethoxystyrene/p-hydroxystyrene/p-methylstyrene).

The specific examples of the dissolution-inhibiting resin shown by the general formula [39] include, for example, poly(p-1-ethoxyethoxystyrene/p-hydroxystyrene/p-tert-butoxystyrene), poly(p-1-ethoxyethokystyrene/p-hydroxystyrene/p-tert-butoxycarbonyloxystyrene), poly(p-1-ethoxyethoxystyrene/p-hydroxystyrene/p-tetrahydropyranyloxystyrene), poly(p-1-ethoxyethoxystyrene/p-hydroxystyrene/p-trimethylsilyloxystyrene), poly(p-1-ethoxyethoxystyrene/p-hydroxystyrene/p-tert-butyl acrylate), poly(p-1-ethoxyethoxystyrene/p-hydroxystyrene/p-tert-butoxycarbonylmethoxystyrene), poly(p-1-cyclohexyloxyethoxystyrene/p-hydroxystyrene/p-tert-butoxystyrene), poly(p-1-cyclohexyloxyethoxystyrene/p-hydroxystyrene/p-tert-butoxycarbonyloxystyrene), poly(p-1-cyclohexyloxyethoxystyrene/p-hydroxystyrene/p-tetrahydropyranyloxystyrene), poly(p-1-cyclohexyloxyethoxystyrene/p-hydroxystyrene/p-trimethylsilyloxystyrene), poly(p-1-cyclohexyloxyethoxystyrene/p-hydroxystyrene/p-tert-butoxycarbonylmethoxystyrene), poly(p-1-methoxy-1-ethoxyethoxystyrene/p-hydroxystyrene/p-tert-butoxystyrene), poly(p-1-methoxy-1-ethoxyethoxystyrene/p-hydroxystyrene/p-tert-butoxycarbonyloxystyrene), poly (p-1-methoxy-1-ethoxyethoxystyrene/p-hydroxystyrene/p-tetrahydropyranyloxystyrene), poly(p-1-methoxy-1-ethoxyethoxystyrene/p-hydroxystyrene/p-trimethylsilyloxystyrene), poly(p-1-methoxy-1-ethoxyethoxystyrene/p-hydroxystyrene/p-tert-butoxycarbonylmethoxystyrene), poly(p-1-methoxy-1-ethoxyethoxystyrene/p-hydroxystyrene/p-isopropoxystyrene) and poly(p-1-methoxy-1-ethoxyethoxystyrene/p-hydroxystyrene/p-pivaloyloxystyrene).

The specific examples of the dissolution-inhibiting resin shown by the general formula, [40] include, for example, poly(tert-butyl 5-norbornene-2-carboxylate/maleic anhydride/cyclohexyl acrylate), poly(tert-butyl 1,2,3,4,4a,5,8,8a-octahydro-1,4:5,8-dimethanonaphthalene-2-carboxylate/maleic anhydride), poly(tert-butyl 1,2,3,4,4a,5,8,8a-octahydro-1,4:5,8-dimethanonaphthalene-2-carboxylate/maleic anhydride/methyl acrylate), poly(tert-butyl 1,2,3,4,4a,5,8,8a-octahydro-1,4:5,8-dimethanonaphthalene-2-carboxylate/maleic anhydride/5-norbornene-2-carbonitrile) and poly(tert-butyl 1,2,3,4,4a, 5,8,8a-octahydro-1,4:5,8-dimethanonaphthalene-2-carboxylate/maleic anhydride/methyl 5-norbornene-2-carboxylate).

A weight-average molecular weight (Mw) of the dissolution-inhibiting resin which turns alkali-soluble through a chemical change in the presence of an acid is generally 3,000 to 50,000, preferably 5,000 to 25,000, and molecular weight distribution (Mw/Mn) thereof is generally 1.0 to 3.0, preferably 1.0 to 2.0.

The specific examples of solubility inhibitors which turns alkali-soluble through a chemical change in the presence of an acid include, for example, 2,2'-bis(4-tert-butoxyphenyl)propane, 2,2,-bis(4-tert-butoxycarbonyloxyphenyl)propane, 2,2'-bis(4-tetrahydropyranyloxyphenyl)propane, 2,2'-bis[4-(1-ethoxyethoxy)phenyl]propane, 2,21-bis(4-tert-butoxycarbonylmethoxyphenyl)propane, 4,4',4"-tris(4-tert-butoxyphenyl)methane, 4,4',4"-tris(4-tert-butoxycarbonyloxyphenyl)methane, 4,4',4"-tris(4-tetrahydropyranyloxyphenyl)methane, 4,4',4"-tris[4-(1-ethoxyethoxy)phenyl]methane, 4,4',4"-tris(4-tert-butoxycarbonylmethoxyphenyl)methane, α,α,α'-tris(4-tert-butoxyphenyl)-1-ethyl-4-isopropylbenzene, α,α,α'-tris(4-tert-butoxycarbonyloxyphenyl)-1-ethyl-4-isopropylbenzene, α,α,α'-tris(4-tetrahydropyranyloxyphenyl)-1-ethyl-4-isopropylbenzene, α,α,α'-tris[4-(1-ethoxyethoxy)phenyl]-1-ethyl-4-isopropylbenzene, α,α,α'-tris(4-tert-butoxycarbonylmethoxyphenyl)-1-ethyl-4-isopropylbenzene, 1,1,1-tris(4-tert-butoxyphenyl)ethane, 1,1,1-tris(4-tert-butoxycarbonyloxyphenyl)ethane, 1,1,1-tris(4-tetrahydropyranyloxyphenyl)ethane, 1,1,1-tris[4-[4-(1-ethoxyethoxy)phenyl]ethane, 1,1,1-tris(4-tert-butoxycarbonylmethoxyphenyl)ethane, 1,1,1-tris(4-trimethylsilyloxyphenyl)ethane, 3,4-dihydro-4-[2,4-di-(4-tert-butoxyphenyl)]-7-(4-tert-butoxyphenyl)-2,2,4-trimethyl-2H-benzo-1-pyran, 3,4-dihydro-4-[2,4-di-(4-tert-butoxycarbonyloxyphenyl)]-7-(4-tert-butoxycarbonyloxyphenyl)-2,2,4-trimethyl-2H-benzo-1-pyran, 3,4-dihydro-4-[2,4-di-(4-tetrahydropyranyloxyphenyl)]-7-(4-tetrahydropyranyloxyphenyl)-2,2,4-trimethyl-2H-benzo-1-pyran, 3,4-dihydro-4-[2,4-di-[4-(1-ethoxyethoxy)phenyl]]-7-[4-(1-ethoxyethoxy)phenyl]-2,2,4-trimethyl-2H-benzo-1-pyran, 3,4-dihydro-4-[2,4-di-(4-tert-butoxycarbonylmethoxyphenyl)]-7-(4-tert-butoxycarbonylmethoxyphenyl)-2,2,4-trimethyl-2H-benzo-1-pyran, 3,4-dihydro-4-[2,4-di-(4-trimethylsilyloxyphenyl)]-7-(4-trimethylsilyloxyphenyl)-2, 2,4-trimethyl-2H-benzo-1-pyran, tert-butyl 2,2-bis(4-tert-butoxyphenyl)pentanoate, tert-butyl 2,2-bis(4-tert-butoxycarbonyloxyphenyl)pentanoate, tert-butyl 2,2-bis(4-tetrahydropyranyloxyphenyl)pentanoate, tert-butyl 2,2-bis [4-(1-ethoxyethoxy)phenyl]pentanoate and tert-butyl 2,2-bis(4-tert-butoxycarbonylmethoxyphenyl) pentanoate. They may be used alone or in a suitable combination of two or more kinds thereof.

An amount of these compounds to be used is generally 0.1 to 30 wt %, preferably 0.5 to 20 wt %, relative to a base polymer.

The cross-linkable compound which makes a resin hardly alkali-soluble through a chemical change by heating in the presence of an acid, include, for example, 2,4,6-tris(methoxymethyl)amino-1,3,5-s-triazine, 2,4,6-tris(ethoxymethyl)amino-1,3,5-s-triazine, tetramethoxymethyl glycol urea, tetramethoxymethyl urea, 1,3,5-tris(methoxymethoxy)benzene, 1,3,5-tris(isopropoxymethoxy)benzene, α,α,α'-tris(isbpropoxymethoxyphenyl)-1-ethyl-4-isopropylbenzene, α,α,α'-tris(methoxymethoxyphenyl)-1-ethyl-4-isopropylbenzene, CY-179 (a trade name of a product from Ciba Geigy Ltd.). They may be used alone or in a suitable combination of two or more kinds thereof.

An amount of these cross-linkable compounds to be used is generally 5 to 50 wt %, preferably 10 to 35 wt %, relative to a base polymer.

With regard to the bisimide compound shown by the general formula [1], at least one kind of said compound may be used as an acid generator, but they may also be used in combination with at least one kind of conventional acid generator including, for example, various diazosiulfone compounds, various sulfonium salts, various iodonium salts and various pyrogalloltrisulfonate compounds.

In a chemically amplified resist composition, a solvent and a basic compound are used, along with a surfactant, a UV absorber, an acid compound including anorganic carboxylic acid, if necessary, in addition to the above-described solid components (the resin, the bisimide compound shown by the general formula [1], the dissolution-inhibiting agent and the cross-linking-agent).

The specific examples of the solvent include, for example, methylcellosolve acetate, ethyl cellosolve acetate, propylene glycol monomethyl ether, propylene glycol monomethyl ether acetate, propyleneo glycol monoethyl ether acetate, methyl lactate, ethyl lactate, propyl lactate, 2-ethoxyethyl acetate, methyl pyruvate, ethyl pyruvate, methyl 3-methoxypropionate, ethyl 3-methoxypropionate, N,N-dimethylformamide, N,N-dimethylacetamide, cyclohexanone, methyl ethyl ketone, 2-heptanone, β-propiolactone, β-butyrolactone, γ-butyrolactone, γ-valerolactone, δ-valerolactone, 1,4-dioxane, diethylene glycol monomethyl ether, diethylene glycol dimethyl ether, ethylene glycol monoisopropyl ether and N-methyl-2-pyrrolidone. They may be used alone or in a suitable combination of two or more kinds thereof.

An amount of these solvents to be used is generally 3 to 25 parts by weight, preferably 3 to 20 parts, by weight, relative to 1 part by weight of the total solid components in any type of resist.

The basic compound is used to adjust sensitivity and the like, and specifically includes, for example, pyridine, picoline, triethylamine, tri-n-butylamine, tri-n-octylamine, dioctylmethylamine, dicyclohexylmethylamine, N-methylpyrrolidine, N-methylpiperidine, 4-N,N-dimethylaminopyridine, triethanolamine, triisopropanolamine, dimethyldodecylamine, dimethylhexadecylamine, tribenzylamine, tris[2-(2-methoxyethoxy)ethyl]amine, tetramethylammonium hydroxide, tetraethylammonium hydroxide, tetra-n- butylammonium hydroxide, polyvinylpyridine and poly(vinylpyridine/methyl methacrylate). They may be used alone or in a suitable combination of two or more kinds thereof.

The specific examples of the surfactant optionally used include, for example, a fluorine-containing nonionic type surfactant such as "Fluorad" (a trade name of a product from Sumitomo 3M, Ltd.), "Surflon" (a trade name of a product from Asahi Glass Co., Ltd.), "Unidyne" (a trade name of a product from Daikin Ind., Ltd.), "Megafac" (a trade name of a product from Dainippon Ink & Chem., Inc.) and "Eftop" (a trade name of a product from Tohkem Products Corp.), polyethylene glycol, polypropylene glycol and polyoxyethylene cetyl ether. They may be used alone or in a suitable combination of two or more kinds thereof.

The specific examples of the UV absorber optionally used include, for example, 9-diazofluorenone, 9-(2-methoxyethoxymethyl)anthracene, 9-(2-ethoxyethoxymethyl)-anthracene, 9-fluorenone, 2-hydroxycarbazole, o-naphthoquinonediazide derivatives and 4-diazo-1,7-diphenylpentane-3,5-dione. They may be used alone or in a suitable combination of two or more kinds thereof.

The acid compounds including the organic carboxylic acid optionally used include, for example, salicylic acid, m-hydroxybenzoic acid, p-hydroxybenzoic acid, o-acetylbenzoic acid, diphenolic acid, phthalic acid, succinic acid, malonic acid, salicylaldehyde, succinimide, phthalimide, saccharin and ascorbic acid. They maybe used alone or in a suitable combination of two or more kinds thereof.

An amount of the basic compound or the optionally used surfactant, UV absorber and acid compound including the organic carboxylic acid to be used is each generally 0.000001 to 1 wt %, preferably 0.00001 to 1 wt %, relative to the base polymers in any type of resist.

The method for pattern formation using a chemically amplified resist composition containing the bisimide compound shown by the general formula [1] as an acid generator is, for example, as follows.

Namely, a resist composition of the present invention is spin-coated on a semiconductor substrate such as a silicon wafer, followed by pre-baking at 70 to 150° C. for 60 to 120 sec. on a hot plate to obtain a resist film with 0.1 to 1.0 μm thickness. Then said resist film is irradiated with radio active rays to form an objective pattern, followed by baking (PEB) at 70 to 150° C. for 60 to 120 sec. on a hot plate and developing using an alkaline developing solution for 30 to 120sec, by, for example, a spraying method, a paddle method or a dip method, and washing with water to form a desired resist pattern.

The alkaline developing solution includes an aqueous solution dissolving at least one kind of alkaline compound including, for example, inorganic alkalis such as sodium hydroxide, potassium hydroxide and ammonia; organic alkalis such as triethanolamine, choline and tetraalkylammonium hydroxide, in an amount of generally 0.01 to 20 wt %, preferably 1 to 5 wt %, and among others, an aqueous solution of tetraalkylammonium hydroxide is preferable.

Further, in the developing solution consisting of said aqueous alkaline solution, an aqueous organic solvent such as methanol and ethanol, and a surfactant may be added appropriately.

A chemically amplified resist composition containing the compounds of the present invention, that is, the bisimidesulfonate compound shown by the general formula [4] and the bisphthalimidesulfonate compound shown by the general formula [26] as an acid generator generates an acid in accordance with the following schemes [1] and [2]in an area irradiated.

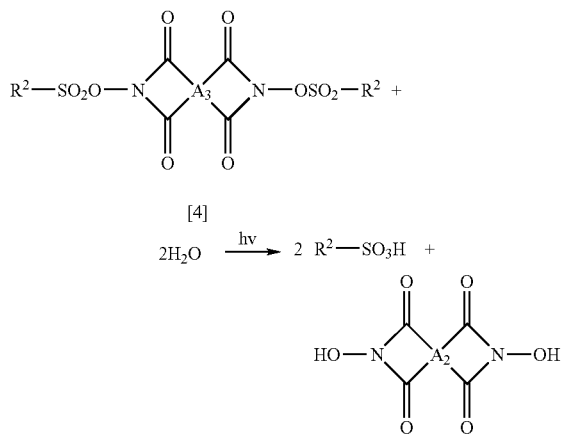

(wherein $R^2$ and $A_3$ are the same as described above),

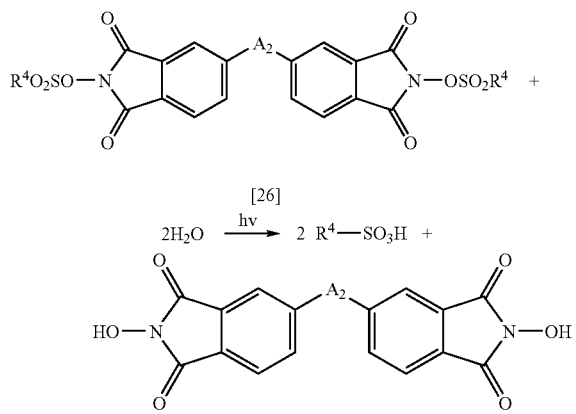

(wherein R and $A_2$ are the same as described above).

When a positive resist composition is used, a chemical change shown by the following scheme [3] occurs by, for example, heating, if necessary, in the presence of an acid generated, thereby the irradiated area turns soluble in an alkaline developing solution, and forms a positive-resist pattern (an elimination reaction of the acid labile group).

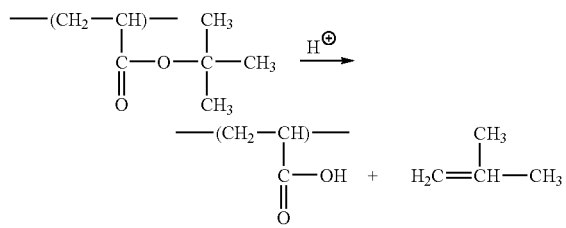

While, when a negative resist composition is used, a chemical change shown by the following scheme [4] occurs by, for example, heating, if necessary, in the presence of an acid generated, thereby the irradiated area turns hardly soluble in an alkaline developing solution, and form a negative resist pattern (a cross-linking reaction of the resin).

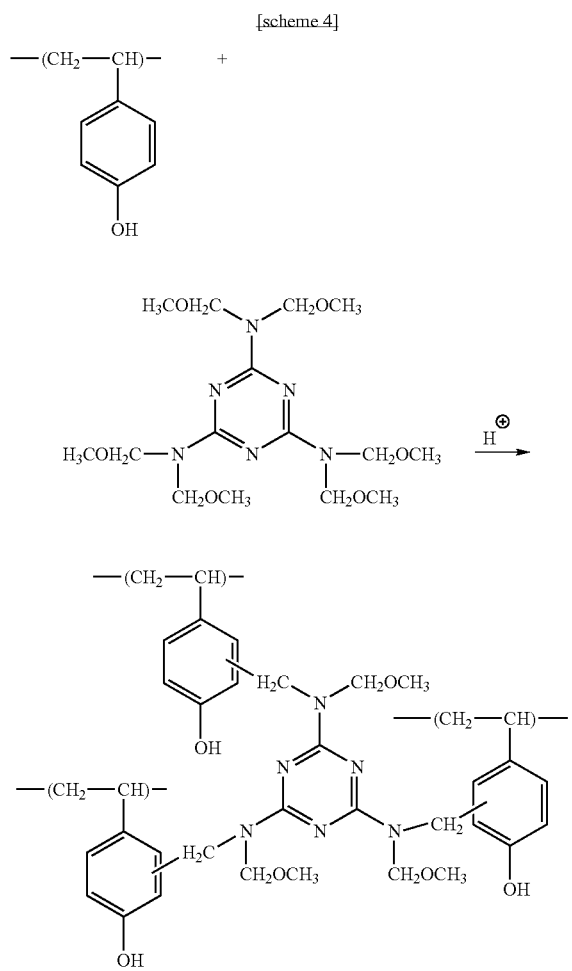

[scheme 4]

Since the bisimide compound of the present invention, shown by the general formula [1] has high solubility in a resist solvent, use of said compound as an acid generator for a chemically amplified resist composition can generate an acid homogeneously and in high sensitivity, without causing a problem such as easy formation of fine particles due to low solubility in a solvent, observed in using an acid generator such as a conventional sulfonium salt.

In addition, a chemically amplified resist composition containing the bisimide compound of the present invention can easily generate an acid in response to various radioactive rays such as i-line (365 nm), KrF excimer laser (248 nm), ArF excimer laser (193 nm), $F_2$ laser (157 nm), EUV (1 to 30 nm bond), electron beams and X-rays, and thus provides high sensitivity, high resolution and superior pattern profile.

Furthermore, the bisimide compound of the present invention is useful not only for said resist composition, but also for a chemically amplified resist composition for i-line, using a photosensitive polyimide resin.

Furthermore, the bis(N-hydroxy)phthalimide compound of the present, invention, shown by the general formula [25], is useful not only as a synthesis intermediate of the bisphthalimidesulfonate compound of the present invention, shown by the general formula [26], but also as, for example, a raw material for synthesizing a heat resistant polymer such as a cross-linking agent for a polyimide resin, a functional organic material such as synthetic intermediate for a photosensitive compound, and a functional material in biochemical fields such as peptide synthesis.

In the following, the present invention will be explained in further detail referring to Examples, Reference Examples and Comparative Examples, but the present invention is not limited thereto by any means.

EXAMPLE

Reference Example 1

Synthesis of tetrahydro-2,5-dihydroxycyclobuta-[1, 2-c:3,4-c'] dipyrrole-1,3,4,6(2H,5H)-tetrone In 210 ml of pyridine solution dissolving 15.3 g (0.22 mol) of hydroxylamine hydrochloride, 19.6 g (0.10 mol) of cyclobutane-1,2,3,4-tetracarboxylic dianhydride, obtained from maleic anhydride by photoreaction in accordance with the method disclosed in JP-A-59-212495, was added at room temperature, and the solution was reacted at 90° C. for 15 minutes with stirring. After completion of the reaction, the obtained reaction solution was concentrated under reduced pressure, and 210 ml of an aqueous solution of 6% acetic acid was poured to the resulting residue, followed by filtering precipitated crude crystalline substance, washing with water and drying under reduced pressure to obtain 17.0 g of tetrahydro-2,5-dihydroxycyclobuta[1,2-c:3,4-c'] dipyrrole-1,3,4,6(2H,5H)-tetrone as colorless powder crystal.

$^1$HNMR (DMSO-$d_6$) δ ppm: 3.38-3.40(4H,; d, CH×4); 11.09(2H, s, OH×2)

Reference Example 2

Synthesis of 3a,4,4a,7a,8,8a-hexahydro-2,6-dihydroxy-4,8-ethenobenzo[1,2-c:4,5-c']dipyrrole-1,3,5,7 (2H,6H)-tetrone The similar procedure as in Reference Example 1 was conducted except that 24.8 g (0.10 mol) of bicycle[2,2,2] oct-7-ene-2,3,5,6-tetracarboxylic dianhydicide was used instead of cyclobutane-1,2,3,4-tetracarboxylic dianhydride in Reference Example 1, to obtain 16.5 g of 3a,4,4a,7a,8, 8a-hexahydro-2,6-dihydroxy-4,8-ethenobenzo[1,2-c:4,5-c'] dipyrrole-1,3,5,7(2H,6H)-tetrone as colorless powder crystal.

$^1$HNMR (DMSO-$d_6$) δ ppm: 3.31-3.37(6H, m, CH×6), 6.08-6.09(2H, d, —CH═×2), 10.76(2H, s, OH×2)

Reference Example 3

Synthesis of 2,6-dihydroxybenzo[1,2-c:4,5-c']dipyrrole-1,3,5,7(2H,6H)-tetrone

The similar procedure as in Reference Example 1 was conducted except that 21.8 g (0.10 mol) of pyromellitic anhydride was used instead of cyclobutane-1,2,3,4-tetracarboxylic dianhydride in Reference Example 1, to obtain 24.0 g of 2,6-dihydroxybenzo[1,2-c:4,5-c'] dipyrrole-1,3,5,7(2H, 6H)-tetrone as orange powder crystal.

$^1$HNMR (DMSO-$d_6$) δ ppm: 8.13(2H, s, pyromellitic ring H×2), 11.16(2H, s, OH×2)

Reference Example 4

Synthesis of N-10-camphorsulfonyloxy-5-norbornene-2,3-dicarboxyimide

In 20 ml of acetone, 1.25 g (0.007 mol) of N-hydroxy-5-norbornene-2,3-dicarboxyimide and 2.01 g (0.008 mol) of 10-camphorsulfonyl chloride were suspended, then 0.81 g, (0.008 mol) of triethylamine was added dropwise thereto at room temperature, and the suspension was reacted for 2 hours with stirring. After completion of the reaction, the obtained reaction solution was poured into 100 ml of water for crystallization, followed by filtering precipitated crystal thus obtained, washing with water and drying to obtain crude crystal. Then, the crude crystal was recrystallized from a mixed solvent of ethyl acetate/ethyl ether to obtain 1.8 g of N-10-camphorsulfonyloxy-5-norbornene-2,3-dicarboxyimide as colorless prism crystal.

Mp.: 163-165° C.

$^1$HNMR (CDCl$_3$) δ ppm: 0.90(3H, s, CH$_3$), 1.11(3H, s, CH$_3$), 1.46-1.54(2H, m, H—C—H and bridged alicyclic H), 1.77-1.79(2H, m, H—C—H and bridged alicyclic H), 1.93-1.98(1H, d, bridged alicyclic H), 2.07-2.13(2H, m, bridged alicyclic H×2), 2.30-2.42(2H, m, bridged alicyclic H×2), 3.32(2H, bs, bridged alicyclic H×2), 3.46(2H, bs, bridged alicyclic H×2), 3.54-3.58(1H, d, H—C—H—SO$_3$), 3.91-3.95(1H, d, H—C—H—SO$_3^-$), 6.17-6.20(2H, d, —CH=×2)

Reference Example 5

Synthesis of N-pentafluorobenzenesulfonyloxy-5-norbornene-2,3-dicarboxyimide

In 10 ml of acetone, 0.63 g (0.0035 mol) of N-hydroxy-5-norbornene-2,3-dicarboxyimide and 1.07 g (0.004 mol) of pentafluorobenzenesulfonyl chloride were dissolved, then 0.40 g (0.004 mol) of triethylamine was added dropwise thereto at room temperature, and the solution was reacted for 2 hours with stirring. After completion of the reaction, the obtained reaction solution was poured into 50 ml of water for crystallization, followed by filtering precipitated crystal thus obtained, washing with water and drying to obtain crude crystal. Then, the crude crystal was recrystallized from a mixed solvent of ethyl acetate/ethyl ether to obtain 0.8 g of N-pentafluorobenzenesulfonyloxy-5-norbornene-2, 3-dicarboxyimide as colorless prism crystal.

Mp.: 153-155° C.

$^1$HNMR (CDCl$_3$) δ ppm: 1.49-1.51(1H, d, H—C—H) 1.78-1.81(1H, d, H—C—H), 3.29-3.30(2H, d, bridged alidyclic H×2), 3.45(2H, s, bridged alicyclic H×2), 6.16(2H; S, —CH=×2)

Reference Example 6

Synthesis of 2,6-bis(methanesulfonyloxy)benzo[1,2-c:4, 5-c'] dipyrrole-1,3,5,7(2H,6H)-tetrone In 1.5 ml of pyridine and 10 ml of N,N-dimethylacetamide, 1.00 g (0.004 mol) of 2,6-dihydroxybenzo[1,2-c:4,5-c']dipyrrole-1,3,5,7(2H,6H)-tetrone, obtained in Reference Example 3, was suspended, then 2.94 g (0.012 mol) of methanesulfonyl chloride was added dropwise thereto at room temperature, and the suspension was reacted for 1 hour with stirring. After completion of the reaction, the obtained reaction solution was poured into 150 ml of water for crystallization, followed by filtering precipitated crude crystal thus obtained, washing with water and drying to obtain crude crystal. Then, the crude crystal was recrystallized from N,N-dimethylacetamide to obtain 1.1 g of 2,6-bis (methanesulfonyloxy)benzo[1,2-c:4,5-c']dipyrrole-1,3,5,7 (2H,6H)-tetrone as colorless powder crystal.

Mp.: 300° C. or more $^1$HNMR (DMSO-d$_6$) δ ppm: 8.47(2H, s, pytomellitic ring H×2)

Reference Example 7

Synthesis of 3a,4,4a,7a,8,8a-hexahydro-2,6-bis(n-butanesulfonyloxy)-4,8-ethenobenzo [1,2-c:4,5-c'] dipyrrole-1,3,5,7(2H, 6H)-tetrone In 1.5 ml of pyridine and 10 ml of N,N-dimethylacetamide, 1.11 g (0.004 mol) of 3a,4,4a,7a,8,8a-hexahydro-2,6-dihydroxy-4,8-ethenobenzo[1,2-c:4,5-c']dipyrrole-1,3,5,7 (2H,6H)-tetrone, obtained in Reference Example 2, was dissolved, then 2.94 g (0.012 mol) of n-butanesulfonyl chloride was added dropwise thereto at room temperature, and the solution was reacted for 1 hour with stirring. After completion of the reaction, the obtained reaction solution was poured into 150 ml of water for crystallization, followed by filtering precipitated crude crystal, washing with water and drying to obtain crude crystal. Then, the crude crystal thus obtained was recrystallized from ethyl acetate to obtain 1.1 g of 3a,4i4a,7a,8,8a-hexahydro-2,6-bis(n-butanesulfonyloxy)-4,8-ethenobenzo[1,2-c:4,5-c']dipyrrole-1,3,5,7(2H, 6H)-tetrone as colorless flaky crystal.

Mp.: 239-241° C.

$^1$HNMR (DMSO-d$_6$) δ ppm: 0.88-0.92(6H, t, CH$_3$×2), 1.38-1.44(4H, q, CH$_2$×2), 1.79-1.83.(4H, m, CH$_2$×2), 3.43 (6H, s, CH×6), 3.61-3.65(4H, m, CH$_2$×2), 6.18(2H, s, —CH=×2)

Example 1

Synthesis of tetrahydro-2,5-bis(3-trifluoromethylphenylsulfonyloxy) cyclobuta [1,2-c:3,4-c']dipyrrole-1,3,4,6(2H,5H)-tetrone In 1.5 ml of pyridine and 10 ml of N,N-dimethylacetamide, 0.90 g (0.004 mol) of tetrahydro-2,5-dihydroxycyclobuta[1,2-c:3,4-c']dipyrrole-1,3,4,6(2H,5H)-tetrone, obtained in Reference Example 1, was suspended, then 2.94 g (0.012 mol) of 3-trifluoromethylbenzenesulfonyl chloride was added dropwise thereto at room temperature, and the suspension was reacted for 1 hour with stirring. After completion of the reaction, the obtained reaction solution was poured into 150 ml of water for crystallization, followed by filtering precipitated crude crystal, washing with water and drying to obtain crude crystal. Then, the crude crystal was recrystallized from a mixed solvent of methylene chloride/acetone to obtain 1.5 g of tetrahydro-2,5-bis(3-trifluoromethylphenylsulfonyloxy)cyclobuta[1,2-c:3,4-c']dipyrrole-1,3,4,6(2H,5H)-tetrone as colorless prism crystal (yield: 58.4%)

Mp.: 245-247° C.

$^1$HNMR (DMSO-d$_6$) δ ppm: 3.58(4H, s, CH×4), 7.92-8.01(2H, t, aromatic ring H×2), 8.31-8.34(2H, d, aromatic ring H×2), 8.39-8.43(4H, t, aromatic ring H×4)

IR(KBr-Disk) ν cm$^{-1}$: 3076, 3017, 1765(C=O), 1327 (SO$_2$O), 1196(SO$_2$O)

MS(m/z): 641(M$^+$)

Examples 2 to 5 Synthesis of the Compounds Shown by the General Formula [10] (the Ones Wherein Tetra-valent Alicyclic Hydrocarbon Groups Are Derived from a Cyclobutane Ring)

The similar procedures as in Example 1 were conducted except that various sulfonyl chlorides were used instead of 3-trifluoromethylbenzenesulfonyl chloride used in Example 1, desired bisimidesulfonate compounds were obtained. The results are shown in Table 1.

TABLE 1

| Example | $R^7$ | Shape (cryst. solvent) Physical property | $^1$H NMR (DMSO-$d_6$) (δ ppm), IR (KBr-Disk) (ν cm$^{-1}$), and others |
|---|---|---|---|
| 2 | n-butyl | colorless flaky crystal (MeCN) Mp.: 278° C. | $^1$HNMR: 0.89-0.93 (6 H, t, $CH_3$ × 2), 1.40-1.46 (4 H, q, $CH_2$ × 2), 1.84-1.88 (4 H, m, $CH_2$ × 2), 3.72 (4 H, s, CH × 4), 3.74-3.78 (4 H, m, $CH_2$ × 2) |
| 3 | p-methyl-phenyl | colorless powder crystal (DMAc) Mp.: ≧300° C. | $^1$HNMR: 2.46 (6 H, s, $CH_3$ × 2), 3.53 (4 H, s, CH × 4), 7.53-7.55 (2 H, d, aromatic ring H × 2), 7.94-7.96 (2 H, d, aromatic ring H × 2) IR: 3007, 1796 (C=O), 1750 (C=O), 1392 ($SO_2$O), 1179 ($SO_2$O) |
| 4 | 2,5-dichloro-phenyl | pale yellow prism crystal (DMAc) Mp.: 289° C. | $^1$HNMR: 3.57 (4 H, s, CH × 4), 7.88-7.91 (2 H, d, aromatic ring H × 2), 7.95-7.98 (2 H, m, aromatic ring H ×2), 8.01-8.09 (2 H, d, aromatic ring H × 2) |
| 5 | 10-camphor | colorless prism crystal (EtOAc/MeCN) Mp.: 210° C. | $^1$HNMR: 0.84 (6 H, s, $CH_3$ × 2), 1.04 (6 H, s, $CH_3$ × 2), 1.47-1.49 (2 H, m, bridged alicyclic H × 2), 1.67-1.70 (2 H, m, bridged alicyclic H × 2), 1.96-2.01 (4 H, m, bridged alicyclic H × 4), 2.11-2.13 (2 H, t, bridged alicyclic H × 2), 2.21-2.23 (2 H, m, bridged alicyclic H × 2), 2.38-2.42 (2 H, m, bridged alicyclic H × 2), 3.69-3.80 (4 H, dd, CH × 4), 3.86-3.90 (2 H, d, H—C—H × 2), 3.96-4.00 (2 H, d, H—C—H × 2), IR: 2980, 2946, 2892, 1757 (C=O), 1395 ($SO_2$O), 1188 ($SO_2$O) MS (m/z): 653 ($M^+$—H) |

* MeCN: acetonitrile, DMAc: N,N-dimethylacetamide, EtOAc: ethyl acetate

Example 6

Synthesis of 3a,4,4a,7a,8,8a-hexahydro-2,6-bis(3-trifluoromethylphenylsulfonyloxy)-4,8-ethenobenzo[1,2-c:4,5-c']dipyrrole-1,3,5,7(2H,6H)-tetrone In 1.5 ml of pyridine and 10 ml of N,N-dimethylacetamide, 1.11 g (0.004 mol) of 3a,4,4a,7a,8,8a-hexahydro-2,6-dihydroxy-4,8-ethenobenzo[1,2-c:4,5-c']dipyrrole-1,3,5,7(2H,6H)-tetrone, obtained in Reference Example 2, was dissolved, then 2.94 g (0.012 mol) of 3-trifluoromethylbenzenesulfonyl chloride was added dropwise thereto at room temperature, and the solution was reacted at room temperature for 1 hour with stirring. After completion of the reaction, the obtained reaction solution was poured into 150 ml of water for crystallization, followed by filtering precipitated crude crystal, washing with water and drying to obtain crude crystal. Then, the crude crystal was recrystallized from a mixed solvent of ethyl acetate/methanol to obtain 1.8 g of 3a,4,4a,7a,8,8a-hexahydro-2,6-bis(3-trifluoromethylphenyl-sulfonyloxy)-4,8-ethenobenzo[1,2-c':4,5-c']dipyrrole-1,3,5,7(2H,6H)-tetrone as colorless flaky crystal (yield: 64.8%).

Mp.: 226 ° C.

$^1$HNMR (DMSO-$d_6$) δ ppm: 3.25-3.29(2H, d, CH×2), 3.31-3.36(4H, m, CH×4), 6.17-6.19(2H, t, —CH=×2), 7.98-8.02(2H, t, aromatic ring H×2), 8.23(2H, s, aromatic ring H×2), 8.31-8.33(4H, d, aromatic ring H×4)

IR(KBr-Disk) ν cm$^{-1}$: 3088, 2951, 1750(C=O), 1327 ($SO_2$O), 1200($SO_2$O)

MS(m/z): 694($M^+$)

Examples 7 to 9

Synthesis of the Compounds Shown by the General Formula [11]

The similar procedures as in Example 1 were conducted except that various sulfonyl chlorides were used instead of 3-trifluoromethylbenzenesulfonyl chloride used in Example 6, to obtain desired bisimidesulfonate compounds. The results are shown in Table 2.

TABLE 2

| Example | $R^8$ | Shape (cryst. solvent) Physical property | $^1$H NMR (DMSO-$d_6$) (δ ppm), IR (KBr-Disk) (ν cm$^{-1}$), and others |
|---|---|---|---|
| 7 | p-methyl-phenyl | colorless powder crystal (DMAc/$Me_2$CO) Mp.: ≧300° C. | $^1$HNMR: 2.47 (6 H, s, $CH_3$ × 2), 3.38 (6 H, s, CH × 6), 6.22 (2 H, s, —CH= × 2), 7.53-7.55 (2 H, d, aromatic ring H × 2), 7.85-7.87 (2 H, d, aromatic ring H × 2) IR: 3057, 2934, 1805 (C=O), 1742 (C=O), 1397 ($SO_2$O), 1196 ($SO_2$O) |
| 8 | 3,5-di-trifluoro-methyl-phenyl | colorless short needle-like crystal ($Et_2$O/MeCN) Mp.: 196-198° C. | $^1$HNMR: 3.34 (6 H, s, CH × 6), 6.10 (2 H, s, —CH= × 2), 8.59 (4 H, s, aromatic ring H × 4), 8.78 (2 H, s, aromatic ring H × 2) IR: 3086, 2965, 1809 (C=O), 1752 (C=O), 1417 ($SO_2$O), 1183 ($SO_2$O) MS (m/z): 830 ($M^+$) |
| 9 | 10-camphor | colorless short needle-like crystal (EtOAc) Mp.: 226° C. | $^1$HNMR: 0.82 (6 H, s, $CH_3$ × 2), 1.01 (6 H, s, $CH_3$ × 2), 1.45 (2 H, m, bridged alicyclic H × 2), 1.62 (2 H, m, bridged alicyclic H × 2), 1.95-1.99 (4 H, m, bridged alicyclic H × 4), 2.11-2.15 (4 H, t, bridged alicyclic H × 4), 2.36-2.41 (2 H, m, bridged alicyclic H × 2), 3.46 (6 H, s, CH × 6), 3.71-3.75 (2 H, d, H—C—H × 2), 3.85-3.89 (2 H, d, H—C—H × 2), 6.18 (2 H, s, —CH= × 2) IR: 2966, 1794 (C=O), 1730 (C=O), 1404 ($SO_2$O), 1196 ($SO_2$O) MS(m/z) : 705 ($M^+$—H) |

* DMAc: N,N-dimethylacetamide, $Me_2$CO: acetone, $Et_2$O: ethyl ether, MeCN: acetnitrile, EtOAc: ethyl acetate

Example 10

Synthesis of 2,6-bis(3-trifluoromethylphenylsulfonyloxy)benzo[1,2-c:4,5-c']dipyrrole-1,3,5,7(2H,6H)-tetrone In 1.5 ml of pyridine and 10 ml of N,N-dimethylacetamide, 1.00 g (0.004 mol) of 2,6-dihydroxybenzo[1,2-c:4,5-c']dipyrrole-1,3,5,7(2H,6H)-tetrone, obtained in Reference Example 3, was suspended, then 2.94 g (0.012 mol) of 3-trifluoromethylbenzenesulfonyl chloride was added dropwise thereto at room temperature, and the suspension was reacted at room temperature for 1 hour with stirring. After completion of the reaction, the obtained reaction solution was poured into 150 ml of water, followed by extraction of oily substance precipitated with 20 ml of methylene chloride three times, washing the organic layer with water (50 ml×4) and concentrating under reduced pressure. Then, the crude crystal residue was recrystallized from a mixed solvent of methylene chloride/acetone to obtain 1.7 g of 2,6-bis(3-trifluoromethylphenylsulfonyloxy)benzo[1,2-c:4,5-c']dipyrrole-1,3,5,7-(2H,6H)-tetrone as pale yellow flaky crystal (yield: 64.0%)

Mp.: 226-228° C.

$^1$HNMR (DMSO-$d_6$) δ ppm: 7.96-8.00(2H, t, aromatic ring H×2), 8.32-8.34(2H, d, aromatic ring H×2), 8.37(2H, s, pyromellitic ring H×2), 8.41-8.45(4H, t, aromatic ring H×4)

IR(KBr-Disk) ν cm$^{-1}$: 3100, 3036, 1798(C=O), 1759 (C=O), 1392(SO$_2$O) 1194(SO$_2$O)

MS(m/z): 664(M$^+$)

Examples 11 to 21

Synthesis of the Compounds Shown by the General Formula [12]

The similar procedures as in Example 10 were conducted except that various sulfonyl chlorides were used instead of 3-trifluoromethylbenzenesulfonyl chloride used in Example 10, to obtain desired bisimidesulfonate compounds. The results are shown in Tables 3 to 5.

TABLE 3

| Example | R$^9$ | Shape (cryst. solvent) Physical property | $^1$H NMR (DMSO-$d_6$) (δ ppm), IR (KBr-Disk) (ν cm$^{-1}$), and others |
|---|---|---|---|
| 11 | n-butyl | colorless flaky crystal (MeCN) Mp.: 226-228° C. | $^1$HNMR: 0.91-0.95 (6 H, t, CH$_3$ × 2), 1.43-1.49 (4 H, q, CH$_2$ × 2), 1.91 (4 H, m, CH$_2$ × 2), 3.82-3.85 (4 H, m, CH$_2$ × 2), 8.46 (2 H, s, pyromerillitic ring H × 2) IR: 3110, 3061, 2963, 2876, 1765 (C=O), 1387 (SO$_2$O), 1177 (SO$_2$O) |
| 12 | benzyl | pale yellow prism crystal (DMAc/Me$_2$CO) Mp.: 227° C. | $^1$HNMR: 5.24 (4 H, s, CH$_2$ × 2), 7.46-7. (6 H, t, aromatic ring H × 6), 7.62-7.63 (4 H, d, aromatic ring H × 4), 8.55 (2 H, s, pyromellitic ring H × 2) IR: 2990, 1796 (C=O), 1757 (C=O), 1402 (SO$_2$O), 1179 (SO$_2$O) |
| 13 | phenyl | pale yellow powder crystal (DMAc) Mp.: ≧300° C. | $^1$HNMR: 7.69-7.73 (4 H, t, aromatic ring H × 4), 7.89-7.93 (2 H, t, aromatic ring H × 2), 8.07-9.09 (4 H, d, aromatic ring H × 4), 8.36 (2 H, s, pyromellitic ring H × 2) |

* MeCN: acetonitrile, Me$_2$CO: acetone, DMAc: N,N-dimethylacetamide,

TABLE 4

| Example | R$^9$ | Shape (cryst. solvent) Physical property | $^1$H NMR (DMSO-$d_6$) (δ ppm), IR (KBr-Disk) (ν cm$^{-1}$), and others |
|---|---|---|---|
| 14 | p-methyl-phenyl | colorless powder crystal (DMAc) Mp. 293° C. | $^1$HNMR: 2.47 (6 H, s, CH$_3$ × 2), 7.51-7.54 (4 H, d, aromatic ring H × 4), 7.95-7.97 (4 H, d, aromatic ring H × 4), 8.38 (2 H, s, pyromellitic ring H × 2) IR: 3100, 3040, 2984, 1782 (C=O), 1757 (C=O), 1593, 1377 (SO$_2$O), 1181 (SO$_2$O) |
| 15 | p-methoxy-phenyl | pale yellow powder crystal (DMAc) Mp. 274° C. | $^1$HNMR: 3.90 (6 H s, CH$_3$O × 2), 7.19-7.21 (4 H, d, aromatic ring H × 4), 7.99-8.01 (4 H, d, aromatic ring H × 4), 8.37 (2 H, s, pyromellitic ring H × 2) |
| 16 | p-fluoro-phenyl | pale yellow powder crystal (DMAc) Mp.: ≧300° C. | $^1$HNMR: 7.55-7.60 (4 H, t, aromatic ring H × 4), 8.18-8.22 (4 H, m, aromatic ring H × 4), 8.40 (2 H, s, pyromellitic ring H × 2) |
| 17 | o-tri-fluoro-methyl-phenyl | pale yellow powder crystal (DMAc) Mp. 277-279° C. | $^1$HNMR: 7.89-7.92 (2 H, t, aromatic ring H × 2), 8.08-8.12 (2 H, t, aromatic ring H × 2), 8.21-8.23 2 H, d, aromatic ring H × 2), 8.28-8.30 (2 H, d, aromatic ring H × 2), 8.32 (2 H, s, pyromellitic ring H × 2) |
| 18 | 2,5-di-chloro-phenyl | pale yellow powder crystal (DMAc/MeOH) Mp. 297-299° C. | $^1$HNMR: 7.93-8.00 (4 H, m, aromatic ring H × 4), 8.08-8.09 (2 H, d, aromatic ring H × 2), 8.38 (2 H, s, pyromellitic ring H × 2) |
| 19 | 2-thiophene | pale yellow flaky crystal (DMAc/MeCN) Mp.: 296° C. | $^1$HNMR: 7.36 (2 H, bs, thiophene ring H × 2), 8.15 (2 H, bs, thiophene ring H × 2), 8.41 (4 H, bs, thiophene ring H × 2 and pyromellitic ring H × 2) IR: 3100, 3040, 1796 (C=O), 1744 (C=O), 1379 (SO$_2$O), 1190 (SO$_2$O) |

* DMAc: N,N-dimethylacetamide, MeOH: methanol, MeCN: acetonitrile

TABLE 5

| Example | R$^9$ | Shape (cryst. solvent) Physical property | $^1$H NMR (DMSO-$d_6$) (δ ppm), IR (KBr-Disk) (ν cm$^{-1}$), and others |
|---|---|---|---|
| 20 | 10-camphor | pale yellow powder crystal (Et$_2$O/MeCN) Mp. 187° C. | $^1$HNMR: 0.85 (6 H, s, CH$_3$ × 2), 1.01 (6 H, s, CH$_3$ × 2), 1.48-1.50 (2 H, m, bridged alicyclic H × 2), 1.70 (2 H, m, bridged alicyclic H × 2), 1.97-2.02 (4 H, m, bridged alicyclic H × 4), 2.11-2.13 (2 H, t, bridged alicyclic H × 2), 2.23-2.26 (2 H, m, bridged alicyclic H × 2), 2.38-2.43 (2 H, m, bridged alicyclic H × 2), 3.91-3.95 (2 H, d, H—C—H × 2), 3.99-4.03 (2 H, d, H—C—H × 2), 8.52 (2 H, s, pyromellitic ring H × 2) IR: 2965, 1798 (C=O), 1754 (C=O), 1402 (SO$_2$O), 1186 (SO$_2$O) MS (m/z): 677 (M$^+$) |
| 21 | p-tri-fluoro-methyl-phenyl | pale yellow powder crystal (DMAc) Mp. 288° C. | $^1$HNMR: 8.11-8.13 (4 H, d, aromatic ring H × 4), 8.34-8.36 (4 H, d, aromatic ring H × 4), 8.42 (2 H, s, pyromellitic ring H × 2) IR: 3106, 3058, 1800 (C=O), 1763 (C=O), 1410 (SO$_2$O), 1183 (SO$_2$O) |

* Et$_2$O: diethylether, MeCN: acetonitrile, DMAc: N,N-dimethylacetamide

Example 22

Synthesis of 2,6-bis(pentafluorobenzenesulfonyloxy)benzo[1,2-c:4,5-c']dipyrrole-1,3,5,7(2H,6H)-tetrone In 20 ml of acetone, 1.00 g (0.004 mol) of 2,6-dihydroxybenzo[1,2-c:4,5-c']dipyrrole-1,3,5,7(2H,6H)-tetrone, obtained in Reference Example 3, and 2.67 g (0.01 mol) of pentafluorobenzenesulfonyl chloride were dissolved, then 1.01 g (0.01 mol) of triethylamine was added dropwise thereto at room temperature, and the solution was reacted for 2 hours with stirring. After completion of the reaction, the obtained reaction solution was poured into 150 ml of water, followed by extracting oily substance precipitated with 50 ml of chloroform 4 times, washing of the organic layer with water (50 ml×4) and concentrating under reduced pressure. Then, the crude crystal residue was recrystallized from a mixed solvent of methylene chloride/ethyl acetate to obtain 1.8 g of 2,6-bis(pentafluorobenzenesulfonyloxy)benzo[1,2-c:4,5-c']dipyrrole-1,3,5,7(2H,6H)-tetrone as pale yellow prism crystal (yield: 63.5%)

Mp.: 299° C.

$^1$HNMR (DMSO-$d_6$) δ ppm: 8.44(2H, s, pyromellitic ring H×2)

IR(KBr-Disk) ν cm$^{-1}$: 3108, 3042, 1784(C=O), 1289 (SO$_2$O), 1120 (SO$_2$O)

MS(m/z): 708 (M$^+$)

Example 23

Synthesis of 2,6-bis(3,5-di-trifluoromethylphenysulfonyloxy)benzo[1,2-c:4,5-c']dipyrrole-1,3,5,7(2H,6H)-tetrone The similar reaction as in Example 23 was conducted except that 3,5-di-trifluoromethylphenylsulfonyl chloride was used instead of pentafluorobenzenesulfonyl chloride used in Example 22, and the obtained reaction solution was poured into 150 ml of water for crystallization, followed by filtering crystal precipitated, washing with water and drying to obtain crude crystal. Then, the crude crystal was recrystallized from a mixed solvent of ethyl ether/acetonitrile to obtain 2.0 g of 2,6-bis(3,5-di-trifluoromethylphenylsulfonyloxy)benzo[1,2-c:4,5-c'] dipyrrole-1,3,5,7(2H,6H)-tetrone as pale yellow flaky crystal (yield: 62.5%).

Mp.: 210-212° C.

$^1$HNMR (DMS-$d_6$) δ ppm: 8.31(2H, s, pyromellitic ring H×2), 8.74(6H, s, aromatic ring H×6)

IR(KBr-Disk) ν cm$^{-1}$: 3098, 3042, 1802(C=O), 1757 (C=O), 1284 (SO$_2$O ), 1196 (SO$_2$O )

MS(m/z): 800(M$^+$)

Example 24

Synthesis of 2,6-bis(nonafluorobutanesulfonyloxy) benzo[1,2-c:4,5-c']dipyrrole-1,3,5,7(2H,6H)-tetrone In 1.5 ml of 2,6-lutidine and 10 ml of N,N-dimethylacetamide, 1.00 g (0.004 mol) of 2,6-dihydroxybenzo[1,2-c:4,5-c']dipyrrole-1,3,5,7(2H,6H)-tetrone, obtained in Reference Example 3, was suspended, then 3.62 g (0.012 mol) of nonafluorobutanesulfonyl fluoride was added dropwise thereto at room temperature, and the suspension was reacted for 30 minutes with stirring. After completion of the reaction, the obtained reaction solution was poured into 150 ml of water for crystallization, followed by filtering precipitated crystal, washing with water and drying to obtain crude crystal. Then, the crude crystal residue was recrystallized from acetonitrile to obtain 1.1 g of 2,6-bis(nonafluorobutanesulfonyloxy)benzo[1,2-c:4,5-c']dipyrrole-1,3,5,7(2H, 6H)-tetrone as pale yellow powder crystal (yield: 39.9%)

Mp.: 300° C. or more $^1$HNMR (DMSO-$d_6$) δ ppm: 8.12 (2H, s, pyromellitic ring H×2)

Example 25

Synthesis of 2,6-bis(trifluoromethanesulfonyloxy) benzo[1,2-c:4,5-c']dipyrrole-1,3,5,7(2H,6H)-tetrone In 20 ml of methylene chloride, 1.00 g (0.004 mol) of 2,6-dihydroxybenzo[1,2-c:4,5-c']dipyrrole-1,3,5,7(2H,6H)-tetrone, obtained in Reference Example 3 and 1.20 g (0.008 mol) of trifluoromethanesulfonic acid were suspended, then 10 ml of methylene chloride solution dissolving 1.65 g (0.008 mol) of dicyclohexylcarbodiimide was added dropwise thereto at room temperature, and the suspension was reacted for 8 hours with stirring. After completion of the reaction, the obtained reaction solution was filtered, followed by washing the filtrate with water and concentrating to obtain 2.3 g of crude crystal. Then, the crude crystal was recrystallized from methanol to obtain 0.6 g of 2,6-bis(trifluoromethanesulfonyloxy)benzo[1,2-c:4,5-c']dipyrrole-1,3,5,7(2H,6H)-tetrone as colorless prism crystal (yield: 29.3%).

Mp.: 231-233° C.

$^1$HNMR (DMSO-$d_6$) δ ppm: 8.12(2H, s, pyromellitic ring H×2)

Example 26

Synthesis of 3a,4,4a,7a,8,8a-hexahydro-2,6-bis(pentafluorobenzenesulfonyloxy)-4,8-ethenobenzo[1,2-c:4,5-c']dipyrrole-1,3,5,7(2H,6H)-tetrone In 20 ml of: acetone, 1.11. g (0.004 mol) of 3a,4,4a,7a,8,8a-hexahydro-2,6-dihydroxy-4,8-ethenobenzo[1,2-c:4,5c']dipyrrole-1,3,5,7(2H,6H)-tetrone, obtained in Reference Example 2 and 2.67 g (0.01 mol) of pentafluorobenzenesulfonyl chloride were dissolved, then 1.01 g (0.01 mol) of triethylamine was added dropwise thereto at room temperature, and, the solution was reacted for 2 hours with stirring. After completion of the reaction, the obtained reaction solution was poured into 150 ml of water for crystallization, followed by filtering precipitated crude crystal, washing with water and drying to obtain crude crystal. Then, the crude crystal was recrystallized from a mixed solvent of acetonitrile/methanol to obtain 1.7 g of 3a,4,4a,7a,8,8a-hexahydro-2,6-bis(pentafluorobenzenesulfonyloxy)-4,8-ethenobenzo[1,2-c:4,5-c']dipyrrole-1,3,5,7 (2H,6H)-tetrone as colorless flaky crystal (yield: 57.6%).

Mp.: 300° C. or more $^1$HNMR (DMSO-$d_6$) δ ppm: 3.32-3.36(6H, m, CH×4), 5.95(2H, bs, —CH=×2)

IR(KBr-Disk) νcm$^{-1}$: 2961, 1815(C=O), 1759(C=O), 1313(SO$_2$O), 1109 (SO$_2$O)

MS(m/z): 736(M$^+$−2H)

Example 27

A resist composition consisting of the following ingredients was prepared.

| | |
|---|---|
| poly (p-hydroxystyrene/styrene/tert-butyl acrylate) | 6.0 g |
| [composition ratio: 7/2/1, weight-average molecular weight (Mw) = 10,000, molecular weight distribution (Mw/Mn) = 1.9] | |
| 2,6-bis(3-trifluoromethylphenylsulfonyloxy)benzo[1,2-c:4,5-c']dipyrrole-1,3,5,7(2H,6H)-tetrone | 0.3 g |
| [the compound of Example 10] | |
| dicyclohexylmethylamine | 0.01 g |
| fluorine-containing nonionic surfactant | 0.1 g |
| [commercial product] | |
| propylene glycol monomethyl ether acetate | 60.0 g |

A pattern was formed as follows using the above-described resist composition.

Namely, the resist composition was filtered using a membrane filter with 0.1 µm pore size, followed by spin-coating on a silicon substrate, pre-baking at 130° C. for 90 sec. on a hot plate, to obtain a resist film with thickness of 0.3 µm. Then a pattern was drawn using EB direct, writing equipment (acceleration voltage of 50 KeV), followed by baking at 120° C. for 60 sec. on a hot plate, developing using a 2.38% aqueous solution of tetramethylammonium hydroxide and washing with water, to form a positive resist pattern. The positive resist pattern thus obtained showed resolution of 100 nm L&S (0.1 µm L&S) with sensitivity of 4.0 µC/cm². Pattern profile was nearly rectangular.

Example 28

A pattern was formed similarly as in Example 27 except that exposure was carried out using a KrF excimer laser stepper (NA 0.55) instead of EB direct writing equipment in Example 27. The positive resist pattern thus obtained showed resolution of 0.15 µm L&S with sensitivity of 5 mJ/cm². Pattern profile was nearly rectangular.

Example 29

A resist composition consisting, of the following ingredients was prepared.

| | |
|---|---|
| poly (p-1-ethoxyethoxystyrene/p-hydroxystyrene/p-tert-butoxystyrene) | 6.0 g |
| [composition ratio: 26/64/10, Mw = 10,000, Mw/Mn = 1.02] | |
| 2,6-bis(3-trifluoromethylphenylsulfonyloxy)benzo[1,2-c:4,5-c']dipyrrole-1,3,5,7(2H,6H)-tetrone | 0.3 g |
| [the compound of Example 10] | |
| tris[2-(2-methoxyethoxy)ethyl]amine | 0.01 g |
| fluorine-containing nonionic surfactant | 0.1 g |
| [commercial product] | |
| propylene glycol monomethyl ether acetate | 60.0 g |

The above-described resist composition was filtered using a membrane filter with 0.1 µm pore size, followed by spin-coating on a silicon substrate, pre-baking at 130° C. for 90 sec. on a hot-plate, to obtain a resist film with thickness of 0.3 µm. Then a pattern was drawn using an EB direct writing equipment (acceleration voltage of 50 KeV), followed by baking at 105° C. for 60 sec. on a hot plate, developing using a 2.38% aqueous solution of tetramethylammonium hydroxide and washing with water, to form a positive resist pattern. The positive resist pattern thus obtained showed resolution of 100 nm L&S (0.1 µm L&S) with sensitivity of 2.8 µC/cm². Pattern profile was nearly rectangular.

Example 30

A pattern was formed similarly as in Example 29 except that exposure was carried out using a KrF excimer laser stepper instead of the EB direct writing equipment in Example 29. The positive resist pattern thus obtained showed resolution of 0.15 µm L&S with sensitivity of 3 mJ/cm². Pattern profile was nearly rectangular.

Example 31

A resist composition consisting of the following ingredients was prepared.

| | |
|---|---|
| poly (p-tert-butoxystyrene/p-hydroxystyrene) | 6.0 g |
| [composition ratio: 33/67, Mw = 10,000, Mw/Mn = 1.02] | |
| 2,6-bis(3-trifluoromethylphenylsulfonyloxy)benzo[1,2-c:4,5-c']dipyrrole-1,3,5,7(2H,6H)-tetrone | 0.3 g |
| [the compound of Example 10] | |
| dicyclohexylmethylamine | 0.01 g |
| fluorine-containing nonionic surfactant | 0.1 g |
| [commercial product] | |
| propylene glycol monomethyl ether acetate | 60.0 g |

A pattern was formed similarly as in Example 27 using the above-described resist composition. The positive resist pattern thus obtained showed resolution of 100 nm L&S (0.1 µm L&S) with sensitivity of 3.0 µC/cm². Pattern profile was nearly rectangular.

Example 32

A pattern was formed similarly as in Example 27 except that exposure was carried out using a KrF excimer laser stepper instead of the EB direct writing equipment in Example 31. The positive resist pattern thus obtained showed resolution of 0.15 µm L&S with sensitivity of 3 mJ/cm². Pattern profile was nearly rectangular.

Example 33

A resist composition consisting of the following ingredients was prepared.

| | |
|---|---|
| poly (p-tert-butoxystyrene/p-hydroxystyrene) | 6.0 g |
| [composition ratio: 1/9, Mw = 2,500, Mw/Mn = 1.02] | |
| 2,6-bis(pentafluorobenzenesulfonyloxy)benzo[1,2-c:4,5-c']dipyrrole-1,3,5,7(2H,5H)-tetrone | 0.3 g |
| [the compound of Example 22] | |
| 2,4,6-tris(methoxymethyl)amino-1,3,5-s-triazine | 2.0 g |
| dicyclohexylmethylamine | 0.01 g |
| fluorine-containing nonionic surfactant | 0.1 g |
| [commercial product] | |
| propylene glycol monomethyl ether acetate | 58.0 g |

A pattern was formed similarly as in Example 27 using the above-described resist composition. The negative resist pattern thus obtained showed resolution of 100 nm L&S (0.1 µm L&S) with sensitivity of 7.0 µC/cm². Pattern profile was nearly rectangular.

Example 34

A resist composition consisting of the following ingredients was prepared.

| | |
|---|---|
| poly (p-tert-butoxystyrene/p-hydroxystyrene) [composition ratio: 2/8, Mw = 8,500, Mw/Mn = 1.05] | 6.0 g |
| 2,6-bis(pentafluorobenzenesulfonyloxy)benzo[1,2-c:4,5-c']dipyrrole-1,3,5,7(2H,6H)-tetrone [the compound of Example 22] | 0.3 g |
| 4,4',4''-tris(4-tert-butoxycarbonylmethoxyphenyl)methane | 1.5 g |
| dicyclohexylmethylamine | 0.01 g |
| fluorine-containing nonionic surfactant [commercial product] | 0.1 g |
| propylene glycol monomethyl ether acetate | 58.0 g |

A pattern was formed similarly as in Example 27 using the above-described resist composition. The positive resist pattern thus obtained showed resolution of 100 nm L&S (0.1 μm L&S) with sensitivity of 4.0 μC/cm². Pattern profile was nearly rectangular.

Example 35

A resist composition consisting of the following ingredients was prepared.

| | |
|---|---|
| poly (p-tert-butoxycarbonylmethoxystyrene/styrene/p-hydroxystyrene) [composition ratio: 25/10/65, Mw = 10,000, Mw/Mn = 1.85] | 6.0 g |
| 2,6-bis(nonafluorobutanesulfonyloxy)benzo[1,2-c:4,5-c']dipyrrole-1,3,5,7(2H,6H)-tetrone [the compound of Example 24] | 0.3 g |
| dicyclohexylmethylamine | 0.01 g |
| fluorine-containing nonionic surfactant [commercial product] | 0.1 g |
| ethyl lactate | 30.0 g |
| ethyl 3-ethoxypropionate | 30.0 g |

A pattern was formed similarly as in Example 27 using the above-described resist composition. The positive resist pattern thus obtained showed resolution of 100 nm L&S (0.1 μm L&S) with sensitivity of 4.0 μC/cm². Pattern pprofile was nearly rectangular.

Example 36

A resist composition consisting of the following ingredients was prepared.

| | |
|---|---|
| poly (p-hydroxystyrene/styrene/tert-butyl acrylate) [composition ratio: 7/2/1, Mw = 10,000, Mw/Mn = 1.9] | 6.0 g |
| 2,6-bis(3,5-di-trifluoromethylphenylsulfonyloxy)benzo[1,2-c:4,5-c']dipyrrole-1,3,5,7(2H,6H)-tetrone [the compound of Example 23] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 27 using the above-described resist composition. The positive resist pattern thus obtained showed resolution of 100 nm L&S (0.1 μm L&S) with sensitivity of 4.0 μC/cm². Pattern profile was nearly rectangular.

Example 37

A resist composition consisting of the following ingredients was prepared.

| | |
|---|---|
| poly (p-tert-butoxystyrene/p-hydroxystyrene) [composition ratio: 33/67, Mw = 10,000, Mw/Mn = 1.02] | 6.0 g |
| 2,6-bis(10-camphorsulfonyloxy)benzo[1,2-c:4,5-c']dipyrrole-1,3,5,7(2H,6H)-tetrone [the compound of Example 20] | 0.3 g |
| 4-N,N-dimethylaminopyridine | 0.01 g |
| fluorine-containing nonionic surfactant [commercial product] | 0.1 g |
| propylene glycol monomethyl ether acetate | 60.0 g |

A pattern was formed similarly as in Example 27 using the above-described resist composition. The positive resist pattern thus obtained showed resolution of 100 nm L&S (0.1 μm L&S) with sensitivity of 5.0 μC/cm². Pattern profile was nearly rectangular.

Example 38

A resist composition consisting of the following ingredients was prepared.

| | |
|---|---|
| poly (p-1-ethoxyethoxystyrene/p-hydroxystyrene/p-tert-butoxystyrene) [composition ratio: 26/64/10, Mw = 10,000, Mw/Mn = 1.02] | 6.0 g |
| tetrahydro-2,5-bis(10-camphorsulfonyloxy) cyclobuta[1,2-c:3,4-c']dipyrrole-1,3,4,6(2H,5H)-tetrone [the compound of Example 5] | 0.3 g |
| trioctylamine | 0.01 g |
| fluorine-containing nonionic surfactant [commercial product] | 0.1 g |
| propylene glycol monomethyl ether acetate | 60.0 g |

A pattern was formed similarly as in Example 30 using the above-described resist composition. The positive resist pattern thus obtained showed resolution of 0.15 μm L&S with sensitivity of 4 mJ/cm². Pattern profile was nearly rectangular.

Example 39

A resist composition consisting of the following ingredients was prepared.

| | |
|---|---|
| poly (p-tert-butoxystyrene/p-hydroxystyrene) [composition ratio: 33/67; Mw = 10,000, Mw/Mn = 1.02] | 6.0 g |
| 3a,4,4a,7a,8,8a-hexahydro-2,6-bis(3-trifluoromethylphenylsulfonyloxy)-4,8-ethenobenzo[1,2-c:4,5-c']dipyrrole-1,3,5,7(2H,6H)-tetrone [the compound of Example 6] | 0.3 g |
| dicyclohexylmethylamine | 0.01 g |
| fluorine-containing nonionic surfactant [commercial product] | 0.1 g |
| ethyl lactate | 60.0 g |

A pattern was formed similarly as in Example 27 using the above-described resist composition. The positive resist pattern thus obtained showed resolution of 100 nm L&S (0.1 μm L&S) with sensitivity of 4.0 μC/cm². Pattern profile was nearly rectangular.

Example 40

A resist composition consisting of the following ingredients was prepared.

| | |
|---|---|
| poly (p-tert-butoxystyrene/p-hydroxystyrene) [composition ratio: 33/67, Mw = 10,000, Mw/Mn = 1.02] | 6.0 g |
| 3a,4,4a,7a,8,8a-hexahydro-2,6-bis(10-camphorsulfonyloxy)-4,8-ethenobenzo[1,2-c:4,5-c']dipyrrole-1,3,5,7(2H,6H)-tetrone [the compound of Example 9] | 0.3 g |
| dicyclohexylmethylamine | 0.01 g |
| fluorine-containing nonionic surfactant [commercial product] | 0.1 g |
| propylene glycol monomethyl ether acetate | 30.0 g |
| ethyl 3-ethoxypropionate | 30.0 g |

A pattern was formed similarly as in Example 28 using the above-described resist composition. The positive resist pattern thus obtained showed resolution of 0.15 μm L&S with sensitivity of 5 mJ/cm$^2$. Pattern profile was nearly rectangular.

Example 41

A resist composition consisting of the following ingredients was prepared.

| | |
|---|---|
| poly (p-tert-butoxystyrene/p-hydroxystyrene) [composition ratio: 33/67, Mw = 10,000, Mw/Mn = 1.02] | 6.0 g |
| 3a,4,4a,7a,8,8a-hexahydro-2,6-bis(pentafluorobenzenesulfonyloxy)-4,8-ethenobenzo[1,2-c:4,5-c']dipyrrole-1,3,5,7(2H,6H)-tetrone [the compound of Example 26] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 27 using the above-described resist composition. A positive resist pattern thus obtained showed resolution of 100 nm L&S (0.1 μm L&S) with sensitivity of 4.0 μC/cm$^2$. Pattern profile was nearly rectangular.

Comparative Example 1

A resist composition consisting of the following ingredients was prepared.

| | |
|---|---|
| poly (p-hydroxystyrene/styrene/tert-butyl acrylate) [composition ratio: 7/2/1, Mw = 10,000, Mw/Mn = 1.9] | 6.0 g |
| 2,6-bis(methanesulfonyloxy)benzo[1,2-c:4,5-c']dipyrrole-1,3,5,7(2H,6H)-tetrone [the compound of Reference Example 6] | 0.3 g |
| dicyclohexylmethylamine | 0.01 g |
| fluorine-containing nonionic surfactant [commercial product] | 0.1 g |
| propylene glycol monomethyl ether acetate | 60.0 g |

Preparation of the above-described composition was conducted, but could not be succeeded due to no dissolution of the acid generator.

Comparative Example 2

A resist composition consisting of the following ingredients was prepared.

| | |
|---|---|
| poly (p-tert-butoxystyrene/p-hydroxystyrene) [composition ratio: 33/67, Mw = 10,000, Mw/Mn = 1.02] | 6.0 g |
| N-10-camphorsulfonyloxy-5-norbornene-2,3-dicarboxyimide [the compound of Reference Example 4] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 28 using the above-described resist composition. The positive resist pattern thus obtained showed resolution of 0.18 μm L&S with sensitivity of 10 mJ/cm$^2$, but 0.18 μm L&S could not be resolved. The pattern was poor with tapered profile.

Comparative Example 3

A resist composition consisting of the following ingredients was prepared.

| | |
|---|---|
| poly (p-tert-butoxystyrene/p-hydroxystyrene) [composition ratio: 33/67, Mw = 10,000, Mw/Mn = 1.02] | 6.0 g |
| N-pentafluorobenzenesulfonyloxy-5-norbornene-2,3-dicarboxyimide [the compound of Reference Example 5] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 27 using the above-described resist composition. The positive resist pattern thus obtained showed resolution of 110 nm L&S (0.1 μm L&S) with sensitivity of 8.0 μC/cm$^2$, but 100 nm L&S could not be resolved. The pattern was poor with reversely tapered profile.

Comparative Example 4

A resist composition consisting of the following ingredients was prepared.

| | |
|---|---|
| poly (p-tert-butoxycarbonylmethoxystyrene/styrene/p-hydroxystyrene) [composition ratio: 25/10/65, Mw = 10,000, Mw/Mn = 1.85] | 6.0 g |
| 3a,4,4a,7a,8,8a-hexahydro-2,6-bis(n-butanesulfonyloxy)-4,8-ethenobenzo[1,2-c:4,5-c']dipyrrole-1,3,5,7(2H,6H)-tetrone [the compound of Reference Example 7] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 27 using the above-described resist composition. The positive resist pattern thus obtained showed resolution of 120 nm L&S (0.12 μm L&S) with sensitivity of 10 μC/cm$^2$, but 100 nm L&S could not be resolved. The pattern was poor with tapered profile.

Comparative Example 5

A resist composition consisting of the following ingredients was prepared.

| | |
|---|---|
| poly (p-hydroxystyrene/styrene/tert-butyl acrylate) [composition ratio: 7/2/1, Mw = 10,000, Mw/Mn = 1.9] | 6.0 g |
| N-10-camphorsulfonyloxy-5-norbornene-2,3-dicarboxyimide [the compound of Reference Example 5] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 27 using the above-described resist composition. The positive resist pattern thus obtained showed resolution of 120 nm L&S (0.12 μm L&S) with sensitivity of 12 mJ/cm$^2$, but 100 nm L&S could not be resolved. The pattern was poor with tapered profile.

As is clear from the results of each Example, the bisimidesulfonate compound shown by the general formula [4], among the compounds of the present invention, was found to be very useful as an acid generator for a chemically amplified resist composition. While, a conventional compound very similar to the compound shown by the general formula [4] was found not to provide a resist composition due to poor solubility as is clear from the results of Comparative Example 1, or was difficult to be used due to low sensitivity, low resolution and poor profile as is clear from the comparison of the results of Comparative Example 4 and Example 35.

Furthermore, a conventional compound similar to the compound shown by the general formula [4] was confirmed to show low sensitivity, low resolution and poor profile by the comparisons among Examples 27 to 32, Examples 35 to 41 and Comparative Examples 2, 3 and 5.

Example 42

Synthesis of 5,5'-oxybis[2-hydroxyl-1H-isoindole-1, 3(2H)-dione]

In 150 ml of a pyridine solution dissolving 11.9 g (0.17 mol) of hydroxylamine hydrochloride, 24.1 g (0.078 mol) of 4,4'-oxydiphthalic anhydride was added at room temperature, and the solution was reacted at 90° C. for 15 minutes with stirring. After completion of the reaction, the obtained reaction solution was concentrated under reduced pressure, and the resulting residue was added with 150 ml of an aqueous solution of 6% of acetic acid, followed by filtering precipitated crystal, washing with water and recrystallization from ethanol, to obtain 24.6 g of desired substance as pale yellow powder crystal.

Mp.: 286-287° C.
$^1$HNMR (DMSO-d$_6$) δ ppm: 7.49-7.51(4H, m, phthalimide ring H×4), 7.88-7.90(2H, d, phthalimide ring H×2), 10.85(2H, s, OH×2)
IR (KBr-Disk) ν cm$^{-1}$: 3175, 1786(C=O), 1716(C=O)

Example 43

Synthesis of 5,5'-[2,2,2-trifluoro-1-(trifluoromethyl) ethylidene]bis[2-hydroxyl-1H-isoindole-1,3(2H)-dione]

The similar reaction and treatment as in Example 42 were carried out using 20.0 g (0.045 mol) of 4,4'-(hexafluoroisopropylidene)diphthalic anhydride and 6.9 g (0.099 mol) of hydroxylamine hydrochloride salt. The obtained precipitated oily substance was fractionated and recrystallized from ethyl acetate. The obtained precipitated crystal was filtered, followed by washing with water and drying under reduced pressure, to obtain 19.8 g of desired substance as orange yellow powder crystal.

Mp.: 102-110° C.
$^1$HNMR (DMSO-d$_6$) δ ppm: 7.62(2H, s, phthalimide ring H×2), 7.82-7.84(2H, d, phthalimide ring H×2), 7.97-7.99 (2H, d, phthalimide ring H×2), 11.01(2H, s, OH×2)
IR (KBr-Disk) ν cm$^{-1}$: 3275, 1792(C=O), 17,17(C=O)

Example 44

Synthesis of 5,5'-bis[2-hydroxyl-1H-isoindole-1,3 (2H)-dione]

The similar reaction and treatment as in Example 42 were carried out using 25.0 g (0.085 mol) of 4,4'-biphthalic anhydride and 13.0 g (0.187 mol) of hydroxylamine hydrochloride, to obtain 27.4 g of desired substance as yellow powder crystal.

Mp.: 300° C. or more
$^1$HNMR (DMSO-d$_6$) δ ppnm: 7.93-7.95(2H, d, phthalimide ring H×2), 8.23(2H, s, phthalimidd ring H×2), 8.23-8.26 (2H, d, phthalimide ring H×2), 10.89(2H, s, OH×2)
IR (KBr-Disk) ν cm$^{-1}$: 3212, 1782(C=O), 1725(C=O)

Example 45

Synthesis of 5,5'-oxybis[2-(3-trifluoromethylphenylsulfonyl)oxy-1H-isoindole-1,3(2H)-dione]

In 1.5 ml of pyridine and 10 ml of N,N-dimethylacetamide, 1.36 g (0.004 mol) of 5,5'-oxybis[2-hydroxyl-1H-isoindole-1,3 (2H)-dione], obtained in Example 42, was dissolved, and then 2.94 g (0.012 mol) of 3-trifluoromethylbenzenesulfonyl chloride was added dropwise thereto at room temperature, and the solution was reacted at room temperature for 3 hours with stirring. After completion of the reaction, the obtained reaction solution was poured into 150 ml of water for crystallization, followed by filtering precipitated crude crystal, washing with water then with methanol, and recrystallizing from acetonitrile, to obtain 1.9 g of desired substance as pale yellow flaky crystal.

Mp.: 189-192° C.
$^1$HNMR (DMSO-d$_6$) δ ppm: 7.60-7.62(4H, m, phthalimide ring H×4), 7.98-8.01(4H, dd, phthalimide ring H×2 and aromatic ring H×2), 8.31-8.33(2H, d, aromatic ring H×2), 8.37(2H, s, aromatic ring H×2), 8.40-8.42(2H, d, aromatic ring H×2)
IR (KBr-Disk) 1) ν cm$^{-1}$: 3112, 1793(C=O), 1761 (C=O), 1329(SO$_2$) 1194(SO$_2$)

Example 46

Synthesis of 5,5'-[2,2,2-trifluoro-1-(trifluoromethyl) ethylidene]bis[2-(3-trifluoromethylphenylsulfonyl) oxy-1H-isoindole-1,3(2H)-dione]

The similar reaction and post-treatment as in Example 45 were carried out using 1.90 g (0.004 mol) of 5,5'-[2,2,2-trifluoro-1-(trifluoromethyl)ethylidene]bis[2-hydroxyl-1H-isoindole-1,3(2H)-dione], obtained in Example 43, and 2.94 g (0.012 mol) of 3-trifluoromethylbenzenesulfonyl chloride.

The obtained crude crystal was recrystallized from n-hexane/ethyl ether to obtain 2.54 g of desired substance as pale yellow flaky crystal.

$^1$HNMR (DMSO-d$_6$) δ ppm: 7.66(2H, s, aromatic ring H×2), 7.91-7.93 (2H, d, aromatic ring H×2), 7.96-8.00(2H, t, aromatic ring H×2), 8.08-8.10(2H, d, aromatic ring H×2), 8.31-8.32(2H, d, aromatic ring H×2), 8.40(2H, s, aromatic ring H×2), 8.42-8.45(2H, d, aromatic ring H×2)

Example 47

Synthesis of 5,5'-bis[2-(3-trifluoromethylphenylsulfonyl)oxy-1H-isoindole-1,3(2H)-dione]

The similar reaction and post-treatment as in Example 45 were carried out using 0.68 g (0.002 mol) of 5,5'-bis[2-hydroxyl-1H-isoindole-1,3 (2H)-dione], obtained in Example 44, and 1.55 g (0.006 mol) of 3-trifluoromethyl-benzenesulfonyl chloride. The obtained crude crystal was recrystallized from acetonitrile to obtain 0.5 g of desired substance as pale yellow powder crystal.

Mp.: 235-236° C.

$^1$HNMR (DMSO-d$_6$) δ ppm: 7.97-8.04(4H, m, phthalimide ring H×2 and aromatic ring H×2), 8.32-8.45(10H,m, phthalimide ring H×4 and aromatic ring H×6)

IR (KBr-Disk) ν cm$^{-1}$: 3092, 1792(C=O), 1755(C=O), 1329(SO$_2$), 1198 (SO$_2$).

Example 48

Synthesis of 5,5'-[2,2,2-trifluoro-1-(trifluoromethyl) ethylidene]bis[2-(4-toluenesulfonyl)oxy-1H-isoindole-1,3(2H)-dione]

The similar reaction and post-treatment as in Example 45 were carried out using 1.90 g (0.004 mol) of 5,5'-[2,2,2-trifluoro-1-(trifluoromethyl)ethylidene]bis[2-hydroxyl-1H-isoindole-1,3(2H)-dione], obtained in Example 43, and 2.29 g (0.012 mol) of p-toluenesulfonyl chloride. The obtained crude crystal was recrystallized from methanol to obtain 1.25 g of desired substance as pale yellow powder crystal.

Mp.: 122-131° C.

$^1$HNMR (DMSO-d$_6$) δ ppm: 2.50(6H, s, CH$_3$×2), 7.52-7.54 (4H, d, aromatic ring H×4), 7.70(2H, s, phthalimide ring H×2), 7.93-7.95(2H, d, phthalimide ring H×2), 7.97 (4H, d, aromatic ring H×4), 8.07-8.10(2H, d, phthalimide ring H×2)

IR (KBr-Disk) ν cm$^{-1}$: 3073, 1806(C=O), 1759(C=O), 1400(SO$_2$), 1196(SO$_2$)

Example 49

Synthesis of 5,5'-oxybis[2-(camphorsulfonyl)oxy-1H-isoindole-1,3(2H)-dione]

In 1.5 ml of pyridine and 10 ml of N,N-dimethylacetamide, 1.36 g (0.004 mol) of 5,5'-oxybis[2-hydroxyl-1H-isoindole-1,3 (2H)-dione], obtained in Example 42, was dissolved, then 3.01 g (0.012 mol) of 10-camphorsulfonyl chloride was added dropwise thereto at room temperature, and the solution was reacted at room temperature for 1 hour with stirring. After completion of the reaction, the obtained reaction solution was poured into 150 ml of water for crystallization, followed by extracting white oily substance with methylene chloride (50 ml×3), washing the organic layer with water(100 ml×3) and concentrating under reduced pressure, to obtain 2.3 g of pale yellow viscous oily substance. Then, the obtained oily substance was separated by a column chromatography ["Wakogel C-200", eluent: methylene chloride/methanol=16/1 (v/v)], followed by recrystallization from n-hexane/ethyl acetate, to obtain 1.2 g of desired substance as colorless short needle-like crystal.

Mp.: 169-174 ° C.

$^1$HNMR (DMSO-d$_6$) δ ppm: 0.83(6H, s, CH$_3$×2), 1.04 (6H, s, CH$_3$×2), 1.46-1.48(2H, m, bridged aliphatic ring H×2), 1.68(2H, m, bridged aliphatic ring H×2), 1.95-2.00 (4H, m, bridged aliphatic ring H×4), 2.11(2H, t, bridged aliphatic ring H×2), 2.21-2.24(2H, m, bridged aliphatic ring H×2), 2.36-2.40(2H, m, bridged aliphatic ring H×2)3.87-3.98(4H, q, CH$_2$×2), 7.65-7.66(2H, d, phthalimide ring H×2), 7.70(2H, s, phthalimide ring H×2), 8.08-8.10(2H, d, phthalimide ring H×2)

IR (KBr-Disk) ν cm$^{-1}$: 3102, 2969, 1798 (C=O), 17.50 (C=O), 1399 (SO$_2$), 11.86(502) (SO$_2$)

UV (MeCN) λmax: 318 nm (ε 5760)

Example 50

Synthesis of 5,5'-[2,2,2-trifluoro-1-(trifluoromethyl) ethylidene]bis[2-(10-camphorsulfonyl)oxy-1H-isoindolel-1,3(2H)-dione]

The similar reaction as in Example 49 was carried out using 1.90 g (0.004. mol) of 5,5'-[2,2,2-trifluoro-1-(trifluoromethyl)ethylidene]-bis[2-hydroxyl-1H-isoindole-1,3 (2H)-dione], obtained in Example 43, and 3.01 g (0.012 mol) of 10-camphorsulfonyl chloride. The obtained reaction solution was poured into 150 ml of water for crystallization, followed by filtering the obtained crystal, washing with water and drying, to obtain 3.8 g of crude crystal. Then, the crude crystal was recrystallized from methanol to obtain 0.5 g of desired substance as colorless prism crystal.

Mp.: 140-145° C.

$^1$HNMR (DMSO-d$_6$) δ ppm: 0.83(6H, s, CH$_3$×2), 1.04 (6H, s, CH$_3$×2), 1.46-1.48(2H, m, bridged aliphatic ring H×2), 1.67(2H, m, bridged aliphatic ring H×2), 1.95-2.00 (4H, m, bridged aliphatic ring H×4), 2.11(2H, t, bridged aliphatic ring H×2), 2.22-2.25(2H, m, bridged aliphatic ring H×2), 2.36,-2.41(2H, m, bridged aliphatic ring H×2), 3.87-3.98(4H, q; CH$_2$×2), 7.-74(2H, s, phthalimide ring H×2), 7.98-8.00(2H, d, phthalimide ring H×2), 8.18-8.20(2H, d, phthalimide ring H×2)

IR (KBr-Disk) ν cm$^{-1}$: 3113, 2969, 1802 (C=O), 1757 (C=O), 1391 (SO$_2$), 1188(SO$_2$)

Example 51

Synthesis of 5,5'-oxybis[2-(pentafluorobenzenesulfonyl)oxy-1H-isoindole-1,3(2H)-dione]

In 25 ml of acetone, 1.36 g (0.004 mol) of 5,5'-oxybis[2-hydroxyl-1H-isoindole-1,3(2H)-dione], obtained in Example 42, and 2.67 g (0.01 mol) of pentafluorobenzenesulfonyl chloride were suspended, then 1:01 g (0.01 mol) of triethylamine was added dropwise thereto at 18 to 25° C., and the suspension was reacted at room temperature for 2 hours with stirring. The reaction solution was poured into 150 ml of water, followed by extracting the precipitated viscous oily substance with methylene chloride (50 ml×3), washing the organic layer with water (100 ml×3) and concentrating under reduced pressure, to obtain 2.5 g of pale yellow crude crystal. Then, the crude crystal was recrystallized from methylene chloride/acetonitrile, to obtain 0.8 g of desired substance as pale yellow powder crystal.

Mp.: 224-229° C.

$^1$HNMR (DMSO-d$_6$) δ ppm: 7.61-7.64(4H, m, phthalimide ring H×4), 8.02-8.04(2H, d, phthalimide ring H×2)

IR (KBr-Disk) ν cm$^{-1}$: 3108, 1848(C=O), 1765(C=O), 1429(SO$_2$), 1203 (SO$_2$)

UV (MeCN) λmax: 313 nm (ε7800), 275 nm (ε 11910)

MS(m/z): 800 [M–H]

Example 52

Synthesis of 5,5'-bis[2-n-butanesulfonyloxy-1H-isoindole-1,3(2H)-dione]

The similar reaction and post-treatment as in Example 45 were carried out using 1.30 g (0.04 mol) of 5,5'-bis[2-hydroxyl-1H-isoindole-1,3 (2H)-dione], obtained in Example 44, and 1.88 g (0.012 mol) of n-butanesulfonyl chloride. The obtained pale yellow crude crystal was recrystallized from acetone/methanol to obtain 1.5 g of desired substance as colorless flaky crystal.

Mp.: 213-214° C.

$^1$HNMR (DMSO-d$_6$) δ ppm: 0.92-0.95(6H, t, CH$_3$×2), 1.43-1.49(4H, q, CH$_2$×2), 1.90-1.94(4H, m, CH$_2$×2), 3.79-3.83(4H, m, CH$_2$×2), 8.09-8.11(2H, d, phthalimide ring H×2), 8.39-8.41(2H, d, phthalimide ring H×2), 8.46(2H, s, phthalimide ring hydrogen×2)

IR (KBr-Disk) ν cm$^{-1}$: 2969, 1790(C=O), 1744(C=O), 1387(SO$_2$), 1173 (SO$_2$)

Example 53

Synthesis of 5,5'-oxybis[2-(3,5-di-trifluoromethyl-sulfonyl)oxy-1H-isoindole-1,3(2H)-dione]

The similar reaction and post-treatment as in Example 45 were carried out using 1.36 g (0.004 mol) of 5,5'-oxybis[2-hydroxyl-1H-isoindole-1,3(2H)-dione], obtained in Example 42, and 3.13 g (0.01 mol) of 3,5-di-trifluoromethylphenylsulfonyl chloride, to obtain 3.1 g of pale yellow crude crystal. Then, by recrystallizing the crude crystal wasfrecrystallized from isopropyl ether/acetonitrile, to obtain 1.5 g of desired substance as colorless prism crystal.

Mp.: 179-183° C.

$^1$HNMR (DMSO-d$_6$) δ ppm: 7.56-7.61(4H, m, phthalimide ring H×4), 7.99-8.01(2H, d, phthalimide ring H×2), 8.73(4H, s, aromatic ring H×4), 8.75(2H, s, aromatic ring H×2)

IR (KBr-Disk) ν cm$^{-1}$: 3092, 1796(C=O), 1746(C=O), 1410 (SO$_2$), 1202(SO$_2$)

Example 54

Synthesis of 5,5'-[2,2,2-trifluoro-1-(trifluoromethyl)ethylidene]bis[2-(pentafluorobenzenesulfonyl)oxy-1H-isoindole-1,3(2H)-dione]

The similar reaction and post-treatment as in Example 46 were carried out using 1.90 g (0.004 mol) of 5,5'-[2,2,2-trifluoro-1-(trifluoromethyl)ethylidene]bis[2-hydroxyl-1H-isoindole-1,3(2H)-dione], obtained in Example 43, and 2.67 g (0.01 mol) of pentafluorobenzenesulfonyl chloride, to obtain 3.6 g of pale yellow crude crystal. Then, the crude crystal was recrystallized from methylene chloride/acetonitrile, to obtain 2.0 g of desired substance as pale yellow prism crystal.

Mp.: 227-230° C.

$^1$HNMR (DMSO-d$_6$) δ ppm: 7.67(2H, s, phthalimide ring H×2), 7.91-7.93(2H, d, phthalimide ring H×2), 8.11-8.13 (2H, d, phthalimide ring H×2)

IR (KBr-Disk) ν cm$^{-1}$: 3108, 1811(C=O), 1765(C=O), 1426(SO$_2$) 1200(SO$_2$)

MS (mz): 933 [M–H]

Example 55

Synthesis of 5,5'-bis[2-(4-toluenesulfonyl)oxy-1H-isoindole-1,3(2H)-dione]

The similar reaction and post-treatment as in Example 45 were carried out using 1.30 g (0.04 mol) of 5,5'-bis[2-hydroxyl-1H-isoindole-1,3(2H)-dione], obtained in Example 44, and 2.29 g (0.012 mol) of p-toluenesulfonyl chloride, to obtain 4.1 g of pale yellow crude crystal. Then, the crude crystal was recrystallized from acetonitrile, to obtain 1.4 g of 5,5'-bis[2-(4-toluenesulfonyl)oxy-1H-isoindole-1,3(2H)-dione] as pale yellow short needle-like crystal.

Mp.: 287-288° C.

$^1$HNMR (DMSO-d$_6$) δ ppm: 2.50(6H, s, CH$_3$×2), 7.53-7.55(4H, d, aromatic ring H×4), 7.95-7.97(4H, d, aromatic ring H×4), 8.02-8.04(2H, d, phthalimide ring, H×2); 8.34-8.36(2H, d, phthalimide ring H×2), 8.39(2H, phthalimide ring H×2)

IR (KBr-Disk) ν cm$^{-1}$: 3069, 1790(C=O), 1755(C=O), 1395(SO$_2$), 1196(SO$_2$)

Examples 56 to 65

Synthesis of the Compounds Shown by the General Formula [13]

The similar reactions and post-treatments as in Example 51 were conducted except that various sulfonyl chlorides were used instead of pentafluorobenzenesulfonyl chloride used in Example 51, to obtain desired bisimidesulfonate compounds after purifying the obtained crude crystals. The results are shown in Tables 6 to 9.

TABLE 6

| Example | R$^1$ | Shape (cryst. solvent) Physical property | $^1$H NMR, IR, and others |
|---|---|---|---|
| 56 | phenyl | pale yellow flaky crystal (MeCN) Mp.: 255-256° C. | $^1$HNMR (DMSO-d$_6$) δ ppm: 7.60-7.61 (4H, m, phthalimide ring H × 4), 7.70-7.74 (4H, m, aromatic ring H × 4), 7.89-7.93 (2H, t, aromatic ring H × 2), 7.98-8.00 (2H, d, phthalimide ring H × 2), 8.06-8.08 (4H, d, aromatic ring H × 4) IR (KBr-Disk) ν cm$^{-1}$: 3081, 1792 (C=O), 1755 (C=O), 1787 (SO$_2$), 1194 (SO$_2$) |
| 57 | 4-methoxyphenyl | pale yellow prism crystal (MeCN) Mp.: 227-229° C. | $^1$HNMR (DMSO-d$_6$) δ ppm: 3.09 (6H, s, CH$_3$O × 2), 7.20-7.22 (4H, d, aromatic ring H × 4), 7.60-7.61 (4H, d, phthalimide ring H × 4), 7.97-8.00 (6H, dd, aromatic ring H × 4 and phthalimide ring H × 2) IR (KBr-Disk) ν cm$^{-1}$: 3106, 2951, 1790 (C=O), 1752 (C=O), 1385 (SO$_2$), 1173 (SO$_2$) |

*MeCN: acetonitrile

TABLE 7

| Example | R¹⁰ | Shape (cryst. solvent) Physical property | ¹H NMR, IR, and others |
|---|---|---|---|
| 58 | 4-n-butyl phenyl | orange yellow prism crystal (MeCN) Mp.: 184-185° C. | ¹HNMR (DMSO-d₆) δ ppm: 0.88-0.92 (6H, t, CH₃ × 2), 1.28-1.31 (4H, m, CH₂ × 2), 1.57-1.61 (4H, m, CH₂ × 2), 2.72-2.75 (4H, m, CH₂ × 2), 7.53-7.55 (4H, d, aromatic ring H × 4), 7.60-7.62 (4H, m, phthalimide ring H × 4), 7.95-8.00 (6H, dd, aromatic ring H × 4 and phthalimide ring H × 2) IR (KBr-Disk) ν cm⁻¹: 3077, 2955, 2867, 1792 (C=O), 1750 (C=O), 1387 (SO₂), 1196 (SO₂) UV (THF) λmax: 312 nm (ε 6800) |
| 59 | benzyl | colorless prism crystal (MeCN/ Me₂CO) Mp.: 217° C. | ¹HNMR(DMSO-d₆) δ ppm: 5.18 (4H, s, CH₂ × 2), 7.44-7.46 (6H, m, aromatic ring H × 6), 7.60-6.61 (4H, m, aromatic ring H × 4), 7.71-7.73 (4H, m, phthalimide ring H × 4), 8.06-8.08 (2H, d, phthalimide ring H × 2) IR (KBr-Disk) ν cm⁻¹: 3071, 2996, 1795 (C=O), 1748 (C=O), 1387 (SO₂), 1181 (SO₂) |
| 60 | 4-trifluoromethyl phenyl | pale yellow short needle-like crystal (EtOH/ Me₂CO) Mp.: 184-186° C. | ¹HNMR (DMSO-d₆) δ ppm: 7.60-7.62 (4H, m, phthalimide ring H × 4), 8.00-8.03 (2H, d. phthalimide ring H × 2), 8.10-8.12 (4H, d, aromatic ring H × 4), 8.31-8.33 (4H, d, aromatic ring H × 4) IR (KBr-Disk) ν cm⁻¹: 3106, 1794 (C=O), 1755 (C=O), 1325 (SO₂), 1198 (SO₂) |

*MeCN: acetonitrile, Me₂CO: dimethylketone, EtOH: ethanol

TABLE 8

| Example | R¹⁰ | Shape (cryst. solvent) Physical property | ¹H NMR, IR, and others |
|---|---|---|---|
| 61 | 2,5-dichloro phenyl | colorless powder crystal (DMAc/ MeCN) Mp.: 287° C. | ¹HNMR (DMSO-d₆) δ ppm: 7.59-7.60 (4H, m, phthalimide ring H × 4), 7.92-8.00 (6H, m, phthalimide ring H × 2 and aromatic ring H × 4), 8.08-8.09 (2H, m, aromatic ring H × 2) IR (KBr-Disk) ν cm⁻¹: 3096, 1800 (C=O), 1755 (C=O), 1410 (SO₂), 1196 (SO₂) |
| 62 | 2-thienyl | pale yellow powder crystal (MeCN) Mp.: 255-256° C. | ¹HNMR (DMSO-d₆) δ ppm: 7.34-7.36 (2H, t, thiophene ring H × 2), 7.61-7.63 (4H, m, phthalimide ring H × 4), 8.00-8.02 (2H, d, phthalimide ring H × 2), 8.11-8.12 (2H, d, thiophene ring H × 2), 8.37-8.38 (2H, d, thiophene ring H × 2) IR (KBr-Disk) ν cm⁻¹: 3102, 1794 (C=O), 1750 (C=O), 1393 (SO₂), 1190 (SO₂) |
| 63 | 4-ethyl phenyl | pale yellow short needle-like crystal (MeCN) Mp.: 211-213° C. | ¹HNMR (DMSO-d₆) δ ppm: 1.20-1.24 (6H, t, CH₃ × 2), 2.75-2.77 (4H, m, CH₂ × 2), 7.55-7.57 (4H, d, aromatic ring H × 4), 7.60-7.62 (4H, m, phthalimide ring H × 4), 7.96-8.01 (6H, dd, aromatic ring H × 4 and phthalimide ring H × 2) IR (KBr-Disk) ν cm⁻¹: 3075, 2973, 2876, 1792 (C=O), 1750 (C=O), 1385 (SO₂), 1198 (SO₂) |

*DMAc: N,N-dimethylacetamide, MeCN: acetonitrile

TABLE 9

| Example | R¹⁰ | Shape (cryst. solvent) Physical property | ¹H NMR, IR, and others |
|---|---|---|---|
| 64 | 4-n-propyl phenyl | pale orange yellow short needle-like crystal (MeCN) Mp. 195-197° C. | ¹HNMR (DMSO-d₆) δ ppm: 0.87-0.91 (6H, t, CH₃ × 2), 1.61-1.66 (4H, m, CH₂ × 2), 2.69-2.73 (4H, m, CH₂ × 2), 7.53-7.55 (4H, d, aromatic ring H × 4), 7.60-7.61 (4H, m, phthalimide ring H × 4), 7.98-8.00 (6H, dd, aromatic ring H × 4 and phthalimide ring H × 2) IR (KBr-Disk) ν cm⁻¹: 3079, 2963, 2874, 1792 (C=O), 1761 (C=O), 1389 (SO₂), 1198 (SO₂) |
| 65 | 4-tert-butyl phenyl | pale yellow prism crystal (MeCN/ MeOH) Mp. 170-173° C. | ¹HNMR (DMSO-d₆) δ ppm: 1.33 (18H, s, CH₃ × 6), 7.61-7.63 (4H, m, phthalimide ring H × 4), 7.74-7.76 (4H, d, aromatic ring H × 4), 7.97-8.02 (6H, dd, aromatic ring H × 4 and phthalimide ring H × 2) IR (KBr-Disk) ν cm⁻¹: 3102, 1794 (C=O), 1750 (C=O), 1393 (SO₂), 1190 (SO₂) |

*MeCN: acetonitrile, MeOH: methanol

Examples 66

Synthesis of 5,5'-oxybis[2-nonafluorobutanesulfonyloxy-1H-isoindole-1,3(2H)-dione]

In 2 ml of pyridine and 10 ml of N,N-dimethylacetamide, 1.50 g (0.0044 mol) of 5,5'-oxybis[2-hydroxyl-1H-isoindole-1,3 (2H)-dione], obtained in Example 42, was suspended, then 3.63 g (0.012 mol) of nonafluorobutanesulfonyl fluoride was added dropwise thereto at 0 to 5° C., and the suspension was reacted at the same temperature for 1 hour and then at room temperature for 3 hours with stirring. After the completion of the reaction, the reaction solution was poured into 150 ml of water, followed by filtering precipitated crystal, washing with 50 ml of water 2 times, then 50 ml of methanol one time and drying under reduced pressure, to obtain 2.9 g of pale yellow crude crystal. Then, the obtained crude crystal was recrystallized from N,N-dimethylacetamide/acetonitrile to obtain 1.5 g of 5,5'-oxybis[2-nonafluorobutanesulfonyloxy-1H-isoindole-1,3 (2H)-dione] as pale yellow powder crystal.

¹HNMR (DMSO-d₆) δ ppm: 7.53-7.57(4H, m, phthalimide ring H×4), 7.95-7.97(2H, d, phthalimide ring H×2)

IR (KBr-Disk) ν cm⁻¹: 3088, 1808 (C=O), 1754 (C=O), 1348(SO₂) 1213(SO₂)

Reference Example 8

Synthesis of 5,5'-oxybis[2-(4-toluenesulfonyl)oxy-1H-isoindole-1,3(2H)-dione]

The similar reaction and post-treatment as in Example 45 were carried out using 1.36 g (0.004 mol) of 5,5'-oxybis[2-hydroxyl-1H-isoindole-1,3 (2H)-dione], obtained in Example 42, and 2.29 g (0.012 mol) of p-toluenesulfonyl chloride. The obtained crude crystal was recrystallized from acetonitrile, to obtain 0.8 g of desired substance as colorless needle-like crystal.

Mp.: 250-251° C.

¹HNMR (DMSO-d₆) δ ppm: 2.50(6H, s, CH₃×2), 7.52-7.54(4H, d, aromatic ring H×4), 7.60-7.62(4H, m, phthalimide ring H×4), 7.93-7.95(4H, d, aromatic ring H×4),7.98-8.00(2H, d, phthalimide ring H×2)

IR (KBr-Disk) ν cm$^{-1}$: 3077, 1790(C=O), 1750(C=O), 1385(SO$_2$) 1196(SO$_2$)

Reference Example 9

Synthesis of 5,5'-oxybis[2-trifluoromethanesulfonyloxy-1H-isoindole-1,3(2H)-dione]

The similar reaction and post-treatment as in Example 51 were carried out using 1.36 g (0.004 mol) of 5,5'-oxybis[2-hydroxyl-1H-isoindole-1,3 (2H)-dione], obtained in Example 42, and 1.69 g (0.01 mol) of trifluoromethanesulfonyl chloride. The obtained crude crystal was recrystallized from a mixed solvent of acetonitrile/ethyl ether, to obtain 0.3 g of desired substance as pale yellow powder crystal.

Mp.: 300° C. or more $^1$HNMR (DMSO-d$_6$) δ ppm: 7.46-7.47(2H, bs, phthalimide ring H×2), 7.51-7.54(2H, d, phthalimide ring H×2), 7.89-7.91(2H, d, phthalimide ring H×2)

IR (KBr-Disk) ν cm$^{-1}$: 3073, 1771(C=O), 1717(C=O), 1364(SO$_2$), 1229 (SO$_2$)

Example 67

A resist composition consisting of the following ingredients was prepared.

| | |
|---|---|
| poly (p-hydroxystyrene/styrene/tert-butyl acrylate) [composition ratio: 7/2/1, weight-average molecular weight (Mw) = 10,000, molecular weight distribution (Mw/Mn) = 1.9] | 6.0 g |
| 5,5'-[2,2,2-trifluoro-1-(trifluoromethyl)ethylidene]bis[2-(3-trifluoromethylphenylsulfonyl)oxy-1H-isoindole-1,3(2H)-dione] [the compound of Example 46] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed as follows using the above-described resist composition. Each of the processes thereof is shown in FIG. 1.

Namely, the resist composition was filtered using a membrane filter with 0.1 μm pore size, followed by spin-coating on a silicon substrate 1, pre-baking at 130° C. for 90 sec. on a hot plate, to obtain a resist film 2 with thickness of 0.3 μm (FIG. 1 (a)). Then EB-drawn pattern 3 was drawn using an EB direct writing equipment (acceleration voltage of 50 KeV) (FIG. 1(b)), followed by baking at 120° C. for 60 sec. on a hot plate (FIG. 1(c)), developing using a 2.38% aqueous solution of tetramethylammonium hydroxide and washing with water, to form a positive resist pattern 2a (FIG. 1(d)). The positive resist pattern thus obtained showed resolution of 100 nm L&S (0.1 μm L&S) with sensitivity of 4.0 μC/cm$^2$. Pattern profile was rectangular.

In FIG. 1, each number has the following meaning:

1: silicon substrate
2: resist film of the present invention
3: EB-drawn pattern
4: bake
2a: pattern.

Example 68

A pattern was formed similarly as in Example 67 except that exposure was carried out using a KrF excimer laser stepper (NA 0.55) instead of the EB direct writing equipment in Example 67. The positive resist pattern thus obtained showed resolution of 0.15 μm L&S with sensitivity of 5 mJ/cm$^2$. Pattern profile was nearly rectangular.

Example 69

A resist composition consisting of the following ingredients was prepared.

| | |
|---|---|
| poly (p-1-ethoxyethoxystyrene/p-hydroxystyrene/p-tert-butoxystyrene) [composition ratio: 26/64/10, Mw = 10,000, Mw/Mn = 1.02] | 6.0 g |
| 5,5'-oxybis[2-(10-camphorsulfonyl)oxy-1H-isoindole-1,3(2H)-dione] [the compound of Example 49] | 0.3 g |
| tris[2-(2-methoxyethoxy)ethyl]amine | 0.01 g |
| fluorine-containing nonionic surfactant [commercial product] | 0.1 g |
| propylene glycol monomethyl ether acetate | 60.0 g |

The above-described resist, composition was filtered using a membrane filter with 0.1 μg m pore size, followed by spin-coating on a silicon substrate, pre-baking at 130° C. for 90 sec. on a hot plate, to obtain a resist film with a thickness of 0.3 μm. Then a pattern was transcripted by irradiation using an EB direct writing equipment (acceleration voltage of 50 KeV), followed by baking at 105° C. for 60 sec. on a hot plate, developing using a 2.38% aqueous solution of tetramethylammonium hydroxide and washing with water, to form a positive resist pattern. The positive resist pattern thus obtained showed resolution of 100 nm L&S (0.1 μm L&S) with sensitivity of 2.8 μC/cm$^2$. Pattern profile was nearly rectangular.

Example 70

A pattern was formed similarly as in Example 69 except that exposurewas carried out using a KrF excimer laser stepper instead of the EB direct writing equipment in Example 69. The positive resist pattern thus obtained showed resolution of 0.15 μm L&S with sensitivity of 3 mJ/cm$^2$. Pattern profile was nearly rectangular.

Example 71

A resist composition consisting of the following ingredients was prepared.

| | |
|---|---|
| poly (p-tert-butoxystyrene/p-hydroxystyrene) [composition ratio: 33/67, Mw = 10,000, Mw/Mn = 1.02] | 6.0 g |
| 5,5'-[2,2,2-trifluoro-1-(trifluoromethyl)ethylidene]bis[2-(4-toluenesulfonyl)oxy-1H-isoindole-1,3(2H)-dione] [the compound of Example 48] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as, in Example 67 using the above-described resist composition. The positive resist pattern thus obtained showed resolution of 100 nm L&S (0.1 μm L&S) with sensitivity of 3.0 μC/cm$^2$. Pattern profile was nearly rectangular.

Example 72

A pattern was formed similarly as in Example 67 except that exposure was carried out using a KrF excimer laser stepper instead of the EB direct writing equipment in Example 71. The positive resist pattern thus obtained showed resolution of 0.15 µm L&S with sensitivity of 3 mJ/cm$^2$. Pattern profile was nearly rectangular.

Example 73

A resist composition consisting of the following ingredients was prepared.

| | |
|---|---|
| poly (p-tert-butoxystyrene/p-hydroxystyrene) [composition ratio: 1/9, Mw = 2,500, Mw/Mn = 1.02] | 6.0 g |
| 5,5'-oxybis[2-(pentafluorobenzenesulfonyl)oxy-1H-isoindole-1,3(2H)-dione] [the compound of Example 51] | 0.3 g |
| 2,4,6-tris (methoxymethyl)amino-1,3,5-s-triazine | 2.0 g |
| dicyclohexylmethylamine | 0.01 g |
| fluorine-containing nonionic surfactant [commercial product] | 0.1 g |
| propylene glycol monomethyl ether acetate | 58.0 g |

A pattern was formed as follows using the above-described resist composition. Each of the processes thereof is shown in FIG. 2.

Namely, the above-described resist composition was filtered using a membrane filter with 0.1 µm pore size, followed by spin-coating on a silicon substrate 1, pre-baking at 130° C. for 90 sec. on a hot plate, to obtain a resist film 5 with thickness of 0.3 µm (FIG. 2(a)). Then a EB-drawn pattern was drawn using an EB direct writing equipment (acceleration voltage of 50 KeV) (FIG. 2(b)), followed by baking at 130° C. for 60 sec. on a hot plate (FIG. 2(c)); developing using a 2.38% aqueous solution of tetramethylammonium hydroxide and washing with water, to form a negative resist pattern 5a (FIG. 2(d)). The negative resist pattern thus obtained showed resolution of 100 nm L&S (0.1 µm L&S) with sensitivity of 4.5 µC/cm$^2$. Pattern profile was nearly rectangular.

Figure 2:
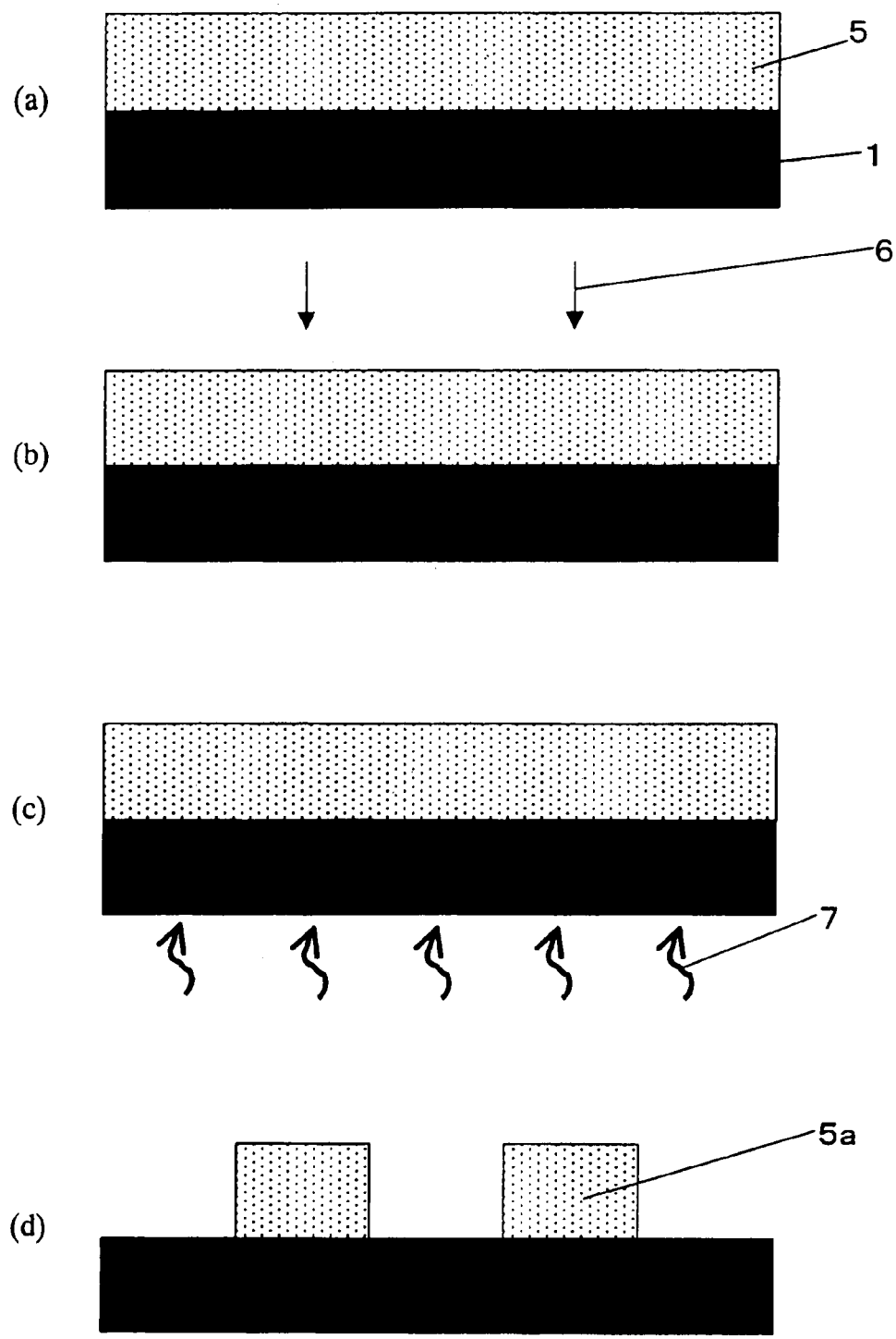
FIG. 2 is a cross-sectional view showing each process of a method of pattern formation using a resist composition of the present invention (Example 73).

In FIG. 2, each number has the following meaning:
1: silicon substrate
4: resist film of the present invention
6: EB-drawn pattern
7: bake
5a: pattern.

Example 74

A resist composition consisting of the following ingredients was prepared.

| | |
|---|---|
| poly (p-tert-butoxystyrene/p-hydroxystyrene) [composition ratio: 2/8, Mw = 8,500, Mw/Mn = 1.05] | 6.0 g |
| 5,5'-[2,2,2-trifluoro-1-(trifluoromethyl)ethylidene]bis[2-pentafluorobenzenesulfonyl]oxy-1H-isoindole-1,3(2H)-dione] [the compound of Example 54] | 0.3 g |
| 4,4',4''-tris(4-tert-butoxycarbonylmethoxyphenyl)methane | 1.5 g |
| dicyclohexylmethylamine | 0.01 g |
| fluorine-containing nonionic surfactant [commercial product] | 0.1 g |
| propylene glycol monomethyl ether acetate | 58.0 g |

A pattern was formed similarly as in Example 67 using the above-described resist composition. The positive resist pattern thus obtained showed resolution of 100 nm L&S (0.1 µm L&S) with sensitivity of 4.0 µC/cm$^2$. Pattern profile was nearly rectangular.

Example 75

A resist composition consisting of the following ingredients was prepared.

| | |
|---|---|
| poly (p-tert-butoxycarbonylmethoxystyrene/styrene/p-hydroxystyrene) [composition ratio: 25/10/65, Mw = 10,000, Mw/Mn = 1.85] | 6.0 g |
| 5,5'-oxybis[4-trifluoromethylphenylsulfonyloxy-1H-isoindole-1,3(2H)-dione] [the compound of Example 60] | 0.3 g |
| dicyclohexylmethylamine | 0.01 g |
| fluorine-containing nonionic surfactant [commercial product] | 0.1 g |
| ethyl lactate | 30.0 g |
| ethyl 3-ethoxypropionate | 30.0 g |

A pattern was formed similarly as in Example 67 using the above-described resist composition. The positive resist pattern thus obtained showed resolution of 100 nm L&S (0.1 µm L&S) with sensitivity of 4.0 µC/cm$^2$. Pattern profile was nearly rectangular.

Example 76

A resist composition consisting of the following ingredients was prepared.

| | |
|---|---|
| poly (p-hydroxystyrene/styrene/tert-butyl acrylate) [composition ratio: 7/2/1, weight-average molecular weight (Mw) = 10,000, molecular weight distribution (Mw/Mn) = 1.9] | 6.0 g |
| 5,5'-oxybis[2-(3,5-di-trifluoromethylphenylsulfonyl)oxy-1H-isoindole-1,3(2H)-dione] [the compound of Example 53] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 67 using the above described resist composition. The positive resist pattern thus obtained showed resolution of 100 nm L&S (0.1 µm L&S) with sensitivity of 4.0 µC/cm$^2$. Pattern profile was nearly rectangular.

Example 77

A resist composition consisting of the following ingredients was prepared.

| | |
|---|---|
| poly (p-tert-butoxystyrene/p-hydroxystyrene) [composition ratio: 33/67, Mw = 10,000, Mw/Mn = 1.02] | 0.3 g |
| 5,5'-[2,2,2-trifluoro-1-(trifluoromethyl)ethylidene]bis [2-(10-camphorsulfonyl)oxy-1H-isoindole-1,3(2H)-dione] [the compound of Example 50] | 6.0 g |
| 4-N,N-dimethylaminopyridine | 0.01 g |
| fluorine-containing nonionic surfactant [commercial product] | 0.1 g |
| propylene glycol monomethyl ether acetate | 60.0 g |

A pattern was formed similarly as in Example 67 using the above-described resist composition. The positive resist pattern thus obtained showed resolution of 100 nm L&S (0.1 µm L&S) with sensitivity of 5.0 µC/cm². Pattern profile was nearly rectangular.

Example 78

A resist composition consisting of the following ingredients was prepared.

| | |
|---|---|
| poly (p-1-ethoxyethoxystyrene/p-hydroxystyrene/p-tert-butoxystyrene) | 6.0 g |
| [composition ratio: 26/64/10, Mw = 10,000, Mw/Mn = 1.02] | |
| 5,5'-bis[2-n-butanesulfonyloxy-1H-isoindole-1,3(2H)-dione] | 0.3 g |
| [the compound of Example 52] | |
| trioctylamine | 0.01 g |
| fluorine-containing nonionic surfactant | 0.1 g |
| [commercial product] | |
| propylene glycol monomethyl ether acetate | 60.0 g |

A pattern was formed similarly as in Example 70 using the above-described resist composition. The positive resist pattern thus obtained showed resolution 0.15 µm L&S with sensitivity of 4 mJ/cm². Pattern profile was nearly rectangular.

Example 79

A resist composition consisting of the following ingredients was prepared.

| | |
|---|---|
| poly (p-tert-butoxystyrene/p-hydroxystyrene) | 6.0 g |
| [composition ratio: 30/70, Mw = 8,000, Mw/Mn = 1.01] | |
| 5,5'-oxybis[2-(3-trifluoromethylphenylsulfonyl)oxy-1H-isoindole-1,3(2H)-dione] | 0.3 g |
| [the compound of Example 45] | |
| dicyclohexylmethylamine | 0.01 g |
| fluorine-containing nonionic surfactant | 0.1 g |
| [commercial product] | |
| ethyl lactate | 60.0 g |

A pattern was formed similarly as in Example 67 using the above-described resist composition. The positive resist pattern thus obtained showed resolution of 100 nm L&S (0.1 µm L&S) with sensitivity of 4.0 µC/cm². Pattern profile was nearly rectangular.

Example 80

A resist composition consisting of the following ingredients was prepared.

| | |
|---|---|
| poly (p-tert-butoxystyrene/p-hydroxystyrene) | 6.0 g |
| [composition ratio: 30/70, Mw = 8,000, Mw/Mn = 1.01] | |
| 5,5'-oxybis[2-(3-trifluoromethylphenylsulfonyl)oxy-1H-isoindole-1,3(2H)-dione] | 0.3 g |
| [the compound of Example 45] | |
| dicyclohexylmethylamine | 0.01 g |
| fluorine-containing nonionic surfactant | 0.1 g |
| [commercial product] | |
| ethyl lactate | 50.0 g |
| γ-butyrolactone | 10.0 g |

A pattern was formed similarly as in Example 68 using the above-described resist composition. The positive resist pattern thus obtained showed resolution of 0.15 µm L&S with sensitivity of 5 mJ/cm². Pattern profile was nearly rectangular.

Example 81

A resist composition consisting opf the following ingredients was prepared.

| | |
|---|---|
| poly(p-hydroxystyrene/styrene/tert-butyl acrylate) | 5.0 g |
| [composition ratio: 7/2/1, weight-average molecular weight (Mw) = 10,000, molecular weight distribution (Mw/Mn) = 1.9] | |
| poly(p-tert-butoxycarbonyloxystyrene/p-hydroxystyrene) | 1.0 g |
| [composition ratio: 35/65, Mw = 10,000, Mw/Mn = 1.02] | |
| 5,5'-oxybis[2-(3,5-di-trifluoromethylphenylsulfonyl)oxy-1H-isoindole-1,3(2H)-dione] | 0.2 g |
| [the compound of Example 53] | |
| 2,4,6-trimethylphenyldiphenylsulfonium pentafluorobenzenesulfonate | 0.1 g |
| dicyclohexylmethylamine | 0.01 g |
| fluorine-containing nonionic surfactant | 0.1 g |
| [commercial product] | |
| propylene glycol monomethyl ether acetate | 60.0 g |

A pattern was formed similarly as in Example 67 using the above-described resist composition. The positive resist pattern thus obtained showed resolution of 100 nm L&S (0.1 µm L&S) with sensitivity of 4.0 µC/cm². Pattern profile was nearly rectangular.

Example 82

A resist composition consisting of the following ingredients was prepared.

| | |
|---|---|
| poly(p-hydroxystyrene/styrene/tert-butyl acrylate) | 5.0 g |
| [composition ratio: 7/2/1, weight-average molecular weight (Mw) = 10,000, molecular weight distribution (Mw/Mn) = 1.9] | |
| poly(p-tert-butoxystyrene/p-hydroxystyrene) | 1.0 g |
| [composition ratio: 30/70, Mw = 8,000, Mw/Mn = 1.01] | |
| 5,5'-oxybis[2-(3-trifluoromethylphenylsulfonyl)oxy-1H-isoindole-1,3(2H)-dione] | 0.2 g |
| [the compound of Example 45] | |
| triphenylsulfonium pentafluorobenzenesulfonate | 0.1 g |
| dicyclohexylmethylamine | 0.01 g |
| fluorine-containing nonionic surfactant | 0.1 g |
| [commercial product] | |
| ethyl lactate | 60.0 g |

A pattern was formed similarly as in Example 67 using the above-described resist composition. Thepositive resist pattern thus obtained showed resolution of 100 nm L&S (0.1 µm L&S) with sensitivity of 4.0 µC/cm². Pattern profile was nearly rectangular.

Example 83

A resist composition consisting of the following ingredients was prepared.

| | |
|---|---|
| poly(p-hydroxystyrene/styrene/tert-butyl acrylate) | 5.0 g |
| [composition ratio: 7/2/1, weight-average molecular weight (Mw) = 10,000, molecular weight distribution (Mw/Mn) = 1.9] | |
| poly(p-tert-butoxycarbonyloxystyrene/p-hydroxystyrene) | 1.0 g |
| [composition ratio: 35/65, Mw = 10,000, Mw/Mn = 1.02] | |
| 5,5'-oxybis[2-(pentafluorobenzenesulfonyl)oxy-1H-isoindole-1,3(2H)-dione] [the compound of Example 51] | 0.2 g |
| bis(4-tolyl)iodonium nonafluorobutanesulfonate | 0.1 g |
| cyclohexylmethylamine | 0.01 g |
| fluorine-containing nonionic surfactant | 0.1 g |
| [commercial product] | |
| propylene glycol monomethyl ether acetate | 40.0 g |
| ethyl lactate | 20.0 g |

A pattern was formed similarly as in Example 67 using the above-described resist composition. The positive resist pattern thus obtained showed resolution of 100 nm L&S (0.1 µm L&S) with sensitivity of 4.0 µC/cm². Pattern profile was nearly rectangular.

Example 84

A resist composition consisting of the following ingredients was prepared.

| | |
|---|---|
| poly(p-1-ethoxyethoxystyrene/p-hydroxystyrene/p-tert-butoxystyrene) [composition ratio: 25/65/10, Mw = 15,000, Mw/Mn = 1.85] | 4.5 g |
| poly(p-1-isobutoxyethoxystyrene/p-hydroxystyrene) [composition ratio: 30/70, Mw = 10,000, Mw/Mn = 1.02] | 1.5 g |
| 5,5'-[2,2,2-trifluoro-1-(trifluoromethyl)ethylidene]bis[2-(10-camphorsulfonyl)oxy-1H-isoindole-1,3(2H)-dione] [the compound of Example 50] | 0.2 g |
| 4-tolyldiphenylsulfonium 4-toluenesulfonate | 0.1 g |
| tris[2-(2-methoxyethoxy)ethyl]amine | 0.01 g |
| fluorine-containing nonionic surfactant [commercial product] | 0.1 g |
| propylene glycol monomethyl ether acetate | 60.0 g |

A pattern was formed similarly as in Example 69 using the above-described resist composition. The contact hole pattern thus obtained showed resolution of 100 nm (0.1 µm) with sensitivity of 4.0 µC/cm². Pattern profile was nearly vertical.

Example 85

A resist composition consisting of the following ingredients was prepared.

| | |
|---|---|
| poly(p-tert-butoxystyrene/p-hydroxystyrene) [composition ratio: 33/67, Mw = 10,000, Mw/Mn = 1.02] | 6.0 g |
| 5,5'-oxybis[2-(4-n-propylbenzenesulfonyl)oxy-1H-isoindole-1,3(2H)-dione] [the compound of Example 64] | 0.3 g |
| dicyclohexylmethylamine | 0.01 g |
| fluorine-containing nonionic surfactant [commercial product] | 0.1 g |
| ethyl lactate | 60.0 g |

A pattern was formed similarly as in Example 67 using the above-described resist composition. The positive resist pattern thus obtained showed resolution of 100 nm L&S (0.1 µm L&S) with sensitivity of 4.0 µC/cm². Pattern profile was nearly rectangular.

Example 86

A resist composition consisting of the following ingredients was prepared.

| | |
|---|---|
| poly(p-hydroxystyrene/styrene/tert-butyl acrylate) [composition ratio: 7/2/1, weight-average molecular weight (Mw) = 10,000, molecular weight distribution (Mw/Mn) = 1.9] | 6.0 g |
| 5,5'-oxybis[2-(3-trifluoromethylphenylsulfonyl)oxy-1H-isoindole-1,3(2H)-dione] [the compound of Example 45] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 67 using the above-described resist composition. The positive resist pattern thus obtained showed resolution of 100 nm L&S (0.1 µm L&S) with sensitivity of 4.4 µC/cm². Pattern profile was nearly rectangular.

Example 87

A resist composition consisting of the following ingredients was prepared.

| | |
|---|---|
| poly(p-hydroxystyrene/styrene/tert-butyl acrylate) [composition ratio: 7/2/1, weight-average molecular weight (Mw) = 10,000, molecular weight distribution (Mw/Mn) = 1.9] | 6.0 g |
| 5,5'-oxybis[2-(4-trifluoromethylphenylsulfonyl)oxy-1H-isoindole-1,3(2H)-dione] [the compound of Example 60] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 67 using the above-described resist composition. The positive resist pattern thus obtained showed resolution of 100 nm L&S (0.1 µm L&S) with sensitivity of 4.6 µC/cm². Pattern profile was nearly rectangular.

Comparative Example 6

A resist composition consisting of the following ingredients was prepared.

| | |
|---|---|
| poly(p-hydroxystyrene/styrene/tert-butyl acrylate) [composition ratio: 7/2/1, weight-average molecular weight (Mw) = 10,000, molecular weight distribution (Mw/Mn) = 1.9] | 6.0 g |
| 5,5'-oxybis[2-(4-toluenesulfonyl)oxy-1H-isoindole-1,3(2H)-dione] [the compound of Reference Example 8] | 0.3 g |
| dicyclohexylmethylamine | 0.01 g |
| fluorine-containing nonionic surfactant [commercial product] | 0.1 g |
| propylene glycol monomethyl ether acetate | 60.0 g |

Preparation of the resistcomposition comprising the above ingredients was conducted but could not be succeeded due to no dissolution of the acid generator.

Comparative Example 7

A resist composition consisting of the following ingredients was prepared.

| | |
|---|---|
| poly(p-tert-butoxystyrene/p-hydroxystyrene) [composition ratio: 33/67, Mw = 10,000, Mw/Mn = 1.02] | 6.0 g |
| 5,5'-oxybis[2-(4-toluenesulfonyl)oxy-1H-isoindole-1,3(2H)-dione] [the compound of Reference Example 8] | 0.3 g |
| dicyclohexylmethylamine | 0.01 g |
| fluorine-containing nonionic surfactant [commercial product] | 0.1 g |
| ethyl lactate | 60.0 g |

Preparation of the resist composition comprising the above ingredients was conducted but could not be succeeded due to no dissolution of the acid generator.

Comparative Example 8

A resist composition consisting of the following ingredients was prepared.

| | |
|---|---|
| poly(p-tert-butoxystyrene/p-hydroxystyrene) [composition ratio: 33/67, Mw = 10,000, Mw/Mn = 1.02] | 6.0 g |
| 5,5'-oxybis[2-trifluoromethanesulfonyloxy-1H-isoindole-1,3(2H)-dione] [the compound of Reference Example 9] | 0.3 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed similarly as in Example 67 using the above-described resist composition. Each of the processes thereof is shown in FIG. 3.

Namely, the resist composition was filtered using a membrane filter with 0.1 μm pore size, followed by spin-coating on a silicon substrate 1, pre-baking at 130° C. for 90 sec. on a hot plate to obtain a resist film 8 with a thickness of 0.3 μm (FIG. 3(a)) Then EB-drawn pattern 3 was drawn using an EB direct writing equipment (acceleration voltage of 50 KeV) (FIG. 3(b)), followed by baking at 120° C. for 60 sec. on a hot plate (FIG. 3(c)), developing using a 2.38% aqueous solution of tetramethylammonium hydroxide and washing with water, to form a positive resist pattern 8a (FIG. 3(d)). The positive resist pattern 8a thus obtained showed resolution of 110 nm L&S (0.11 μm L&S) with sensitivity of 8.0 μC/cm², but could not resolve 100 nm L&S. The pattern 8a was, poor with reversely tapered profile.

Figure 3:
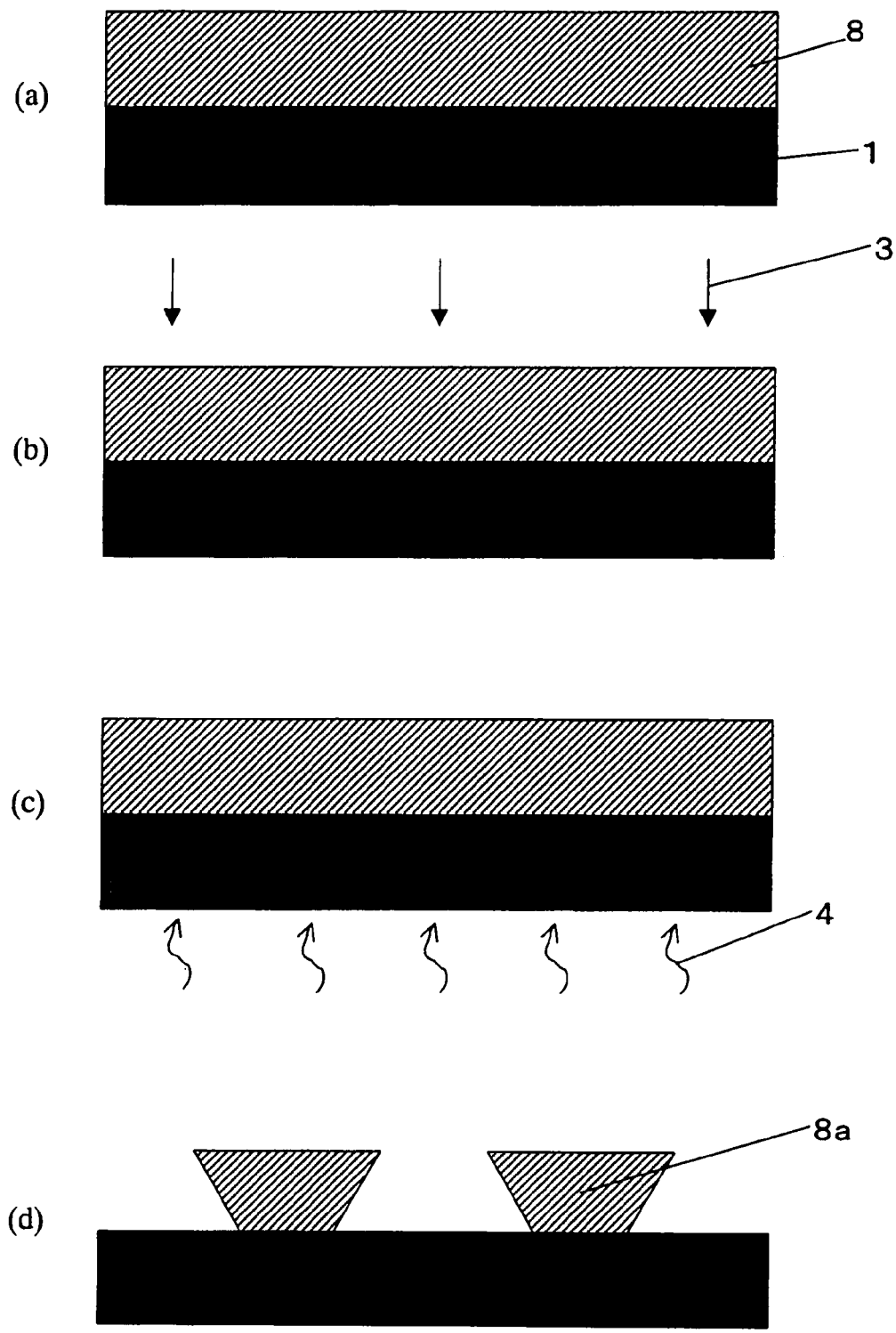
FIG. 3 is a cross-sectional view showing each process of a method of pattern formation using a conventional resist composition (Comparative Example 8).

In FIG. 3, each number has the following meaning:
1: silicon substrate
3: EB-drawn pattern
4: bake
8: a resist film of the Comparative Example
8a: pattern

Comparative Example 9

A resist composition consisting of the following ingredients was prepared.

| | |
|---|---|
| poly(p-hydroxystyrene) [weight-average molecular weight (Mw) = 10,000, molecular weight distribution (Mw/Mn) = 1.9] | 6.0 g |
| 5,5'-oxybis[2-trifluoromethanesulfonyloxy-1H-isoindole-1,3(2H)-dione] [the compound of Reference Example 9] | 0.3 g |
| 2,4,6-tris(methoxymethyl)amino-1,3,5-s-triazine | 0.12 g |
| dicyclohexylmethylamine | 0.01 g |
| fluorine-containing nonionic surfactant [commercial product] | 0.1 g |
| propylene glycol monomethyl ether acetate | 60.0 g |

A pattern was formed as follows similarly as in Example 85 using the above described resist composition. Each of the processes thereof is shown in FIG. 4.

Namely, the resist composition was filtered using a membrane filter with 0.1 μm pore size, followed by spin-coating on a silicon substrate 1, pre-baking at 130° C. for 90 sec. on a hot-plate, to obtain a resist film 9 with a thickness of 0.3 μm (FIG. 4(a)). Then EB-drawn-pattern 6 was drawn using an EB direct writing equipment (acceleration voltage of 50 KeV) (FIG. 4(b)) followed by baking at 130° C. for 60 sec. on a hot plate (FIG. 4(c)), developing using a 2.38% aqueous solution of tetramethylammonium hydroxide and washing with water, to form a negative resist pattern 9a (FIG. 4(d)). The negative resist pattern thus obtained showed resolution of 120 nm L&S (0.12 μm L&S) with sensitivity of 9.5 μC/cm², but could not resolve 110 nm L&S. The pattern 9a had poor profile.

In FIG. 4, each number has the following meaning:
1: silicon substrate
6: EB-drawn pattern
7: bake
9: a resist film of the Comparative Example
9a: pattern As is clear from the result of each Example, the bisphthalimidesulfonate compound of the present invention shown by the general formula [26], was found to be very useful as an acid generator for a chemically amplified resist composition. While, the conventional compound very similar to the compound shown by the general formula [26] was found not to provide a resist composition due to poor solubility as is clear from the results of Comparative Examples 6 and 7, or was difficult to be used due to low sensitivity, low resolution and poor profile as is clear from the comparison of Comparative Examples 8 and 9.

INDUSTRIAL APPLICABILITY

Among the bisimide compounds of the present invention, shown by the general formula [1], the one, wherein R is one shown by the general formula [2], has advantages such as uniform acid generation and high sensitivity, due to high solubility to a resist solvent, and little occurrence of problems including an increase of fine particle during storage, and is different from a conventional ionic compound such as a sulfonium salt, when used as an acid generator for a chemically amplified resist composition.

In addition, since said bisimide compound can easily generate an acid in response to various energy lines such as KrF excimer laser, ArF excimer laser and electron beams, a pattern having high sensitivity, high resolution and good pattern profile can be obtained, when a chemically amplified resist composition comprising said compound is used in.

Furthermore, the bis(N-hydroxy)phthalimide comppund of the present invention, shown by the general formula [25], is not only an important synthetic intermediate of the bisphthalimidesulfonate compound of the present invention, shown by the general formula [26], but also useful as, for example, a cross-linking agent for a polyimide resin, a raw material of various functional materials such as a synthetic intermediate of a photosensitive compound, and a functional material in biochemical fields such as peptide synthesis.

Furthermore, the bisimide compound of the present invention, shown by the general formula [1] is also useful not only as an acid generator for a resist used for fine fabrication, but also as an acid generator for photosensitive polyimide material aimmed at high sensitivity or a cross-linking agent for a polyimide resin.

What is claimed is:
1. A bisimide compound shown by the general formula [5]:

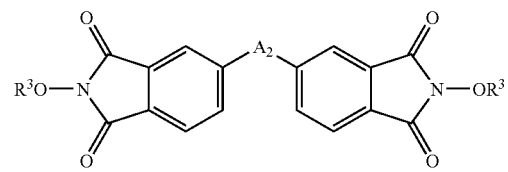

wherein two R³s are each independently a hydrogen atom or a group shown by the general formula [6]:

—SO₂R⁴ [6]

wherein R⁴ is an alkyl group having 1 to 12 carbon atoms, a haloalkyl group having 3 to 12 carbon atoms, an aryl group which may have a substituent, an aralkyl group which may have a substituent, an aromatic heterocyclic group, which may have a substituent, a camphor group or a naphthoquinonediazide group; and the said substituent is selected from the group consisting of a halogen atom, an alkyl group, a haloalkyl group having 1 to 4 atoms, an alkoxy group, a haloalkoxy group having 1 to 4 carbon atoms, an alkenyl group having 2 to 4 carbon atoms, a nitro group, an N,N-dimethylamino group and an acetamide group.

A₂ is a direct-linkage, an —O— group or a —C(CF₃)₂— group; and provided that when A₂ is an —O— group, then at least one R³ is a group shown by the general formula [6], wherein when R⁴ is an aryl group having an alkyl group substituent, the alkyl group has 2 to 12 carbon atoms.

2. The compound according to claim 1, wherein A₂ is a direct-linkage or a —C(CF₃)₂-group; and R³ is a hydrogen atom.

3. The compound according to claim 1, wherein R³ is a group shown by the general formula [6].

4. The compound according to claim 3, wherein the compound shown by the general formula [5] is one shown by the general formula [13]:

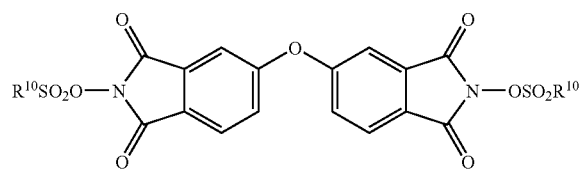

[13]

wherein R¹⁰s are each independently an alkyl group having 1 to 12 carbon atoms, a haloalkyl group having 3 to 12 carbon atoms, or an aryl group which may have a substituent selected from the group consisting of a halogen atom, an alkyl group having 2 to 12 carbon atoms, a haloalkyl group having 1 to 4 carbon atoms, an alkoxy group, a haloalkoxy group having 1 to 4 carbon atoms, an alkenyl group having 2 to 4 carbon atoms, a nitro group, an N,N-dimethylamino group and an acetamide group, an aralkyl group or an aromatic heterocyclic group, which may have a substituent selected from the group consisting of a halogen atom, an alkyl group, a haloalkyl group having 1 to 4 carbon atoms, an alkoxy group, a haloalkoxy group having 1 to 4 carbon atoms, an alkenyl group having 2 to 4 carbon atoms, a nitro group, an N,N-dimethylamino group and an acetamide group, a camphor group or a naphthoquinonediazide group.

5. The compound according to claim 4, wherein the compound shown by the general formula [13] is: 5,5'-oxybis[2-nonafluorobutanesulfonyloxy-1H-isoindole-1,3(2H)-dione]; 5,5'-oxybis[2-heptadecafluorooctanesulfonyloxy-1H-isoindole-1,3(2H)-dione]; 5,5'-oxybis[2-(10-camphorsulfonyl)oxy-1H-isoindole-1,3(2H)-dione]; 5,5'-oxybis[2-(4-trifluoromethylphenylsulfonyl)oxy-1H-isoindole-1,3(2H)-dione]; 5,5'-oxybis[2-(3trifluoromethylphenylsulfonyl)oxy-1H-isoindole-1,3(2H) dione]; 5,5'-oxybis[2-(3,5-ditrifluoromethylphenylsulfonyl)oxy-1H-isoindole-1,3(2H)-dione]; or 5,5'-oxybis[2-(pentafluorobenzenesulfonyl)oxy-1H-isoindole-1,3(2H)-dione].

6. The compound according to claim 3, wherein the compound shown by the general formula [5] is one shown by the general formula [14]:

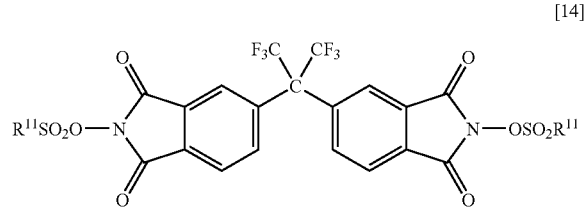

[14]

wherein R¹¹s are each independently an alkyl group having 1 to 12 carbon atoms, a haloalkyl group having 3 to 12 carbon atoms, or an aryl group, an aralkyl group or an aromatic heterocyclic group, which may have a substituent selected from the group consisting of a halogen atom, an alkyl group, a haloalkyl group having 1 to 4 carbon atoms, an alkoxy group, a haloalkoxy group having 1 to 4 carbon atoms, an alkenyl group having 2 to 4 carbon atoms, a nitro group, an N,N-dimethylamino group and an acetamide group, a camphor group or a naphthoquinonediazide group.

7. The compound according to claim 6, wherein the compound shown by the general formula [14] is: 5,5'-[2,2,2-trifluoro-1-(trifluoromethyl)ethylidene]bis[2-nonafluorobutanesulfonyloxy-1H-isoindole-1,3(2H)-dione]; 5,5'-[2,2,2-trifluoro-1-(trifluoromethyl)ethylidene]bis[2-heptadecafluorooctanesulfonyloxy-1H-isoindole-1,3(2H)-dione]; 5,5'-[2,2,2-trifluoro-1-(trifluoromethyl)ethylidene]bis[2-(10-camphorsulfonyl)oxy-1H-isoindole-1,3(2H)-dione]; 5,5'-[2,2,2-trifluoro-1-(trifluoromethyl)ethylidene]bis[2-(4-trifluoromethylphenylsulfonyl)]oxy-1H-isoindole-1,3(2H)-dione]; 5,5'-[2,2,2-trifluoro-1-(trifluoromethyl)ethylidene]bis[2-(3-trifluoromethylphenylsulfonyl)]oxy-1H-isoindole-1,3(2H)-dione]; 5,5'-[2,2,2-trifluoro-1-(trifluoromethyl)ethylidene]bis[2-(3,5-di-trifluoromethylphenylsulfonyl)oxy-1H-isoindole-1,3(2H)-dione]; or 5,5'-[2,2,2-trifluoro-1-(trifluoromethyl)ethylidene]bis[2-pentafluorobenzenesulfonyl)oxy-1H-isoindole-1,3(2H)-dione].

8. The compound according to claim 3, wherein the compound shown by the general formula [5] is one shown by the general formula [15]:

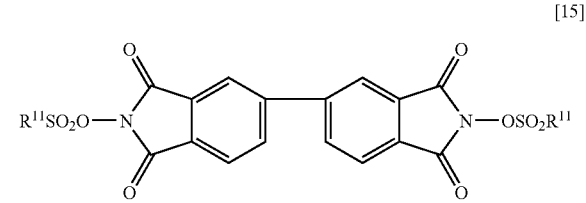

[15]

wherein R¹¹s are each independently an alkyl group having 1 to 12 carbon atoms, a haloalkyl group having 3 to 12 carbon atoms, or an aryl group, an aralkyl group or an aromatic heterocyclic group, which may have a substituent selected from the group consisting of a halogen atom, an alkyl group, a haloalkyl group having 1 to 4 carbon atoms, an alkoxy group, a haloalkoxy group having 1 to 4 carbon atoms, an alkenyl group having 2 to 4 carbon atoms, a nitro group, an N,N-dimethylamino group and an acetamide group, a camphor group or a naphthoquinonediazide group.

9. The compound according to claim 8, wherein the compound shown by the general formula [15] is : 5,5'-bis[2-nonafluorobutanesulfonyloxy-1H-isoindole-1,3(2H)-dione]; 5,5'-bis[2-heptadecafluorooctanesulfonyloxy-1H-isoindole-1,3(2H)-dione]; 5,5'-bis[2-(10-camphorsulfonyl)oxy-1H-isoindole-1,3(2H)-dione]; 5,5'-bis[2-(4-trifluoromethylphenylsulfonyl)oxy-1H-isoindole-1,3(2H)-dione]; 5,5'-bis[2-(3-trifluoromethylphenylsulfonyl)oxy-1H-isoindole-1,3(2H)-dione]; 5,5'-bis[2-(3,5-di-trifluoromethylphenylsulfonyl)oxy-1H-isoindole-1,3(2H)-dione]; or 5,5'-bis[2-(pentafluorobenzenesulfonyl)oxy-1H-isoindole-1,3(2H)-dione].

10. A positive resist composition, which comprises at least one or more of the bisimide compound of claim 3.

11. A negative resist composition, which comprises at least one or more of the bisimide compound of claim 3.

12. A method for pattern formation, which comprises:
a process of forming a positive resist composition in claim 10 on a substrate as a resist film;
a process of exposing an arbitrary pattern on the said resist film; and
a process of forming a positive resist pattern by developing.

13. A method for pattern formation, which comprises:
a process of forming a negative resist composition according to claim 11 on a substrate as a resist film;
a process of exposing an arbitrary pattern on the said resist film; and
a process of forming a negative resist pattern by developing.

* * * * *